United States Patent
Prather et al.

(10) Patent No.: US 9,416,103 B2
(45) Date of Patent: Aug. 16, 2016

(54) USE OF THE AMINOALKYLINDOLE JWH-073-M4 AND RELATED COMPOUNDS AS NEUTRAL CB1 RECEPTOR ANTAGONISTS FOR THE TREATMENT OF ALCOHOLISM, DRUG ABUSE, OBESITY, AND OBESITY-RELATED DISEASES

(71) Applicants: The Board of Trustees of the University of Arkansas, Little Rock, AR (US); The University of Kansas, Lawrence, KS (US)

(72) Inventors: Paul L. Prather, Little Rock, AR (US); Thomas E. Prisinzano, Lawrence, KS (US); William E. Fantegrossi, Little Rock, AR (US); Lisa K. Brents, Little Rock, AR (US); Jeffery Moran, Little Rock, AR (US); Anna Radominska-Pandya, Little Rock, AR (US); Tamara Vasiljevik, Lawrence, KS (US)

(73) Assignees: The Board of Trustees of the University of Arkansas, Little Rock, AR (US); The University of Kansas, Lawrence, KS (US)

( * ) Notice: Subject to any disclaimer, the term of this patent is extended or adjusted under 35 U.S.C. 154(b) by 108 days.

(21) Appl. No.: 14/370,951

(22) PCT Filed: Jan. 8, 2013

(86) PCT No.: PCT/US2013/020706
§ 371 (c)(1),
(2) Date: Jul. 7, 2014

(87) PCT Pub. No.: WO2013/106349
PCT Pub. Date: Jul. 18, 2013

(65) Prior Publication Data
US 2015/0266820 A1     Sep. 24, 2015

Related U.S. Application Data

(60) Provisional application No. 61/584,803, filed on Jan. 9, 2012, provisional application No. 61/586,823, filed on Jan. 15, 2012.

(51) Int. Cl.
*C07D 209/12* (2006.01)
*C07D 209/08* (2006.01)
*A61K 49/00* (2006.01)
(Continued)

(52) U.S. Cl.
CPC .......... *C07D 209/12* (2013.01); *A61K 49/0008* (2013.01); *C07D 209/08* (2013.01); *G01N 33/492* (2013.01); *G01N 33/5088* (2013.01); *G01N 2333/62* (2013.01); *G01N 2400/00* (2013.01); *Y10T 436/144444* (2015.01)

(58) Field of Classification Search
None
See application file for complete search history.

(56) References Cited

PUBLICATIONS

Jarbe TU, DiPatrizio NV. Delta9-THC induced hyperphagia and tolerance assessment: interactions between the CB1 receptor agonist delta9-THC and the CB1 receptor antagonist SR-141716 (rimonabant) in rats. Behavioural pharmacology 2005;16:373-80.

(Continued)

*Primary Examiner* — Nissa Westerberg
(74) *Attorney, Agent, or Firm* — Hugh McTavish

(57) ABSTRACT

Novel alkylindoles that bind tightly to cannabinoid receptors and are neutral antagonists for the cannabinoid 1 receptor and agonists for the cannabinoid 2 receptor are provided. These compounds are useful for treating alcoholism and drug abuse and for treating obesity.

15 Claims, 23 Drawing Sheets

(51) Int. Cl.
G01N 33/50 (2006.01)
G01N 33/49 (2006.01)

(56) References Cited

PUBLICATIONS

Despres JP, Ross R, Boka G, Almeras N, Lemieux I. Effect of rimonabant on the high-triglyceride/ low-HDL-cholesterol dyslipidemia, intraabdominal adiposity, and liver fat: the ADAGIO-Lipids trial. Arteriosclerosis, thrombosis, and vascular biology 2009;29:416-23.

Pi-Sunyer FX, Aronne LJ, Heshmati HM, Devin J, Rosenstock J. Effect of rimonabant, a cannabinoid-1 receptor blocker, on weight and cardiometabolic risk factors in overweight or obese patients: RIO-North America: a randomized controlled trial. Jama 2006;295:761-75.

Auwarter V, Dresen S, Weinmann W, Muller M, Putz M, Ferreiros N. 'Spice' and other herbal blends: harmless incense or cannabinoid designer drugs? J Mass Spectrom 2009;44:832-7.

Seely KA, Prather PL, James LP, Moran JH. Marijuana-based drugs: innovative therapeutics or designer drugs of abuse? Mol Interv 2011;11:36-51.

Every-Palmer S. Synthetic cannabinoid JWH-018 and psychosis: An explorative study. Drug Alcohol Depend 2011;117:152-7.

Atwood BK, Huffman J, Straiker A, Mackie K. JWH018, a common constituent of 'Spice' herbal blends, is a potent and efficacious cannabinoid CB receptor agonist. Br J Pharmacol 2010;160:585-93.

Jarbe TU, Deng H, Vadivel SK, Makriyannis A. Cannabinergic aminoalkylindoles, including AM678=JWH018 found in 'Spice', examined using drug (Delta9-tetrahydrocannabinol) discrimination for rats. Behav Pharmacol 2011;22:498-507.

Wu HM, Yang YM, Kim SG. Rimonabant, a CB1 Inverse Agonist, Inhibits Hepatocyte Lipogenesis by Activating LKB1 and AMPK Axis Downstream of G{alpha}i/o Inhibition. Mol Pharmacol 2011.

Rossi F, Bellini G, Luongo L, Torella M, Mancusi S, De Petrocellis L, et al. The endovanilloid/endocannabinoid system: a new potential target for osteoporosis therapy. Bone 2011;48:997-1007.

Moran CL, Le VH, Chimalakonda KC, Smedley AL, Lackey FD, Owen SN, et al. Quantitative measurement of JWH-018 and JWH-073 metabolites excreted in human urine. Anal Chem 2011;83:4228-36.

Brents LK, Reichard EE, Zimmerman SM, Moran JH, Fantegrossi WE, Prather PL. Phase I Hydroxylated Metabolites of the K2 Synthetic Cannabinoid JWH-018 Retain In Vitro and In Vivo Cannabinoid 1 Receptor Affinity and Activity. PLoS One 2011;6:e21917.

Huffman JW, Zengin G, Wu MJ, Lu J, Hynd G, Bushell K, et al. Structure-activity relationships for 1-alkyl-3-(1-naphthoyl)indoles at the cannabinoid CB(1) and CB(2) receptors: steric and electronic effects of naphthoyl substituents. New highly selective CB(2) receptor agonists. Bioorg Med Chem 2005;13:89-112.

Qi T, Qiu W, Liu Y, Zhang H, Gao X, Liu Y, et al. Synthesis, structures, and properties of disubstituted heteroacenes on one side containing both pyrrole and thiophene rings. J Org Chem 2008;73:4638-43.

Thomas A, Stevenson LA, Wease KN, Price MR, Baillie G, Ross RA, et al. Evidence that the plant cannabinoid Delta9-tetrahydrocannabivarin is a cannabinoid CB1 and CB2 receptor antagonist. Br J Pharmacol 2005;146:917-26.

Aung MM, Griffin G, Huffman JW, Wu M, Keel C, Yang B, et al. Influence of the N-1 alkyl chain length of cannabimimetic indoles upon CB(1) and CB(2) receptor binding. Drug Alcohol Depend 2000;60:133-40.

Prather, P.L. et al. 2000. Activation of Cannabinoid Receptors in Rat Brain by WIN 55212-2 Produces Coupling to Multiple G Protein a-Subunits with Different Potencies. Molecular Pharmacology. 57:1000-1010.

Atwood BK, Lee D, Straiker A, Widlanski TS, Mackie K. CP47,497-C8 and JWH073, commonly found in 'Spice' herbal blends, are potent and efficacious CB(1) cannabinoid receptor agonists. Eur J Pharmacol 2011;659:139-45.

Mikasova L, Groc L, Choquet D, Manzoni OJ. Altered surface trafficking of presynaptic cannabinoid type 1 receptor in and out synaptic terminals parallels receptor desensitization. Proc Natl Acad Sci U S A 2008;105:18596-601.

Li C, Jones PM, Persaud SJ. Role of the endocannabinoid system in food intake, energy homeostasis and regulation of the endocrine pancreas. Pharmacol Ther 2011;129:307-20.

McKallip RJ, Nagarkatti M, Nagarkatti PS. Delta-9-tetrahydrocannabinol enhances breast cancer growth and metastasis by suppression of the antitumor immune response. J Immunol 2005;174:3281-9.

Di Marzo V, Matias I. Endocannabinoid control of food intake and energy balance. Nat Neurosci 2005;8:585-9.

Nogueiras R, Veyrat-Durebex C, Suchanek PM, Klein M, Tschöp J, Caldwell C, Woods SC, Wittmann G, Watanabe M, Liposits Z, Fekete C, Reizes O, Rohner-Jeanrenaud F, Tschöp MH. Peripheral, but not central, CB1 antagonism provides food intake-independent metabolic benefits in diet-induced obese rats. DIabetes 2008; 57(11):2977-91.

Tam J, Vemuri VK, Liu J, Batkai S, Mukhopadhyay B, Godlewski G, et al. Peripheral CB1 cannabinoid receptor blockade improves cardiometabolic risk in mouse models of obesity. J Clin Invest 2010;120:2953-66.

Cabral GA, Griffin-Thomas L. Emerging role of the cannabinoid receptor CB2 in immune regulation: therapeutic prospects for neuroinflammation. Expert reviews in molecular medicine 2009;11:e3.

Parfieniuk A, Flisiak R. Role of cannabinoids in chronic liver diseases. World J Gastroenterol 2008;14:6109-14.

Cluny NL, Vemuri VK, Chambers AP, Limebeer CL, Bedard H, Wood JT, et al. A novel peripherally restricted cannabinoid receptor antagonist, AM6545, reduces food intake and body weight, but does not cause malaise, in rodents. British journal of pharmacology 2010;161:629-42.

Gabbay E, Avraham Y, Ilan Y, Israeli E, Berry EM. Endocannabinoids and liver disease—review. Liver Int. 2005; 25(5):921-6.

Batkai, S. et al. 2001. Endocannabinoids acting at vascular CB1 receptors mediate . . . *Nature Medicine* 7:827-832.

Biala, G. et al. 2001. Rimonabant attenuates sensitization, cross-sensitization and cross-reinstatement of place preference induced by nicotine and ethanol. *Pharmacological Reports* 62:797-807.

Lavon, I et al. 2003. A Novel Synthetic Cannabinoid Derivative Inhibits Inflammatory Liver Damage via Negative Cytokine Regulation. *Molecular Pharmacology* 64:1334-41.

A

B

USE OF THE AMINOALKYLINDOLE JWH-073-M4 AND RELATED COMPOUNDS AS NEUTRAL CB1 RECEPTOR ANTAGONISTS FOR THE TREATMENT OF ALCOHOLISM, DRUG ABUSE, OBESITY, AND OBESITY-RELATED DISEASES

BACKGROUND

Cannabis sativa L., also known as marijuana, has been used for centuries for its psychoactive and medicinal properties [82]. The term cannabinoid was originally coined for any compound isolated from Cannabis [85]. However, today it refers to any compound that demonstrates similar pharmacology to that of $\Delta^9$-THC [83]. $\Delta^9$-THC and related cannabinoids exert their activity on the cannabinoid receptors (CBRs), which were discovered and characterized in the early 1990s [86,87]. There are two main CBR subtypes, CB1 (CB1R) and CB2 (CB2R), both of which are members of the class A GPCR receptor subfamily [88]. CB1Rs are located throughout the body, with the highest percentage being in the central nervous system (CNS), and are involved in many physiological processes [83]. CB2Rs on the other hand are mainly prevalent in the periphery and are interrelated with the immune system [88,89]. Both of the cannabinoid receptors couple through inhibitory G proteins ($G_{i/o}$), which leads to the inhibition of adenylyl cyclase and certain voltage-sensitive calcium channels and activates inward-rectifying potassium channels [88,90]. The cannabinoids represent a structurally different family, in which there are four distinct classes: classical cannabinoids, which includes $\Delta^9$-THC and other pyran-containing analogues; non-classical cannabinoids, which lack the pyran ring such as CP-55,940; aminoalkylindoles exemplified by WIN-55,212-2; and the eicosanoids, which include the endocannabinoids, anandamide (AEA) and 2-arachidonoylglycerol (2-AG) and their derivatives (FIG. 1) [83].

In 1992, a group of scientist at Sterling-Winthrop synthesized pravadoline (FIG. 1), an aminoalkylindole, for the purpose of developing a non-steroidal anti-inflammatory drug (NSAD) [91]. In addition to exhibiting prostaglandin inhibition, it was also shown that it inhibits contractions of the electrically stimulated mouse vas deferens [92,93]. Pravadoline and related derivatives were later shown to interact with cannabinoid CB1Rs and exhibit classical cannabinoid pharmacology in vivo [91,94]. Their interesting pharmacology prompted many researchers into the development of preliminary structure-activity relationships (SAR) for their interaction with the cannabinoid receptors. Reports of aminoalkylindole SAR came in promptly and in the mid-late 1990s Huffman et al. described a series of aminoalkyindoles that possess excellent in vitro and in vivo activity at the same receptor as $\Delta^9$-THC [95-97]. Among the most interesting in the Huffman series were JWH-018, JWH-073, and JWH-200 (FIG. 2A), which exhibited differential selectivity towards CB1Rs and CB2Rs and were shown to be more potent than $\Delta^9$-THC [96,97]. Because of their high activity at the CBRs, these compounds became the main components of an incense blend known as K2/Spice. Despite their increasing popularity, very little is known regarding K2/Spice metabolism, pharmacology, and toxicity.

It has been shown that chronic ethanol (EtOH) exposure down-regulates CB1Rs and increases the brain concentration of AEA and 2-AG [98,99]. In addition, Wang et al., demonstrated that CB1R antagonist rimonabant (SR141716A, FIG. 3) reduces EtOH intake in C57B1/6J mice to levels comparable with that of CB1$^{+/+}$ mice [101]. Furthermore, Hungund et al., also demonstrated that CB1R knock-out mice exhibit reduced voluntary alcohol consumption as compared to wild type mice [102]. Despite all the research being done with rimonabant, this CB1R antagonist was withdrawn from the market in 2007 because of its severe side-effects, which include headaches, nausea, depression, anxiety and suicidal ideation [88,103].

This further supports the notion that novel CB1R antagonist are needed as probes for further investigation of the cannabinoid system, a therapeutic target of interest to numerous research programs around the country. In addition to the studies done on the involvement of the CB1Rs in substance abuse, it was recently shown that CB2Rs may be implicated in substance abuse as well. Specifically, Xi et al., reported that systematic administration of the CB2R agonist JWH-133 (FIG. 3), dose-dependently inhibited intravenous cocaine self-administration in wild-type and CB1R-deficient mice, but not in CB2R-deficient mice [104,105]. This observation was prevented with the pre-treatment of the CB2R antagonist AM630 (FIG. 3), which suggests that the seen effects are mediated by CB2Rs [104]. To investigate if these observations were in fact mediated by brain CB2Rs and not peripheral CB2Rs, the authors intranasally microinjected JWH-133 and saw a dose-dependent inhibition of cocaine self-administration, which was not seen with an intravenous injection of same quantities of the agonist [104]. This in turn confirmed that these observations were indeed mediated by brain CB2Rs.

Activation of cannabinoid 1 receptors (CB1Rs) results in increased hunger and food intake [1].

The health impacts of obesity on the modern Western world are well-known and documented. Obesity is a chronic condition that is associated with the comorbidities of type II diabetes, dyslipidemia, hypertension, cardiovascular disease, and non-alcoholic steatohepatitis (NASH), most of which have inflammatory components. The results of obesity for the individual are often a decrease in longevity and quality of life. In 2008, the estimated financial burden obesity placed on healthcare costs in the United States was a staggering $147 billion, which will presumably continue to increase.

Alcohol and drug addiction and abuse are also major problems in society. New and better agents and methods for treating alcohol and drug abuse and promoting recovery are needed.

SUMMARY

The invention involves the novel idea that a combination CB1R neutral antagonist/CB2R agonist will be an effective agent to treat alcohol abuse and abuse of other drugs, particularly cocaine and opioids. This is an innovative approach to development of alcohol abuse medications because there are current clinically used compounds that exhibit this particular pharmacological profile. This combined pharmacological profile offers two advantages over presently available CB1 antagonists/inverse agonists. First, it provides an opportunity to avoid the side effect profile seen with rimonabant [117]. A neutral antagonist would be expected to retain beneficial properties of rimonabant, but with fewer adverse effects resulting from inverse agonism at CB1Rs. Secondly, incorporation of CB2 agonism into the same molecule provides an opportunity to harness a potential new direction in developing anti-addiction therapies.

JWH-073 is a synthetic cannabinoid that acts similarly to THC, the primary active agent of marijuana, as an agonist of CB1R. The inventors have evidence suggesting that a mono-hydroxylated Phase I metabolite of JWH-073, referred to here as JWH-073-M4, or simply M4, acts as a CB1R neutral competitive antagonist. Evidence from our laboratory also shows the JWH-073-M4 exerts partial agonist action at CB2Rs. Because of these dual actions at both CB1Rs (neutral antagonism) and CB2Rs (partial agonism), we believe that JWH-073-M4 will be an effective agent to treat alcohol and drug abuse.

The endocannabinoid system also has a role in obesity. Activation of cannabinoid 1 receptors (CB1Rs) results in increased hunger and food intake [1], suggesting a role of the endocannabinoid system in energy homeostasis. Obesity promotes development of atherosclerosis and diabetes, and is associated with increased circulating triglyceride levels, insulin resistance, and lipogenesis, and decreased high-density lipoprotein cholesterol levels. CB1R antagonism has importantly been demonstrated to successfully improve many of these obesity-related effects in animal models and clinical trials [2-4]. Furthermore, activation of cannabinoid 2 receptors (CB2Rs), which are located primarily on immune cells, has also been shown to produce anti-inflammatory and immunosuppressive actions [73], which would conceivably counter the inflammation that occurs in obesity.

Based on this, we also believe that M4 will also be an effective agent to treat obesity and related comorbidities.

The evidence that M4 is a CB1R neutral antagonist is that it neither increases no decreases G-protein activity with mouse brain homogenates (FIG. 5) and it antagonist the action of both CB1R agonists and inverse agonists on G-protein activity in mouse brain homogenates (FIGS. 5 and 6). An in vivo assay of hypothermia induction also suggests M4 is a CB1R antagonist (FIG. 9).

However, further evidence in an in vitro assay of its ability to decrease intracellular cAMP concentration (adenylyl cyclase inhibition) in mCB1/Neuro2A cells shows that in this assay M4 acts as a CB1R agonist (FIG. 19A). This is a downstream assay that may amplify the CB1R agonist activity, which may explain why M4 acts as a CB1R neutral antagonist in a hypothermia in vivo assay and in assays of G protein activation with brain homogenates (FIG. 5), but as a CB1R agonist in this in vitro adenylyl cyclase activity assay.

Based on the evidence that in at least some assays described herein, M4 is a CB1R neutral antagonist and a CB2R partial agonist, we proposed that JWH-073-M4 will be an effective agent to treat obesity and related conditions, and to treat alcohol addiction and drug addiction. But in view of the additional evidence that M4 can act as a CB1R agonist, we have screened more compounds to identify other compounds that are CB1R neutral antagonists and CB2R agonists for investigation in vivo to treat obesity and to treat alcohol and drug addiction. We have used M4 as a template for modification to find other compounds that act as CB1R neutral antagonists and CB2R agonists.

We have identified a family of related compounds of formula III that bind both CB1R and CB2R with submicromolar affinity. Three of these compounds, designated TV-5-129, TV-5-249, and TV-6-41, are CB1R neutral antagonists and CB2R agonists. Thus, we believe this indicates they will be effective to treat obesity and to treat drug and alcohol addiction.

We have confirmed in in vivo experiments with mice that TV-5-249 reduces ethanol self-administration.

One embodiment provides a composition comprising a compound of formula III:

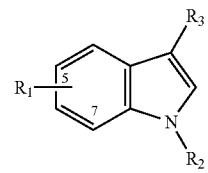

wherein $R_1$ is 5-O-methyl, 7-O-methyl, or 7-OH;
$R_2$ is $C_1$-$C_6$ linear alkyl;
and $R_3$ is

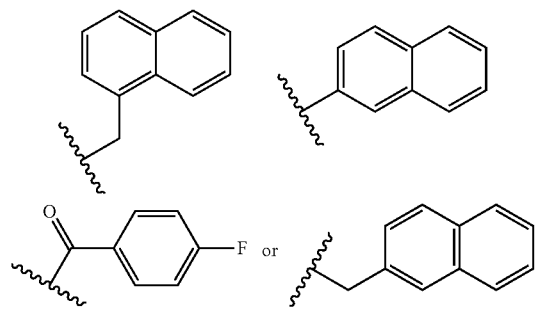

We have shown below that one of the compounds of formula III that we have identified as a CB1R neutral antagonist and CB2R agonist, TV-5-249, does reduce alcohol self-administration in mice, as predicted.

The term "a compound of formula III" as used hereinafter includes the limitations on the identities of $R_1$, $R_2$, and $R_3$ specified above.

Thus, one embodiment provides a method of treating alcohol or drug abuse in a human comprising: administering JWH-073-M4 or a compound of formula III in an amount and for a time effective to treat alcohol or drug abuse in a human in need thereof.

Another embodiment provides a method of treating alcohol or drug abuse in a human comprising: administering a compound of formula III in an amount and for a time effective to treat alcohol or drug abuse in a human in need thereof.

Another embodiment provides a method of treating obesity in a human comprising: administering JWH-073-M4 in an amount and for a time effective to treat obesity in a human in need thereof.

Another embodiment provides a method of treating obesity in a human comprising: administering a compound of formula III in an amount and for a time effective to treat obesity in a human in need thereof.

Another embodiment provides a method of treating or preventing obesity or an obesity-related condition in a human comprising: administering JWH-073-M4 in an amount and for a time effective to treat or prevent obesity or an obesity-related condition in a human in need thereof; wherein the obesity-related condition is selected from the group consisting of insulin resistance, atherosclerosis, NASH, high levels of circulating triglycerides, low-levels of high-density lipoprotein cholesterol, and excessive hunger.

Another embodiment provides a method of treating or preventing obesity or an obesity-related condition in a human comprising: administering a compound of formula III in an amount and for a time effective to treat or prevent obesity or an obesity-related condition in a human in need thereof; wherein the obesity-related condition is selected from the group consisting of insulin resistance, atherosclerosis, NASH, high levels of circulating triglycerides, low-levels of high-density lipoprotein cholesterol, and excessive hunger.

The properties of being a neutral CB1R antagonist and CB2R agonist are also ideal for treating chronic liver disease. CB1R and CB2R are both upregulated in expression in the liver with chronic liver disease. CB1R antagonism and CB2R agonism both decrease inflammation, which is the cause of fibrosis and much of the damage of liver disease. Furthermore, if the drug passes into the brain, a CB1R neutral antagonist will have no effect on constitutive CB1R action, and thus less psychiatric effect than CB1R inverse agonists, which decrease constitutive CB1R action.

Thus, another embodiment provides a method of treating liver disease in a human comprising: administering JWH-073-M4 or a compound of formula III in an amount and for a time effective to treat liver disease in a human in need thereof.

DETAILED DESCRIPTION

Definitions

Figure 1:
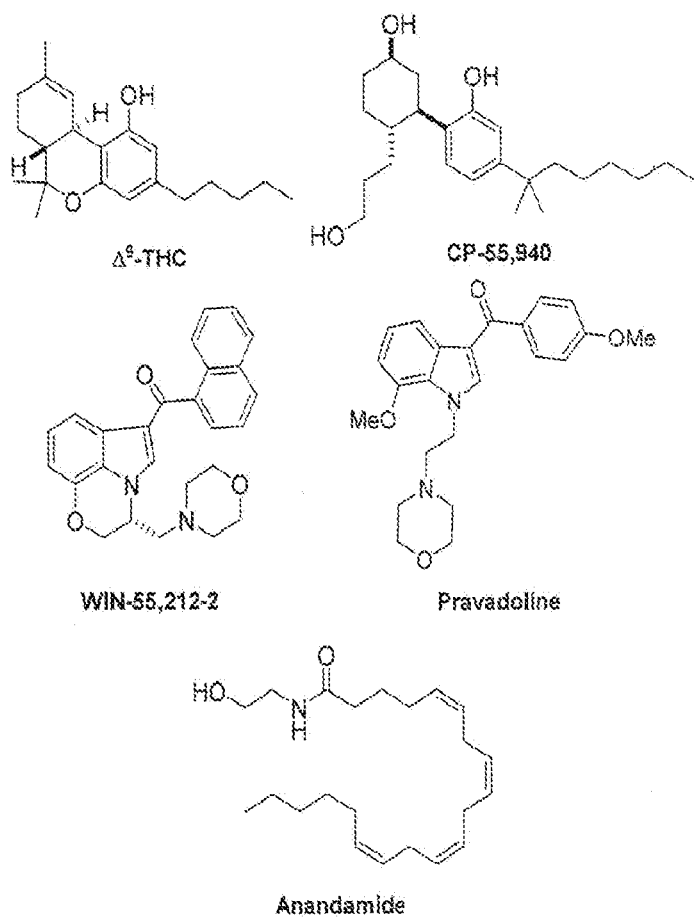
FIG. 1. Representative cannabinoids.

An agonist is a molecule that binds to a specific receptor and triggers a response in the cell expressing the receptor. An exogenous agonist mimics the action of an endogenous biochemical molecule that binds to the same receptor. A partial agonist is a molecule that binds to a specific receptor but only produces a partial physiological response compared to a full agonist.

An inverse agonist is molecule that binds to a specific receptor but exerts the opposite pharmacological effect as compared to that of an agonist, by reducing the intracellular signaling of constitutively active receptors. An inverse agonist may be a partial inverse agonist or a full inverse agonist. The pharmacological effect of an inverse agonist is typically measured as the negative value of the agonist. A partial inverse agonist produces a smaller negative physiological effect than the magnitude of the positive effect produced by the native agonist of the receptor. A full inverse agonist produces a negative physiological effect of magnitude equal to or greater than the magnitude of the positive physiological effect produced by the native agonist for the receptor.

A receptor antagonist is a molecule that binds to a specific receptor and inhibits the function of an agonist and inverse agonist for that specific receptor. When used alone, antagonists have no intrinsic activity.

Receptor agonists, antagonists, and inverse agonists may bind to the same receptor or receptor types. If an agonist has, for example, a positive effect and the inverse agonist has, for example, a negative effect, the antagonist for the receptor may take the receptor back to a neutral state by counteracting both the agonist and inverse agonist.

A peripherally-restricted agent (receptor agonist or antagonist) is an agent that does not cross the blood brain barrier to a pharmaceutically relevant extent and, when given by any route other than intrathecal injection, binds to and affects receptors outside of the brain but does not significantly affect receptor activity in the brain.

DESCRIPTION

Obesity promotes development of atherosclerosis and diabetes, and is associated with increased circulating triglyceride levels, insulin resistance, and lipogenesis, and decreased high-density lipoprotein cholesterol levels. CB1R antagonism has importantly been demonstrated to successfully improve many of these obesity-related effects in animal models and clinical trials [2-4]. Furthermore, activation of cannabinoid 2 receptors (CB2Rs), which are located primarily on immune cells, has also been shown to produce anti-inflammatory and immunosuppressive actions [73], which would conceivably counter the inflammation that occurs in obesity.

We show for the first time that a mono-hydroxylated Phase I metabolite of JWH-073, referred to here as JWH-073-M4, appears to act as a peripherally restricted CB1R neutral competitive antagonist. Evidence from our laboratory also shows the JWH-073-M4 exerts partial agonist action at CB2Rs. Because of these dual actions at both CB1Rs (neutral antagonism) and CB2Rs (partial agonism), we propose that JWH-073-M4 will be an effective agent to treat obesity and related comorbidities.

RIMONABANT, [5-(4-Chlorophenyl)-1-(2,4-dichlorophenyl)-4-methyl-N-(piperidin-1-yl)-1H-pyrazole-3-carboxamide], a CB1R inverse agonist, was introduced to the European market as an anti-obesity agent by Sanofi-Aventis in 2006, but was discontinued in 2008 due to adverse psychiatric effects, such as depression and suicidal ideation. We think a peripherally restricted CB1R antagonist would be superior to one that crosses the blood brain barrier for treating obesity, because a peripherally restricted agent cannot enter the brain to produce psychiatric effects. We also believe a CB1R neutral antagonist, as opposed to an inverse agonist such as RIMONABANT, would have lower side effects as an anti-obesity agent than a CB1R inverse agonist, because it would only lessen the effects of native CB1R agonists but not reverse or disturb the constitutive activity of the receptor. Maintaining a "normal" level of constitutive CB1R signaling is important because the "basal tone" of signaling provided by these receptors in brain presumably modulates several normal homeostatic processes involved in regulation of mood and cognition. JWH-073-M4 has both of these desirable traits.

While the effects of central CB1R antagonism on appetite contribute to their anti-obesity effects, it has been shown that many of the beneficial effects of CB1 antagonists are food-intake independent. For example, CB1Rs present on fat (adipose) cells help control the metabolic level of those cells. Specifically, circulating endogenous cannabinoids (endocannabinoids) activate CB1Rs on fat cells, resulting in a slowing of the metabolism of those cells. CB1R antagonist have been shown to block this reduction in fat cell metabolism. Signaling from peripheral, particularly gut, CB1Rs is also expected to affect appetite.

Also distinguishing JWH-073-M4 from previously developed CB1R agents for use in obesity treatment is that it has partial agonist activity at CB2Rs, which would mean that it should have additional anti-inflammatory and immunosuppressant properties. Such activity is important because several diseases comorbidly associated with obesity, such as cardiovascular disease and NASH, have a pronounced inflammatory component contributing to their pathogenesis. These diseases also have a fibrotic component; and activation of CB1Rs and CB2Rs is pro-fibrotic and anti-fibrotic, respectively. Therefore, concurrent blockade of CB1Rs, coupled with activation of CB2Rs, produced by JWH-073-M4 would be predicted to produce complementary beneficial modulation of cannabinoid receptor activity that would counteract several negative aspects of obesity and its associated long-lasting systemic damage.

Our experiments have shown that JWH-073-M4 binds to CB1Rs and CB2Rs with an affinity of ~120 nM and ~250 nM, respectively. We have also found that this compound blocks both in vitro and in vivo actions of other cannabinoids acting concurrently at CB1Rs, without having an effect on receptor activity when tested alone (without other cannabinoids). This makes it a neutral CB1R antagonist (Example 1 below).

Furthermore, JWH-073-M4 also acts at CB2Rs with partial agonist activity, as demonstrated by inhibition of forskolin-stimulated cAMP production in whole CHO cells stably expressing human CB2Rs (Example 2 below). This shows JWH-074-M4 also acts as a CB2R partial agonist.

Our initial studies in mice show that JWH-073-M4 partially blocks hypothermia induced by the CB1R agonist JWH-018 (Example 1 below), which is both peripherally and centrally mediated, but does not alter other purely centrally-mediated effects of JWH-018, such as suppression of locomotor activity, suppression of response rate in food-maintained responding, or substitution in mice trained to discriminate 10 mg/kg THC (Example 2 below). These mouse studies suggest that JWH-073-M4 is peripherally-restricted and does not enter the CNS in sufficient concentration to produce pharmacological actions.

For treating obesity, obesity-related conditions, and liver disease, it may be desirable that the agent be peripherally restricted, so that it would not have psychiatric effect that may be undesirable. However, rimonabant appears to cause depression and suicidal ideation because it is a CB1R inverse agonist. Compounds that are neutral antagonists or weak partial agonists of the CB1R would be expected to not cause negative moods the way rimonabant does.

For treating alcoholism or drug addiction it is expected that the compounds will have to exert their effects in the brain and not be peripherally restricted.

Analogues of JWH-073-M4 can be tested to identify other compounds that have the desirable properties of being (1) a CB1R neutral antagonist, and (2) a CB2R agonist or partial agonist. Compounds with that are CB1R neutral antagonists, and preferably peripherally restricted, and preferably CB2R agonists or partial agonists, are suitable as agents for treating obesity and obesity related conditions, as well as for treating chronic liver disease. But it is not essential that a compound be peripherally restricted to treat obesity. Non-peripherally restricted compounds can also treat obesity, and in fact the effect on decreasing hunger is probably a brain effect, so in some cases it may be desirable that the compounds not be peripherally restricted. Compounds that are CB1R neutral antagonists and preferably CB2R agonists or partial agonists, and preferably are not peripherally restricted, would be effective agents to treat alcoholism and drug addiction.

Analogues suitable for testing include those of formula I:

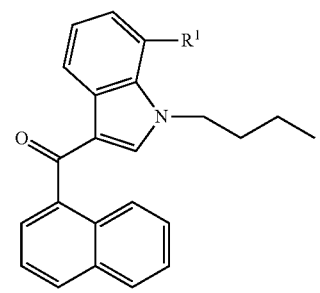

I where $R^1$ is selected from the group consisting of chloro, fluoro, —CH$_3$OH, —CH$_2$O, and —CH$_2$CH$_2$OH.

In another embodiment, analogues for testing include those of formula II:

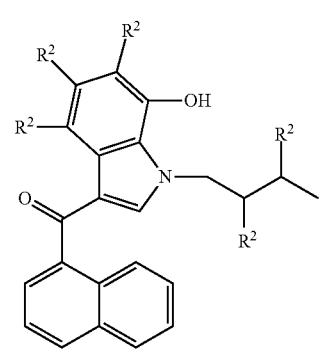

II where one of the $R^2$s is Cl, F, hydroxy, methyl, or hydroxymethyl, and the other $R^2$s are H.

CB2Rs are located primarily on, and modulate the activity of, immune cells. Upregulation of CB2Rs and endocannabinoids occurs in inflammatory conditions, and activation of CB2Rs decreases proliferation, migration, and overall activity of immune cells; thus, CB2R activation is often anti-inflammatory [73].

In chronic liver disease there is a progression from initial insult, leading to chronic inflammation and eventual fibrosis and liver failure. Other groups have demonstrated that CB1R and CB2R are both significantly upregulated in liver disease [76]. The combination of CB1R antagonism with CB2R agonism should produce anti-inflammatory actions and anti-fibrotic effects in chronic liver disease. Therefore, such dual activity of M4 at CB1Rs and CB2Rs could beneficially be useful for prevention of liver cirrhosis, liver fibrosis, and/or liver failure.

Chronic liver disease is a disease process of the liver that involves a process of progressive destruction and regeneration of the liver parenchyma leading to fibrosis and cirrhosis. The causes of chronic liver diseases fall into five groupings: viral causes (hepatitis B and C or cytomegalovirus), metabolic causes (Haemochromatosis or Wilson's disease), autoimmune response causes (primary biliary cirrhosis or primary sclerosing cholangitis), toxin-related causes (alcoholic liver disease or nitrofurantoin), and other miscellaneous causes (right heart failure). However, the main cause of chronic liver disease is overuse of alcohol, leading to cirrhosis and hepatitis.

Thus, another embodiment of the invention provides a method of treating chronic liver disease in a human comprising: administering JWH-073-M4 in an amount and for a time effective to treat chronic liver disease in a human in need thereof. Any of the diseases listed above as causing chronic liver disease, including hepatitis B and C, cytomegalovirus infection, Haemochromatosis, Wilson's disease, primary biliary cirrhosis, primary sclerosin cholangitis, alcoholic liver disease, and nitrofurantoin, are considered herein as types of chronic liver disease. The method of treating chronic liver disease is practiced with the intent and effect of preventing liver cirrhosis, liver fibrosis, or liver failure.

An antagonist to CB1R has also been shown to have a beneficial effect on neurological and cognitive function [81].

Contrary Evidence that the JWH-073 Metabolite M4 Exhibits Both Antagonist and Agonist Activity at CB1 Receptors in Different Assays.

Figure 19:
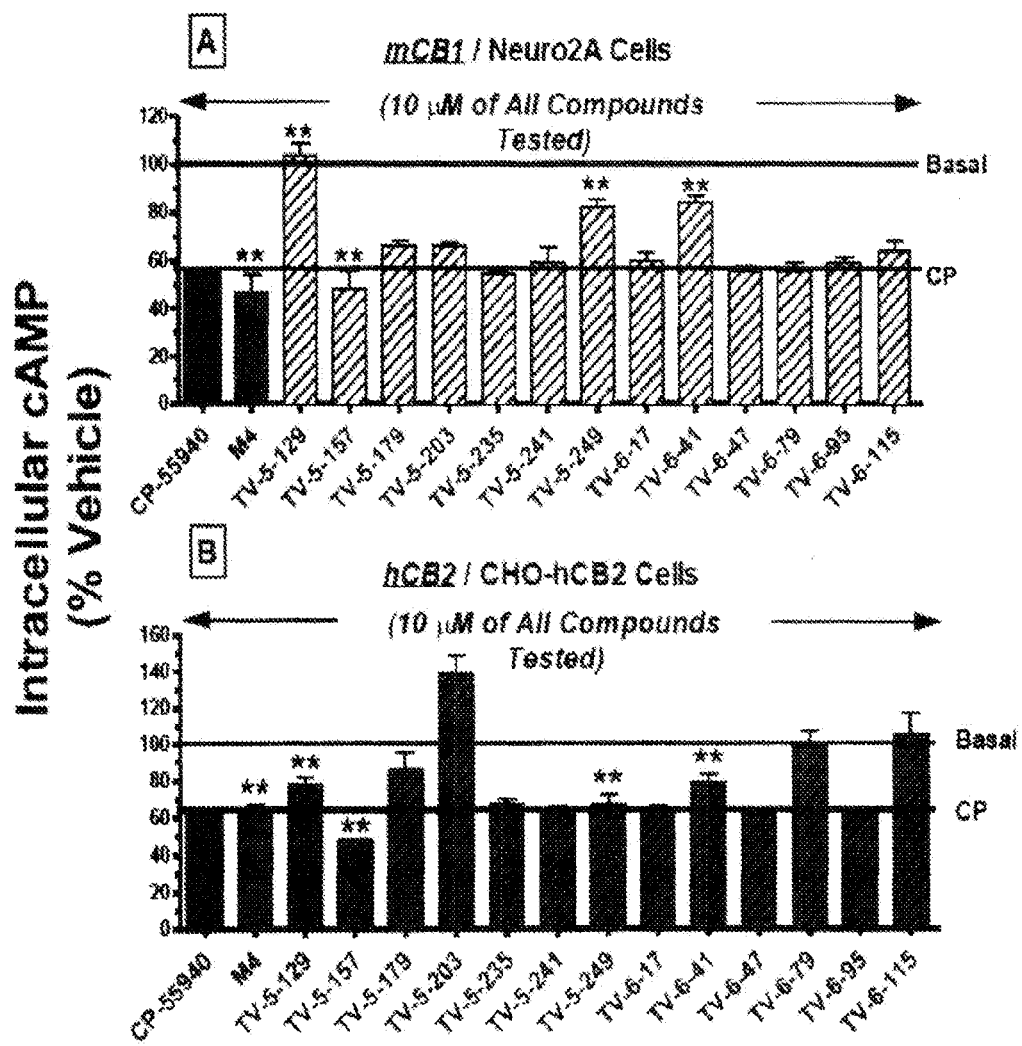
FIG. 19. Screen for M4-analog inhibition of adenylyl cyclase activity via CB receptors. (** Compounds selected for determination of CB1R and CB2R affinity (Ki)).

We report below that a metabolite of the K2/Spice indole-derived cannabinoid JWH-073, M4, acts as a competitive neutral antagonist of CB1R-mediated G-protein activation with a $K_b$ value of 48.1 nM (FIG. 8B) and attenuates JWH-018-induced hypothermia in NIH Swiss mice (FIG. 10) (Example 2). As a result of these encouraging observations, we initiated studies to develop novel neutral CB1R antagonists based on the structure of M4 but with more drug-like properties. However, subsequent results in our laboratory show that M4 unexpectedly exhibits CB1R agonist activity when examined in a second cellular assay (FIG. 19A, Example 6). M4 (1 µM) inhibited activity of the downstream intracellular effector adenylyl cyclase (AC) that was reversed by the CB1R antagonist O-2050 (1 µM). These apparently conflicting observations likely result from the fact that AC-activity may be a more sensitive measure of intrinsic activity of test ligands than G-protein activation, due to signal amplification of this effector occurring downstream from the receptor/G-protein interaction.

We have tested analogues of M4 to identify compounds that are CB1R neutral antagonists and CB2R partial or full agonists.

Figure 17:
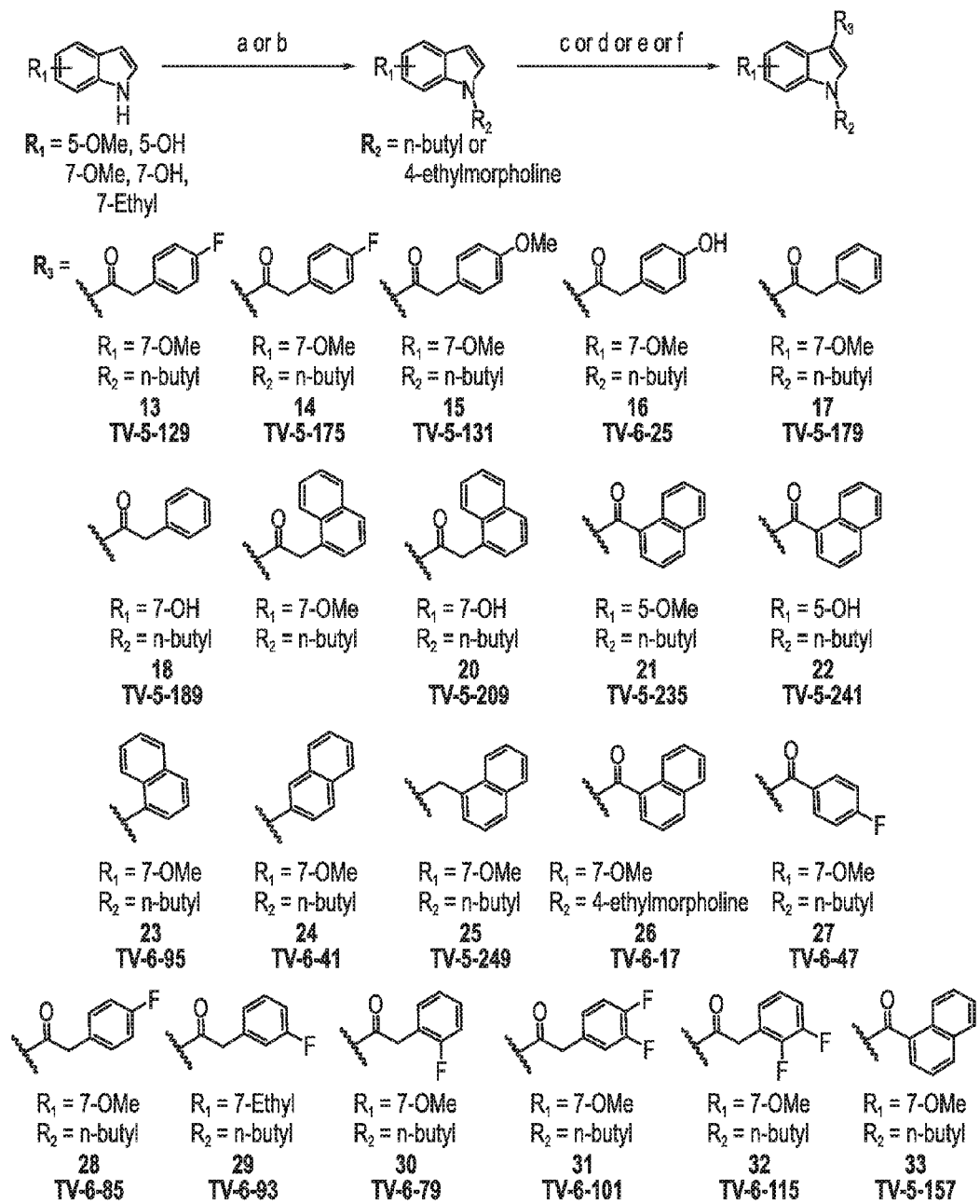
FIG. 17. Reaction scheme 3. Reagents and conditions: (a) 1-bromobutane, KOH, DMF, 50° C.; (b) 4-(2-bromoethyl) morpholine, KOH, DMF, 50° C.; (c) Me$_2$AlCl, RCOCl, DCM, 0° C.; (d) BBr$_3$, DCM, NaHCO$_3$, MeOH, H$_2$O, −78° C.; (e) Pd(PPh$_3$)$_4$, boronic acid, Na$_2$CO$_3$, DME, EtOH; (f) LiAlH$_4$, AlCl$_3$, THF, 0° C.

We first tested a number compounds of formula IV for CB1R and CB2R binding and activity (FIG. 17).

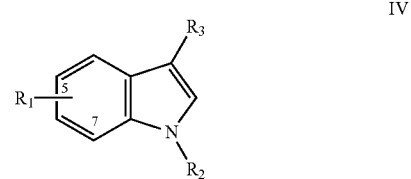

IV

Almost all of the tested compound bound tightly to CB1R and CB2R (Example 6). Almost all are also CB2R agonists. And several are CB1R antagonists. (Example 6.)

In particular, TV-5-129, TV-5-249, and TV-6-41 (FIG. 17) are all CB1R neutral antagonists and CB2R agonists, and all bind to both CB1R and CB2R with submicromolar affinity.

Based on the structures and properties of TV-5-129, TV-5-249, and TV-6-41, and the other analogues tested, it appears that compounds of formula III (formula IV with the specific limitations below on the identities of $R_1$, $R_2$, and $R_3$) are CB1R neutral antagonists and CB2R agonists that bind with submicromolar affinity to both CB1R and CB2R, and thus can be used as agents to treat obesity and to treat alcoholism and drug abuse:

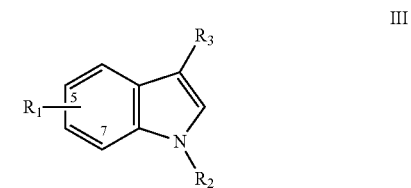

III wherein $R_1$ is 5-O-methyl, 7-O-methyl, or 7-OH;
$R_2$ is $C_1$-$C_6$ linear alkyl;
and $R_3$ is

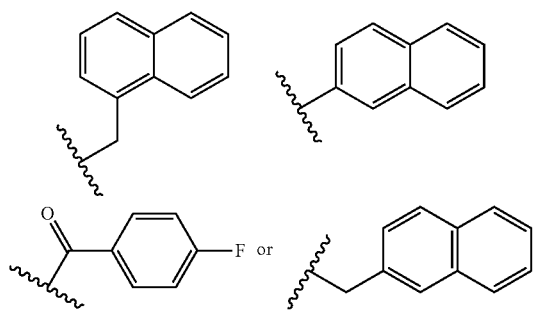

Elsewhere in this patent application, the term "a compound of formula III" is used to mean a compound of formula III wherein $R_1$, $R_2$, and $R_3$ are defined as described immediately above.

In specific embodiments of the compound of formula III, $R_2$ is n-butyl.

In specific embodiments of the compound of formula III, $R_1$ is 7-O-methyl.

In specific embodiments of the compound of formula III, $R_3$ is

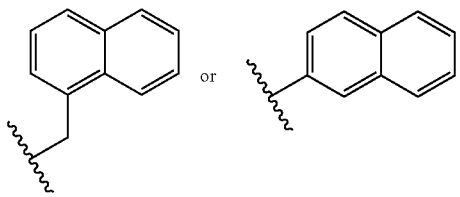 [SMILES: *Cc1cccc2ccccc12 ; *c1ccc2ccccc2c1]

In specific embodiments, the compound of formula III has a $K_D$ for CB1R and CB2R of less than 1 micromolar, or in a more specific embodiment less than 100 nM.

In specific embodiments, the compound of formula III is a CB1R neutral antagonist. For this purpose, a CB1R neutral antagonist is defined as a compound that (1) at 10 μM concentration produces less adenylyl cyclase inhibition in Neuro2A cells than CP-55,900 and no more than 20% increase in adenylyl cyclase activity, and (2) at 1 μM concentration antagonizes the adenylyl cyclase inhibition in Neuro2A cells produced by JWH-073 at 100 nM. These assays are described in Example 6 below, with the results shown in FIGS. 19A and 20B.

In specific embodiments, the compound of formula III is a CB2R agonist. For this purpose, a CB2R agonist is defined as a compound that produces at least 20% decrease in intracellular cAMP (compared to vehicle) in Chinese hamster ovary cells transformed with DNA expressing hCB2 receptors. This assay is described in Example 6, with results shown in FIG. 19B.

In specific embodiments, the compound of formula III is TV-5-249 or TV-6-41 or TV-5-129.

One embodiment of the invention provides a composition comprising a compound of formula III.

In specific embodiments, the composition is a pharmaceutical composition.

In specific embodiments, the pharmaceutical composition is a sterile solution for injection.

In specific embodiments, the pharmaceutical composition is tablet, capsule, gel cap, or pill for oral administration.

In specific embodiments, the pharmaceutical composition is in units dosage form in a dosage effective to treat alcoholism or drug addiction in a human.

Thus, one embodiment of the invention provides a method of treating obesity in a human comprising: administering JWH-073-M4 in an amount and for a time effective to treat obesity in a human in need thereof.

Another embodiment provides a method of treating obesity in a human comprising: administering a compound of formula III in an amount and for a time effective to treat obesity in a human in need thereof.

Another embodiment provides a method of treating or preventing obesity or an obesity-related condition in a human comprising: administering JWH-073-M4 in an amount and for a time effective to treat or prevent obesity or an obesity-related condition in a human in need thereof; wherein the obesity-related condition is selected from the group consisting of insulin resistance, atherosclerosis, NASH, high levels of circulating triglycerides, low-levels of high-density lipoprotein cholesterol, and excessive hunger.

Another embodiment provides a method of treating or preventing obesity or an obesity-related condition in a human comprising: administering a compound of formula III in an amount and for a time effective to treat or prevent obesity or an obesity-related condition in a human in need thereof; wherein the obesity-related condition is selected from the group consisting of insulin resistance, atherosclerosis, NASH, high levels of circulating triglycerides, low-levels of high-density lipoprotein cholesterol, and excessive hunger.

Another embodiment provides a method of increasing high-density lipoprotein cholesterol in a human comprising: administering JWH-073-M4 in an amount and for a time effective to increase high-density lipoprotein cholesterol in a human in need thereof.

Another embodiment provides a method of increasing high-density lipoprotein cholesterol in a human comprising: administering a compound of formula III in an amount and for a time effective to increase high-density lipoprotein cholesterol in a human in need thereof.

Another embodiment provides a method of decreasing circulating triglycerides in a human comprising: administering JWH-073-M4 in an amount and for a time effective to decrease circulating triglycerides in a human in need thereof.

Another embodiment provides a method of decreasing circulating triglycerides in a human comprising: administering a compound of formula III in an amount and for a time effective to decrease circulating triglycerides in a human in need thereof.

Another embodiment provides a method of treating or preventing atherosclerosis in a human comprising: administering JWH-073-M4 in an amount and for a time effective to treat or prevent atherosclerosis in a human in need thereof.

Another embodiment provides a method of treating or preventing atherosclerosis in a human comprising: administering a compound of formula III in an amount and for a time effective to treat or prevent atherosclerosis in a human in need thereof.

Another embodiment provides a method of treating or preventing NASH in a human comprising: administering JWH-073-M4 in an amount and for a time effective to treat or prevent NASH in a human in need thereof.

Another embodiment provides a method of treating or preventing NASH in a human comprising: administering a compound of formula III in an amount and for a time effective to treat or prevent NASH in a human in need thereof.

Another embodiment provides a method of treating or preventing liver disease in a human comprising: administering JWH-073-M4 in an amount and for a time effective to treat or prevent liver disease in a human in need thereof.

Another embodiment provides a method of treating or preventing liver disease in a human comprising: administering a compound of formula III in an amount and for a time effective to treat or prevent liver disease in a human in need thereof.

The liver disease treated may be a chronic liver disease, such as liver fibrosis, cirrhosis, hepatitis, or more specifically hepatitis c.

In other embodiments, the liver disease is acute liver disease. The acute liver disease may be hepatitis or more specifically hepatitis a or hepatitis b.

Another embodiment provides a method of reducing hunger in a human comprising: administering JWH-073-M4 in an amount and for a time effective to reduce hunger in a human in need thereof.

Another embodiment provides a method of reducing hunger in a human comprising: administering a compound of formula III in an amount and for a time effective to reduce hunger in a human in need thereof.

Another embodiment provides a method of treating insulin resistance in a human comprising: administering JWH-073-

M4 in an amount and for a time effective to treat insulin resistance in a human in need thereof.

Another embodiment provides a method of treating insulin resistance in a human comprising: administering a compound of formula III in an amount and for a time effective to treat insulin resistance in a human in need thereof.

Another embodiment provides a method of screening for an agent effective to treat or prevent obesity or an obesity related condition in a human comprising: testing an agent in an animal model of obesity or an obesity related condition to determine if the agent is effective to treat or prevent obesity or an obesity related condition in the animal model; wherein the obesity related condition is selected from the group consisting of insulin resistance, atherosclerosis, NASH, low-levels of high-density lipoprotein cholesterol, excessive hunger; wherein the agent is a compound of formula I:

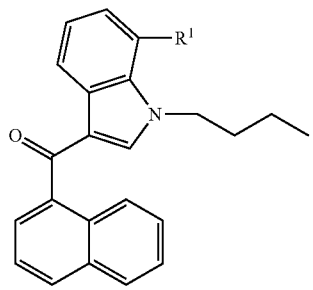

where $R^1$ is selected from the group consisting of chloro, fluoro, —CH$_3$OH, —CH$_2$O, and —CH$_2$CH$_2$OH;

or wherein the agent is a compound of formula II:

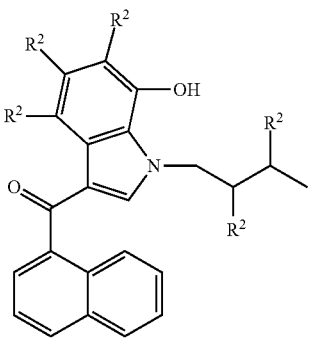

where one of the $R^2$s is Cl, F, hydroxy, methyl, or hydroxymethyl, and the other $R^2$s are H.

In a more specific embodiment, the method of screening further comprises testing the agent in an in vitro test to determine if the agent is a CB1R neutral antagonist.

In another embodiment, the method of screening further comprises testing the agent in an in vivo test to determine if the agent a peripherally restricted CB1R neutral antagonist.

Another embodiment of the method of screening further comprises testing the agent to determine if the agent is a CB2R agonist or partial agonist.

Another embodiment provides a method of screening for an agent effective to treat or prevent liver disease in a human comprising: testing an agent in an animal model of liver disease to determine if the agent is effective to treat or prevent liver disease in the animal model; wherein the agent is a compound of formula I:

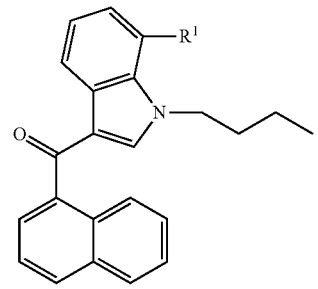

where $R^1$ is selected from the group consisting of chloro, fluoro, —CH$_3$OH, —CH$_2$O, and —CH$_2$CH$_2$OH;

or wherein the agent is a compound of formula II:

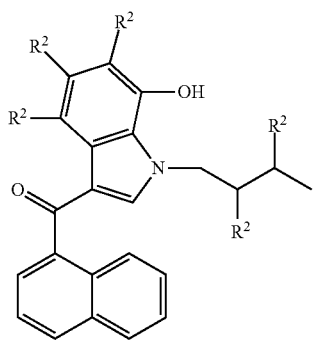

where one of the $R^2$s is Cl, F, hydroxy, methyl, and hydroxymethyl, and the other $R^2$s are H.

The method may further comprise testing the agent in an in vitro test to determine if the agent is a CB1R neutral antagonist.

In a more specific embodiment, the method further comprises testing the agent in an in vivo test to determine if the agent is a peripherally restricted CB1R neutral antagonist.

In another embodiment, the method further comprises testing the agent to determine if the agent is a CB2R agonist or partial agonist.

In a more specific embodiment, the liver disease is chronic liver disease.

Other embodiments provide a method of screening for an agent effective to treat alcoholism or drug abuse in a human comprising: testing an agent in an animal model of alcoholism or drug abuse to determine if the agent is effective to treat alcoholism or drug abuse in the animal model; wherein the agent is a compound of formula I:

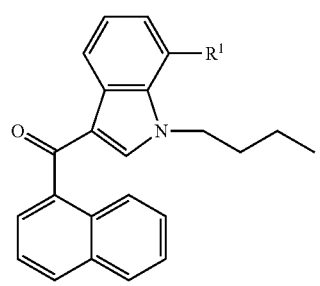

where $R^1$ is selected from the group consisting of chloro, fluoro, —CH$_3$OH, —CH$_2$O, and —CH$_2$CH$_2$OH;

or wherein the agent is a compound of formula II:

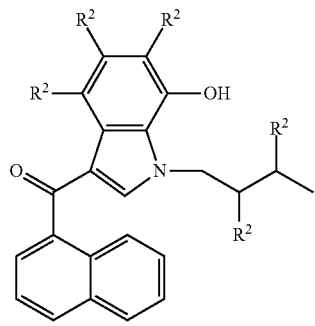

where one of the R²s is Cl, F, hydroxy, methyl, and hydroxymethyl, and the other R²s are H.

EXAMPLES

Example 1

Abstract

K2 and several similar purported "incense products" spiked with synthetic cannabinoids are abused as *cannabis* substitutes. We hypothesized that metabolism of JWH-073, a prevalent cannabinoid found in K2, contributes to toxicity associated with K2 use. Competition receptor binding studies and G-protein activation assays, both performed by employing mouse brain homogenates, were used to determine the affinity and intrinsic activity, respectively, of potential monohydroxylated (M1, M3-M5) and monocarboxylated (M6) metabolites at cannabinoid 1 receptors (CB1Rs). Surprisingly, M1, M4, and M5 retain nanomolar affinity for CB1Rs, while M3 displays micromolar affinity and M6 does not bind to CB1Rs. JWH-073 displays equivalent efficacy to that of the CB1R full agonist CP-55,940, while M1, M3, and M5 act as CB1R partial agonists, and M4 shows little or no intrinsic activity. Further in vitro investigation by Schild analysis revealed that M4 acts as a competitive neutral CB1R antagonist ($K_b$~40 nM). In agreement with in vitro studies, M4 also demonstrates CB1R antagonism in vivo by blunting cannabinoid-induced hypothermia in mice. Interestingly, M4 does not block agonist-mediated responses of other measures in the cannabinoid tetrad (e.g., locomotor suppression, catalepsy or analgesia). Finally, also as predicted by in vitro results, M1 exhibits agonist activity in vivo by inducing significant hypothermia and suppression of locomotor activity in mice.

In conclusion, the present study indicates that further work examining the physiological effects of synthetic cannabinoid metabolism is warranted. Such a complex mix of metabolically produced CB1R ligands may contribute to the adverse effect profile of JWH-073-containing products.

1. Introduction

Figure 2:
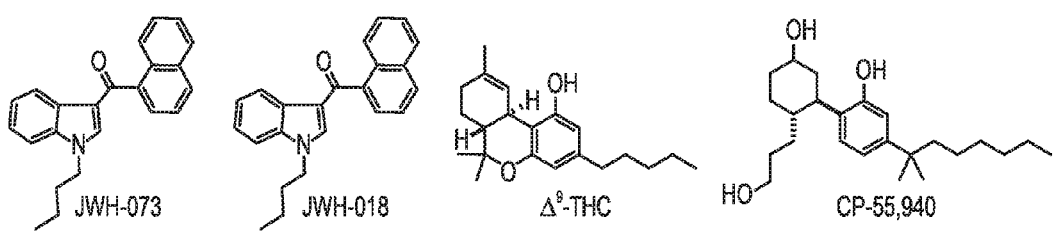
FIG. 2. Cannabinoids examined in the present study. A. Structures of significant cannabinoids discussed and utilized in the present work. B. Structures of JWH-073 [(1-butyl-1H-indole-3-yl)-1-naphthalenyl-methanone] and its potential metabolites, here designated M1 [(1-butyl-4-hydroxy-1H-indole-3-yl)(naphthalen-1-yl-methanone], M3 [(1-butyl-6-hydroxy-1H-indole-3-yl)(naphthalen-1-yl-methanone], M4 [(1-butyl-7-hydroxy-1H-indole-3-yl)(naphthalen-1-yl-methanone], M5 [(1-(4-hydroxybutyl-1H-indole-3-yl)(naphthalen-1-yl)-methanone] and M6 ([4-(3-(1-naphthoyl)-1H-indole-1-yl)-1-butanoic acid]), examined for CB1R affinity and activity.
Figure 2:
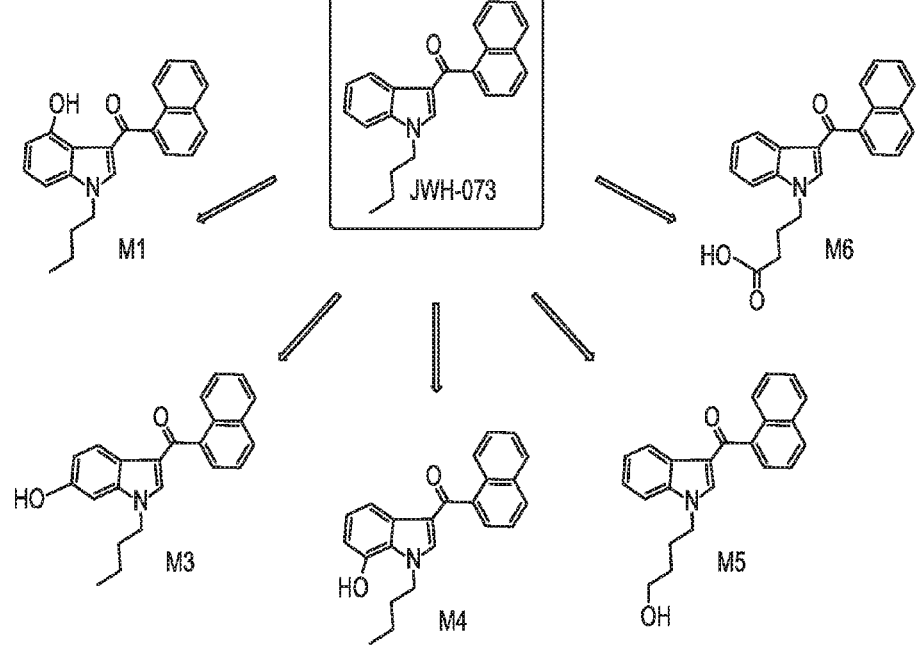
Figure 3:
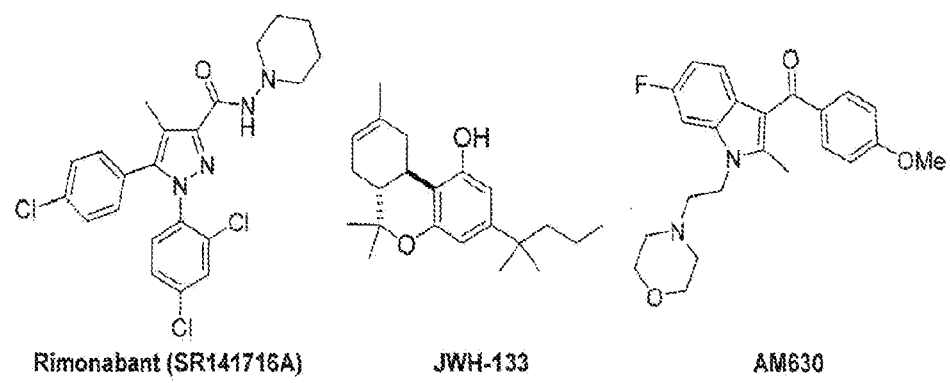
FIG. 3. Structures of rimonabant (CB1R antagonist/inverse agonist), JWH-133 (B2R agonist), and AM630 (CB2R antagonist).

K2, Spice and a variety of similar "incense products" (hereafter referred to collectively as "K2") are currently emerging drugs of abuse with psychotropic effects mimicking those of marijuana [5-7]. K2 is made by adulterating plant matter with any of several diverse mixtures of synthetic cannabinoids, which are molecules that act in the brain similarly to $\Delta^9$-tetrahydrocannabinol ($\Delta^9$-THC), the major psychoactive molecule present in marijuana. Many of the most prevalent of these synthetic cannabinoids are structurally distinct relative to $\Delta^9$-THC (FIGS. 2A and B) and individual K2 products are often quite variable in composition and unpredictable in content. For example, one study details the analytical detection of 11 different synthetic cannabinoids across 40 batches of 16 different incense products in various combinations and proportions from brand to brand and from batch to batch, even within brands [8]. Many K2 components were previously unregulated by legislative authorities in the U.S., and K2 use is undetectable by standard drug urine tests. Reportedly, these properties contribute to the motivation for K2 use by individuals seeking to attain the mood-altering effects of *cannabis*, while evading detection, prosecution and potential incarceration [9]. Compared to marijuana, K2 use is associated with an apparently higher prevalence of severe adverse effects, such as hypertension, tachycardia, hallucinations, agitation, seizures and panic attacks that often require immediate medical care [10-16]. The American Association of Poison Control Centers (AAPCC) reported handling 2,874 calls in the year 2010 regarding toxicities experienced by individuals after using K2 [17]. Data and reports such as these prompted the United States Drug Enforcement Administration (USDEA) to temporarily classify five common K2 synthetic cannabinoids (JWH-018, JWH-073, JWH-200, CP-47, 497, and cannabicyclohexanol) as Schedule I substances on Mar. 1, 2011, until greater understanding regarding the health consequences of their use can be established [18]. Despite this ban, as of Nov. 30, 2011, a reported 6,348 calls regarding K2 use have been made to the AAPCC in 2011 alone [19], which is more than double the 2010 report, indicating an apparent persistence of K2 use that results in adverse effects [9, 20]. All of these data are particularly alarming given the recent finding that one in nine high school seniors admitted to using K2 over the past year, making K2 the second most frequently used illicit drug, after marijuana, among high school seniors [21]

Synthetic cannabinoids found in K2, as well as $\Delta^9$-THC and other cannabinoids, induce psychotropic effects by binding and activating cannabinoid 1 receptors (CB1Rs) in the CNS [22, 23]. CB1Rs are G-protein coupled receptors (GPCRs) found in highest abundance in the brain, and in lesser amounts in the liver [24], muscle and adipose tissues [25], gastrointestinal tract [26], bone [27], and reproductive system [28]. Most scientific data available regarding K2 to date has focused on determining product composition [8, 29], detecting useful biomarkers for compound detection in urine and serum [30-32], and reporting commonly observed adverse clinical effects [14, 15]. However, there is a general lack of knowledge concerning K2 metabolism, pharmacology and toxicology.

One synthetic cannabinoid often present in K2 is JWH-073 [29, 33, 34]. JWH-073 is a member of the JWH aminoalkylindole family, which was originally synthesized to study the endocannabinoid system [35]. "Co-abuse" of JWH-073 with JWH-018 (a commonly abused CB1R full agonist that is structurally similar to JWH-073) has been anecdotally reported to reduce JWH-018-induced anxiety, resulting in a more "mellow", *cannabis*-like high compared to use of JWH-018 alone [36].

Although little is known concerning the biotransformation of the synthetic cannabinoids present in K2, initial studies have demonstrated that several Phase I monohydroxylated and carboxylated metabolites of both JWH-018 and JWH-073 are the major metabolites excreted in the urine of K2 users [30-32, 37, 38]. Recently, our laboratory reported that several monohydroxylated JWH-018 metabolites unexpectedly retain high affinity and intrinsic activity at CB1Rs [39], leading us to suggest that these and/or additional active metabolites likely contribute to the mechanism of K2 toxicity. Here, we hypothesize that biotransformation of JWH-073 produces similar metabolites (FIG. 2) possessing high affinity and/or activity at CB1Rs, resulting in complex interactions with other synthetic cannabinoids and their metabolites present in K2. The combined action of all active synthetic cannabinoids formed likely produces an "entourage effect" that contributes to the increased incidence of severe adverse effects observed with K2 relative to marijuana use. Therefore, we first examined the in vitro affinity and activity of one carboxylated and four monohydroxylated derivatives of JWH-073 at CB1Rs. These initial findings led us to further characterize the in vitro and in vivo pharmacology of two molecules, M1 and M4, for potential actions as a CB1R agonist and antagonist, respectively.

2. Methods 2.1. Materials

All compounds were stored at −20° C., thawed and diluted in vehicle for use in subsequent experiments. JWH-073, M1, M3-M6 (FIG. 2) were purchased from Cayman Chemical (Ann Arbor, Mich.), and diluted to a stock solution with a final concentration of either $10^{-2}$ M (for [$^{35}$S]GTPγS binding assays) or $10^{-3}$ M (for competition receptor binding) in 100% ethanol. JWH-018 was synthesized as previously described [40-42] and validated by [$^1$H] Nuclear Magnetic Resonance (NMR), [$^{13}$C] NMR, Distortionless Enhancement by Polarization Transfer (DEPT)-135, Heteronuclear Single Quantum Correlation (HSQC) spectrometry, and mass spectrometry (MS). JWH-018 was diluted to a stock solution of $10^{-2}$ M with 100% ethanol. $\Delta^9$-THC was supplied by the National Institute on Drug Abuse (NIDA, Bethesda, Md.). WIN-55, 212-2, CP-55,940, AM251, and O-2050 were purchased from Tocris Bioscience (Ellisville, Mo.), and SR141716 (Rimonabant) was purchased from Cayman Chemical. AM251, O-2050, and Rimonabant were diluted to $10^{-2}$ M with dimethyl sulfoxide (DMSO), while $\Delta^9$-THC and CP-55,940 were diluted to $10^{-2}$ M and WIN-55, 212-2 to $10^{-3}$ M in 100% ethanol. GTPγS and GDP used in the [$^{35}$S]GTPγS assay were purchased from EMD Chemical (Gibbstown, N.J.) and Sigma Aldrich (St. Louis, Mo.), respectively, and dissolved in water to a stock concentration of $10^{-2}$ M. Adenosine deaminase from bovine spleen (Type IX, ammonium sulfate suspension) was purchased from Sigma Aldrich (St. Louis, Mo.), and diluted in 20 mM HEPES buffer to 100 units/mL. [$^3$H]CP-55,940 (144.0 Ci/mmol) was purchased from Perkin Elmer (Waltham, Mass.) and [$^{35}$S]GTPγS (1250 Ci/mmol) was purchased from American Radiolabeled Chemicals (St. Louis, Mo.). For all in vivo studies, cannabinoids were dissolved and administered in a vehicle consisting of a 1:1:18 ratio of absolute ethanol:emulphor:physiological saline, and injected in a volume equal to 10 mL/kg.

2.2. Membrane Preparation

Mouse brain homogenates for in vitro assays were prepared as previously described [43]. Briefly, whole brains were harvested from B6SJL mice, snap-frozen in liquid nitrogen and stored at −80° C. On the day membrane homogenates were to be prepared, brains were thawed on ice, then pooled in a 40 mL Dounce glass homogenizer and suspended in 5 volumes of ice cold homogenization buffer (50 mM HEPES, pH 7.4, 3 mM $MgCl_2$, and 1 mM EGTA). Brains were then subjected to 10 complete strokes with an A pestle, followed by centrifugation at 40,000×g for 10 minutes at +4° C. Resulting supernatants were discarded, and the pellet was resuspended, homogenized and centrifuged similarly twice more, with supernatants being discarded. For the final resuspension and homogenization with a B pestle, ice-cold 50 mM HEPES was used in place of homogenization buffer, and homogenates were aliquoted and stored at −80° C. Protein concentrations of homogenates were determined using the BCA™ Protein Assay (Thermo Scientific, Rockford, Ill.).

2.3. Competition Receptor Binding Assay

Competition receptor binding was performed as previously described [44]. Briefly, 50 μg of mouse brain homogenates were incubated for 90 minutes to attain equilibrium binding at room temperature with 0.2 nM [$^3$H]CP-55,940, 5 mM $MgCl_2$, and either increasing cannabinoid concentrations (0.1 nM to 10 μM), 10 μM WIN-55,212-2 (for non-specific binding) or vehicle (for total binding), in triplicate, in a volume of 1 mL of buffer containing 50 mM Tris, 0.05% bovine serum albumin (BSA) and 1% ethanol vehicle. Reactions were terminated by rapid vacuum filtration through Whatman GF/B glass fiber filters, followed by five washes with ice-cold buffer (50 mM Tris, 0.05% BSA). Filters were immediately placed into 7 mL scintillation vials to which 4 mL of ScintiVerse™ BD Cocktail scintillation fluid (Fisher Scientific, Fair Lawn, N.J.) was added. Bound radioactivity was determined after overnight incubation at room temperature and shaking, by liquid scintillation spectrophotometry with an efficiency of 44% (Tri Carb 2100 TR Liquid Scintillation Analyzer, Packard Instrument Company, Meriden, Conn.). Specific binding is expressed as total binding minus non-specific binding, and is graphed for each data point as a percentage of specific binding occurring in the absence of any competitor.

2.4. [$^{35}$S]GTPγS Binding Assay

[$^{35}$S]GTPγS binding was performed as previously described [39]. Briefly, 25 μg of mouse brain homogenates were incubated for 30 minutes at 30° C. with 0.1 nM [$^{35}$S] GTPγS, 10 μM GDP, and either cannabinoid+/−antagonist, 10 μM unlabeled GTPγS (non-specific binding) or vehicle (total binding), in triplicate, in a volume of 1 mL of buffer containing 20 mM HEPES, 10 mM $MgCl_2$, 100 mM NaCl, 20 units/L adenosine deaminase, 0.05% BSA and the appropriate DMSO (0.1%) and/or ethanol (<0.2%) vehicle. Assay buffer containing 100 mM KCl, instead of 100 mM NaCl, was used to increase basal G-protein activity in experiments examining inverse agonism. Reactions were terminated by quick vacuum filtration through Whatman GF/B glass fiber filters, followed by five washes with ice-cold buffer (20 mM HEPES, 0.05% BSA). Filters were immediately placed into 7 mL scintillation vials to which 4 mL of ScintiVerse™ BD Cocktail scintillation fluid was added. Bound radioactivity was determined after overnight incubation at room temperature and shaking by liquid scintillation spectrophotometry with an efficiency of 93% (Tri Carb 2100 TR Liquid Scintillation Analyzer, Packard Instrument Company, Meriden, Conn.). Specific binding is expressed as picomoles of [$^{35}$S] GTPγS bound per mg of protein.

2.5. Animal Care and Use

All studies were carried out in accordance with the Declaration of Helsinki and with the Guide for Care and Use of Laboratory Animals as adopted and promulgated by the National Institutes of Health. Experimental protocols were approved by the Animal Care and Use Committee at the University of Arkansas for Medical Sciences (Animal Use Protocol #3155).

Prior to surgery (see below), male NIH Swiss mice (Harlan Sprague Dawley Inc., Indianapolis, Ind.), weighing approximately 25-30 g, were housed 3 animals per Plexiglas® cage (15.24×25.40×12.70 cm) in a temperature-controlled room in an Association for Assessment and Accreditation of Laboratory Animal Care (AAALAC) accredited animal facility at the University of Arkansas for Medical Sciences. Room conditions were maintained at 22±2° C. and 45-50% humidity.

Lights were set to a 12-h light/dark cycle. Animals were fed Lab Diet rodent chow (Laboratory Rodent Diet #5001, PMI Feeds, Inc., St. Louis, Mo.) and water ad libitum throughout testing Animals were acclimated to the laboratory environment for ~7 days prior to experiments, and to the biotelemetry chambers for at least 2 hours prior to initiation of data acquisition. All test conditions used groups of 5 or 6 mice, and all mice were drug-naïve (with the exception of surgical anesthetics) prior to testing.

2.6. Cannabinoid Tetrad

Cannabinoid effects on core temperature and locomotor activity were measured using surgically-implanted biotelemetry probes. Following appropriate anesthetization with ketamine (100 mg/kg, intraperitoneal [i.p.]) and xylazine (10 mg/kg, i.p.), the abdominal area of each mouse was shaved and sanitized with iodine swabs. A rostral-caudal cut approximately 1.5 cm in length was made with skin scissors, providing access to the intraperitoneal cavity. A cylindrical glass-encapsulated radiotelemetry probe (model ER-4000 E-Mitter, Mini Mitter Co., Inc., Bend, Oreg.) was then inserted, and the incision was closed using absorbable 5-0 chromic gut suture material. At least 7 days were imposed between surgery and experimental observation of cannabinoid effects to allow incisions to heal and mice to recover normal body weights. Following surgery, implanted mice were individually housed in Plexiglas® mouse cages (15.24× 25.40×12.70 cm) for the duration of all temperature and locomotor activity experiments Implanted transmitters produced activity- and temperature-modulated signals that were transmitted to a receiver (model ER-4000 Receiver, Mini Mitter Co., Inc., Bend, Oreg.) underneath each mouse cage. Receivers were housed in light- and sound-attenuating cubicles (Med Associates model ENV-022MD, St. Albans, Vt.) equipped with exhaust fans, which further masked ambient laboratory noise. On experimental days, mice were weighed, marked, and returned to their individual cages during which at least 1 hr of baseline data were collected. Cannabinoid doses were then calculated and prepared for injection Animals were subsequently removed from their cage and administered an intraperitoneal (i.p.,) injection with the indicated doses of JWH-018, JWH-073, M1, M4, JWH-018 plus M4, or an equivalent volume of vehicle. Mice were then placed into a new cage with fresh bedding to stimulate exploratory behavior. Temperature and locomotor activity data were collected at regular 5-min intervals and processed simultaneously by the Vital View data acquisition system (Mini Mitter Co., Inc., Bend, Oreg.) for at least 10 hrs.

Analgesia was measured as tail-flick latency using the EMDIE-TF6 radiant heat apparatus (Emdie Instrument Co., Montpelier, Va.). For each trial, mice were positioned on the stage of apparatus, while the tail was extended into a groove to break a photobeam. Beginning at t=0, a button was depressed to begin a timer and illuminate a radiant heat source directed onto the dorsal surface of the tail, approximately 2 cm from its origin from the body. Movement of the tail at any point after the beginning of the trial broke the photobeam, stopped both the heat source and the timer, and ended the trial. One trial per mouse per time point was performed. Sensitivity and light intensity were set at 150 and 369, respectively (calibrated to produce a tail flick latency between 2 and 4 seconds for untreated mice), and maximum time for each trial was 10 seconds. Tail-flick latency was measured at 0, 10, 30, and 60 minutes after either cannabinoid or vehicle administration.

Catalepsy was measured by the horizontal bar test, which utilized a cylindrical steel bar (0.5 cm in diameter) that was suspended 4.0 cm above and horizontal to a Plexiglas platform. To begin the test trial, a mouse was positioned with its forelimbs on the horizontal bar and its hindlimbs on the platform, in such a way that the mouse assumed a rearing posture. Upon placement on the catalepsy bar, a timer was started, and counted until the mouse removed both of its paws from the bar and assumed a non-rearing posture. A single trial per mouse per time point was performed, and the maximum time allowed on the bar was 30 seconds. Catalepsy scores were measured at 0, 10, 30 and 60 minutes after administration of vehicle or cannabinoid.

2.7. Statistical Analysis

Curve fitting and statistical analyses for in vitro experiments were performed using GraphPad Prism™ version 5.0b (GraphPad Software Inc., San Diego, Calif.). The Cheng-Prusoff equation [45] was used to convert the experimental $IC_{50}$ values obtained from competition receptor binding experiments to $K_i$ values, a quantitative measure of receptor affinity. Non-linear regression for one-site competition was used to determine the $IC_{50}$ for competition receptor binding. Curve fitting of concentration-effect curves via non-linear regression was also employed to determine the $EC_{50}$ (a measure of potency) and $E_{max}$ (a measure of efficacy) for $[^{35}S]$ GTPγS concentration-effects experiments. A power equation based on the Cheng-Prusoff equation was used to determine the $K_b$ of M4 from its $IC_{50}$ to inhibit an $EC_{90}$ concentration of CP-55,940 [46]. Schild analysis as previously described by Thomas, et. al. [47] was also performed to determine $K_b$ and Schild slope for the ability of M4 to shift the JWH-018 concentration effect curves for G-protein activation. Data are expressed as mean±SEM. The Student's t-test was used to determine statistical significance (P<0.05) between two groups, while a one-way ANOVA, followed by Tukey's Multiple Comparison post-hoc test, was used to determine statistical significance (P<0.05) between three or more groups.

For core body temperature experiments, the area under the curve (AUC) was calculated using a trapezoidal rule from 0-500 minutes, and statistical significance (P<0.05) was determined using a one-way ANOVA, followed by Tukey's HSD post-hoc test. For locomotor activity, total locomotor counts were summed from 0-800 minutes. Because locomotor, analgesia and catalepsy data were not normally distributed, Kruskal-Wallis one-way ANOVA on ranks were performed, and all pair-wise comparisons were then made using the Tukey's HSD tests. In vivo statistical calculations were performed using SigmaStat 3 (Systat Software, Inc., San Jose, Calif.).

3. Results 3.1. JWH-073, M1, M4, and 115 Bind to CB1Rs with Intermediate to High Affinity.

Figure 4:
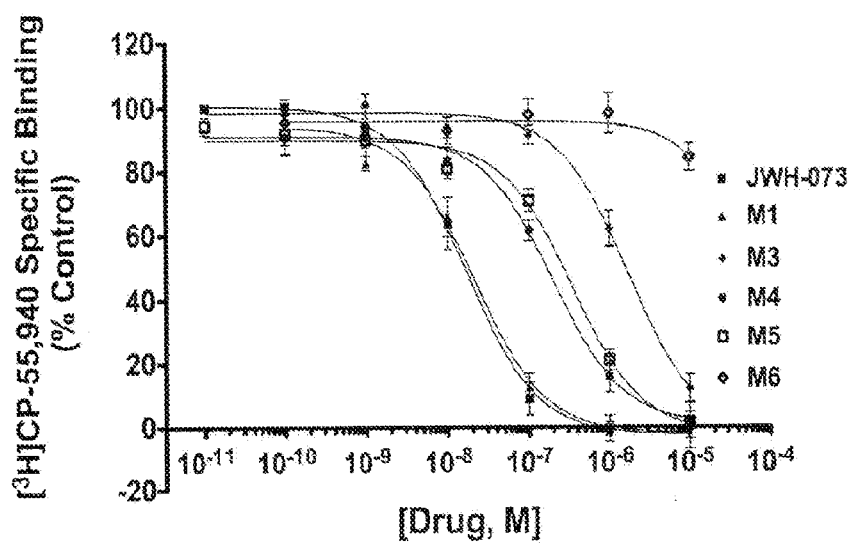
FIG. 4. JWH-073, M1, M3, M4, M5, but not M6, bind to CB1R receptors. In competition receptor binding assays, JWH-073, M1, M3, M4, and M5 completely displaced [$^3$H] CP-55,940 from CB1Rs in mouse brain homogenates with nanomolar (JWH-073, M1, M4, M5) to micromolar (M3) affinity, while M6 displaced less than 10% [$^3$H]CP-55,940 specific binding, signifying M6 has little or no CB1R affinity (n=3-6).

Saturation binding experiments using the radiolabeled, high-affinity cannabinoid agonist $[^3H]CP$-55,940 determined that mouse brain homogenates employed for these experiments contain a CB1R density of 2.44±0.15 pmol/mg protein, to which $[^3H]CP$-55,940 binds with a $K_d$ of 0.37±0.07 nM (n=3). To determine the affinity ($K_i$) of JWH-073, M1, and M3-M6 (FIG. 2) for CB1Rs, initial competition receptor binding studies with $[^3H]CP$-55,940 were conducted (FIG. 4, Table 1). Specifically, the ability of increasing concentrations of each compound to displace $[^3H]CP$-55,940 from CB1Rs present in mouse brain homogenates was examined. In agreement with previous reports [48], JWH-073 bound to CB1Rs with high affinity (12.9±3.4 nM, n=6, Table 1). Interestingly, M1 also displayed remarkably high affinity for CB1Rs, equivalent to that of the parent compound (14.1±3.5 nM, n=3). The affinities of M4 and M5 for CB1Rs were slightly lower, but still in the intermediate nanomolar range (122.2±16.2 nM and 224.2±9.0 nM, respectively, n=3-4), predicting that even if relatively low concentrations of these compounds are formed via metabolism, they likely produce physiologically relevant effects via binding and modulation of CB1R activity in vivo. M3 bound to CB1Rs with a low micromolar affinity ($1.28\pm0.47$ μM, n=4), while concentrations of M6 as high as 10 μM produced less than 10% displacement of [$^3$H]CP-55,940 specific binding (n=3), signifying little or no CB1R affinity.

TABLE 1

Comparison of CB1R affinity with potency and efficacy for G-protein activation produced by cannabinoid ligands

| | [$^3$H]CP binding | [$^{35}$S]GTPγS Binding | |
|---|---|---|---|
| Drug | $K_i$ (nM) | $EC_{50}$ (nM) | $E_{max}$ (pmole/mg) |
| CP-55,940 | $0.26 \pm 0.1$[†] | $7.5 \pm 1.8$ | $0.26 \pm 0.01^a$ |
| JWH-073 | $12.9 \pm 3.4$ | $276.5 \pm 65.3$ | $0.27 \pm 0.01^a$ |
| M1 | $14.1 \pm 3.5$ | $112.9 \pm 29.2$ | $0.14 \pm 0.01^b$ |
| Δ$^9$-THC | $15.3 \pm 4.5$[†] | $77.0 \pm 29.9$ | $0.08 \pm 0.01^c$ |

[†]Values previously reported [39]
[a,b,c]Values designated by different letters are significantly different.
P < 0.05, one-way ANOVA, Tukey Post-hoc test; Reported as mean ± SEM, n = 3-4

3.2. M1, M3 and M5 Act as CB1R Partial Agonists with Equivalent Efficacy to Stimulate G-Protein Activity, while M4 Lacks Intrinsic Activity.

The intrinsic activity of JWH-073, M1, and M3-M6 at CB1Rs was next determined by employing the [$^{35}$S]GTPγS binding assay, which measures G-protein activation, in mouse brain homogenates. Initially, the G-protein activation induced by a receptor-saturating concentration (10 μM) of each compound was examined (FIG. 5A, Table 2). JWH-073 displayed equivalent efficacy relative to the full CB1R agonist, CP-55,940 ($0.28\pm0.03$ vs. $0.32\pm0.02$ pmole/mg, respectively, n=3-5). M1, M3 and M5 surprisingly retained partial agonist activity ($0.14\pm0.01$, $0.11\pm0.02$, and $0.16\pm0.02$ pmole/mg, respectively, n=3-4), producing greater than or equivalent activation of G-proteins relative to that produced by Δ$^9$-THC ($0.08\pm0.00$ pmole/mg). In contrast, M4 and M6 produced negligible G-protein activation in mouse brain homogenates. Interestingly, 10 μM THC (FIG. 5A) produces less G-protein activation than a 1 μM concentration (FIG. 5B). These data parallel our observations that in this assay, under these experimental conditions, THC consistently exhibits a bi-phasic concentration-effect curve with concentrations greater than 1 μM producing less activation than lower concentrations examined (see FIG. 6).

TABLE 2

G-protein activation by JWH-073 and metabolites, and blockade by the selective CB1R antagonist O-2050

| | [$^{35}$S]GTPγS Binding (pmole/mg) | | | |
|---|---|---|---|---|
| Drug | 10 μM | 1 μM | 100 nM | +O-2050 (1 μM)[†] |
| Δ$^9$-THC | $0.08 \pm 0.00^{a,b,}$ | $0.17 \pm 0.01$ | ND | $0.06 \pm 0.01$*** |
| CP-55,940[††] | $0.32 \pm 0.02^{c,}$ | ND | $0.20 \pm 0.04$ | $0.06 \pm 0.03$** |
| JWH-073 | $0.28 \pm 0.03^c$ | $0.27 \pm 0.04$ | ND | $0.07 \pm 0.02$** |
| M1 | $0.14 \pm 0.01^a$ | $0.17 \pm 0.01$ | ND | $0.07 \pm 0.01$** |
| M3 | $0.11 \pm 0.02^{a,b}$ | $0.04 \pm 0.00$ | ND | $0.02 \pm 0.01$* |
| M4 | $0.04 \pm 0.01^b$ | ND | ND | ND |
| M5 | $0.16 \pm 0.02^a$ | $0.12 \pm 0.00$ | ND | $0.05 \pm 0.01$*** |
| M6 | $0.03 \pm 0.01^b$ | ND | ND | ND |

[a,b,c]Values designated by different letters are significantly different.
P < 0.05, one-way ANOVA with Tukey's post-hoc test, reported as mean ± SEM, n = 3-8;
[†]$E_{max}$ of O-2050 alone (1 μM) = $0.05 \pm 0.01$
[††]Due to its high affinity, 100 nM of CP-55,940 was used instead of 1 μM;
*P < 0.05;
**P < 0.01;
***P < 0.001, vs. drug alone, Student's t-test, reported as mean ± SEM, n = 3-9.
ND, Not Determined To confirm that CP-55,940, JWH-073, M1, M3 and M5 produced G-protein activation via specific interaction with CB1Rs, the effect of co-administration with a CB1R-selective neutral antagonist O-2050 (1 μM) to attenuate $EC_{90}$ concentrations (1 μM for all compounds except CP-55,940, which instead was 100 nM) of the cannabinoids was examined (FIG. 5B, Table 2). The increase in [$^{35}$S]GTPγS binding produced by each of these agonists was significantly reduced by O-2050, indicating that these compounds all activated G-proteins in mouse brain homogenates by a CB1R-dependent mechanism.

Figure 5:
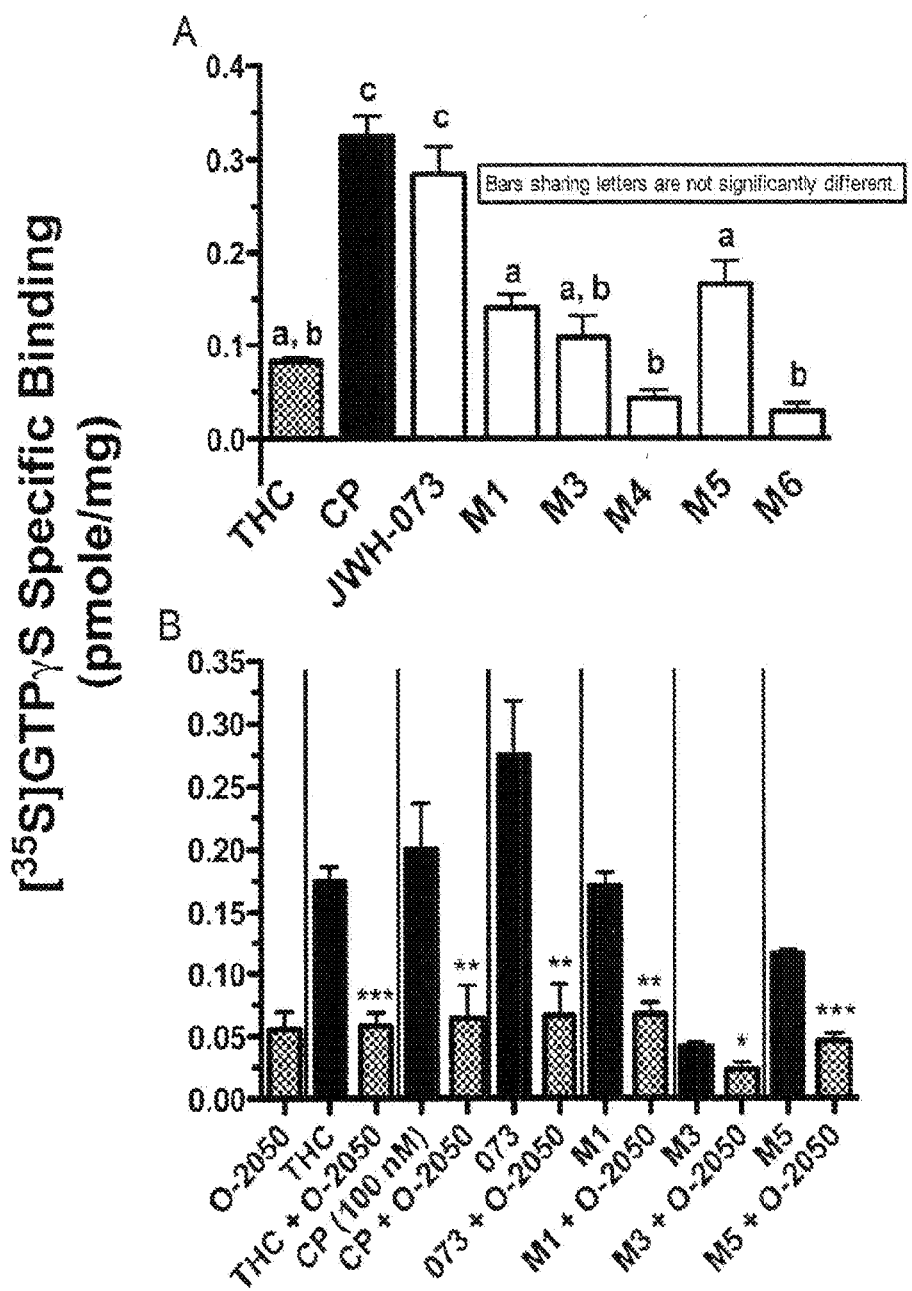
FIG. 5. JWH-073, M1, M3 and M5, but not M4, activate CB1Rs in mouse brain homogenates. A. A receptor-saturating concentration (10 μM) of JWH-073 in the [$^{35}$S]GTPγS binding assay activated G-proteins in mouse brain homogenates with full agonist activity equivalent to that produced by CP-55,940. M1, M3 and M5, but not M4 or M6, activate G-proteins with efficacy equivalent to that produced by Δ$^9$-THC. Values designated by different letters are significantly different (P<0.05, one way ANOVA with Tukey's Multiple Comparison post-hoc test, mean±SEM, n=3-8). B. Activation of G-proteins in mouse brain homogenates by JWH-073, M1, M3, and M5 (1 μM, solid bars) was significantly attenuated by co-incubation with the CB1R-selective antagonist O-2050 (1 μM, checkered bars), signifying that JWH-073, M1, M3 and M5 activate G-proteins via CB1Rs. (*P<0.05, P<0.01, *P<0.001 vs. cannabinoid alone, Student's t-test, mean±SEM, n=3-6) Note: Because of its higher CB1R affinity, 100 nM, instead of 1 μM, of CP-55,940 was used in the CB1R blockade assay.
Figure 6:
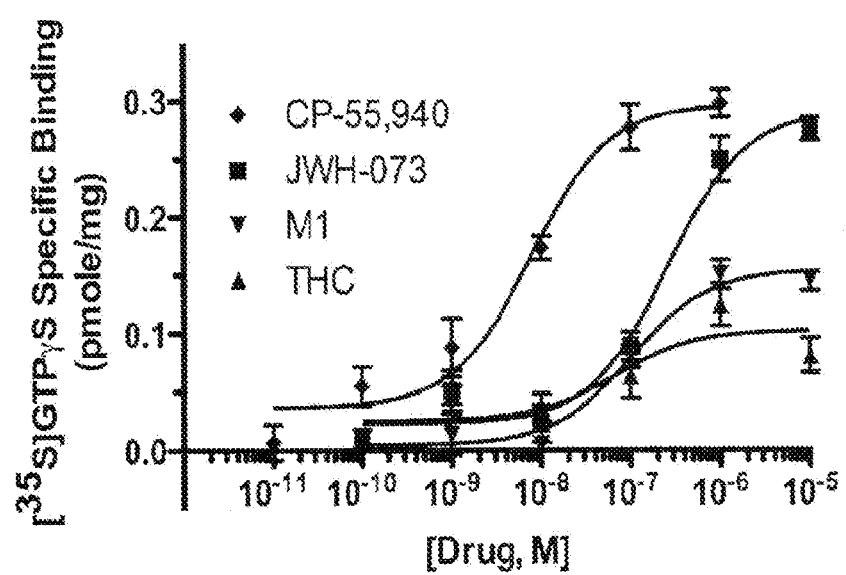
FIG. 6. G-protein activation by JWH-073 and M1 via CB1Rs is concentration-dependent. The potency and maximal efficacy of CP-55,940, JWH-073, M1, and Δ$^9$-THC to activate CB in mouse brain homogenates were determined employing the [$^{35}$S]GTPγS binding assay (mean±SEM, n=3-4).

Concentration-effect studies were conducted to determine a measure of potency (e.g., $EC_{50}$) for G-protein activation by M1 and to further validate a receptor-mediated mechanism for the intrinsic activity reported (FIG. 6, Table 1). As anticipated, G-protein activation produced by CP-55,940, JWH-073, Δ$^9$-THC and M1 was concentration-dependent, with maximal efficacies (e.g., $E_{max}$ values) that agree well with data presented in FIG. 5A. Collectively, these data indicate that CP-55,940 and JWH-073 act as full CB1R agonists, while M1, M3 and M5 exhibit partial agonist activity, and M4 lacks significant intrinsic activity at CB1Rs.

3.3. M4 Acts as an In Vitro Competitive Neutral Antagonist at CB1Rs with Nanomolar Potency ($K_b$).

Figure 7:
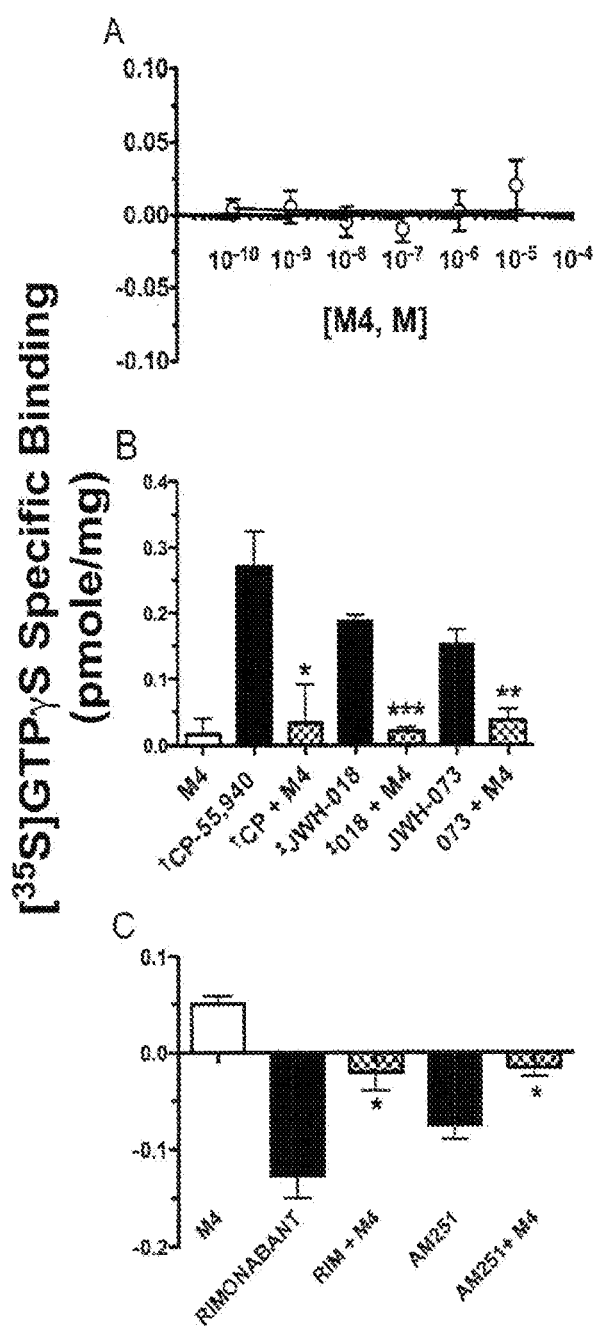
FIG. 7. M4 antagonizes the actions of both CB1R agonists and inverse agonists in mouse brain homogenates, while having no activity when tested alone. A. In the [$^{35}$S]GTPγS binding assay, M4 when examined alone, up to 10 μM concentrations, showed neither agonist nor inverse agonist activity in mouse brain homogenates. B. M4 (10 μM) blocked the activity produced by CB1R agonists (100 nM CP, 1 μM JWH-018, and 500 nM JWH-073) and C. inverse agonists (10 μM Rimonabant and AM251) (*P<0.05, P<0.01, *P<0.001 vs. cannabinoid alone, Student's t-test, mean±SEM, n=3-6; †, ‡ These data are of the same data presented in FIGS. 6A[†] and 6B[‡].)
Figure 8:
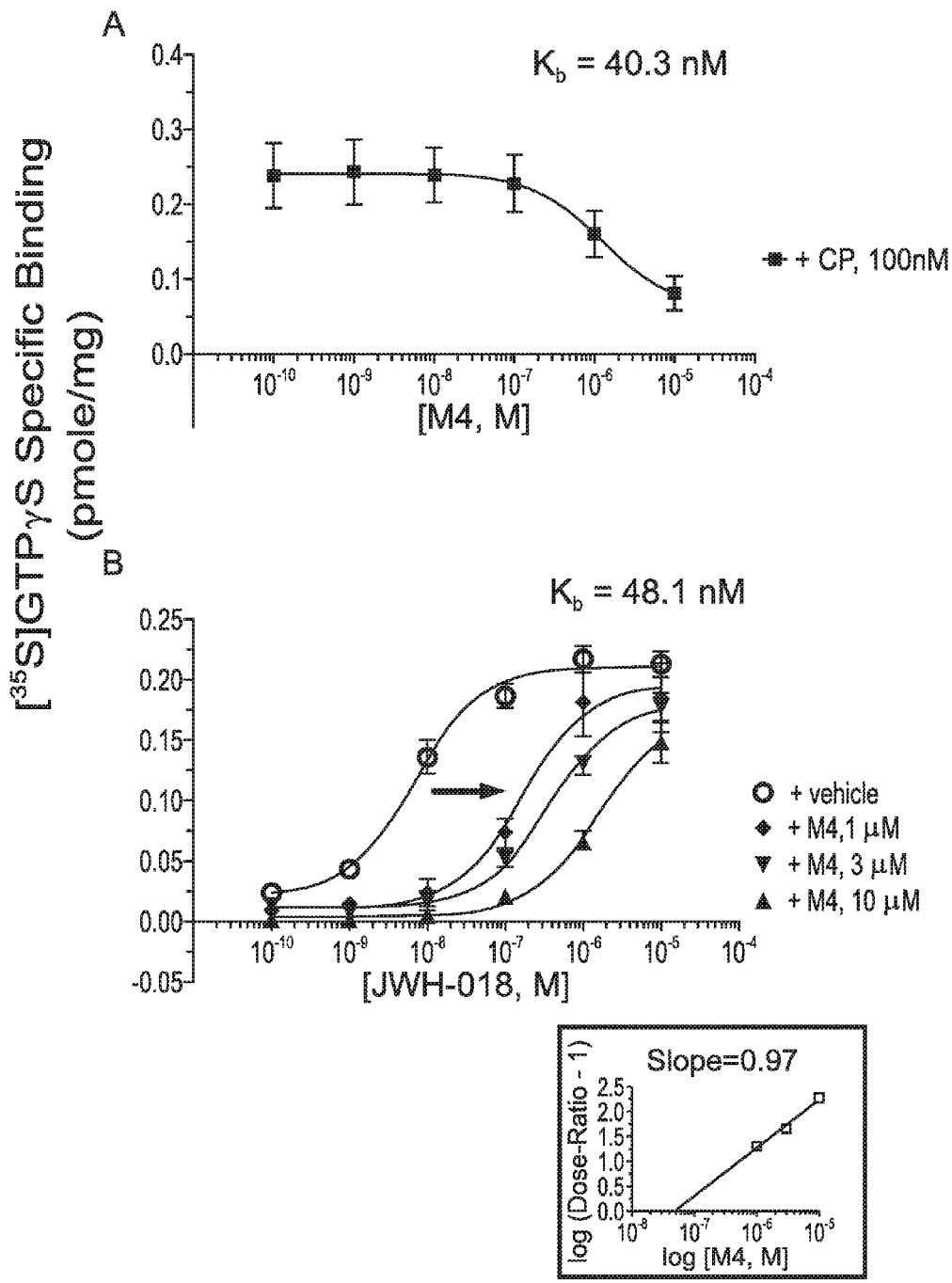
FIG. 8. M4 acts as an in vitro competitive neutral antagonist at CB1Rs. A. M4 blocks CB1R activation of G-proteins produced by an $EC_{90}$ concentration of CP-55,940 in mouse brain homogenates with a nanomolar $K_b$. B. Schild analysis of the concentration-dependent antagonism of JWH-018 by M4 yielded a nanomolar $K_b$ and a slope (not significantly different than 1) that indicates a competitive mechanism of antagonism (inset). The arrow indicates significant rightward-shifts in the potency of G-protein activation produced by JWH-018 in response to co-administration with increasing concentrations of M4.

Although M4 bound with intermediate nanomolar affinity to CB1Rs (e.g., 122 nM; FIG. 4), it neither significantly activated nor inhibited basal G-protein activity and thus was devoid of intrinsic activity as measured by this functional assay (FIG. 5). These combined observations intriguingly predict that M4 might serve as a physiologically relevant neutral antagonist at CB1Rs; hence it was selected for further characterization. First, concentrations of M4 alone ranging from 0.1 nM to 10 μM neither significantly increased (characteristic of agonists), nor decreased (characteristic of inverse agonists), basal [$^{35}$S]GTPγS binding levels (FIG. 7A). These observations indicate that M4 may act as a neutral CB1R antagonist concerning G-protein regulation in mouse brain homogenates. Second, the ability of co-administration with a receptor saturating concentration of M4 (10 μM) to antagonize effects on G-protein activity produced by three different CB1R agonists (FIG. 7B) or two CB1R inverse agonists (FIG. 7C) was examined. In all cases, co-incubation with M4 significantly antagonized the action of agonists (to increase) or inverse agonists (to reduce) [$^{35}$S]GTPγS binding. Third, a measure of the potency of CB1R antagonism produced by M4 was investigated by determining the antagonist dissociation constant (e.g., $K_b$) at CB1Rs, for two different agonists employing two alternative but complementary methods (FIG. 8). Initially, the ability of increasing concentrations of M4 to reduce [$^{35}$S]GTPγS binding induced by a single EC$_{90}$ concentration of CP-55,940 (100 nM) in mouse brain homogenates was conducted (FIG. 8A). Co-incubation with M4 produced a concentration-dependent decrease in CP-55,940-induced [$^{35}$S]GTPγS binding. Conversion of the IC$_{50}$ of this curve to a measure of antagonist potency by employing a modified function of the Cheng-Prusoff equation [46], revealed a $K_b$ value 40.3 nM for M4. Schild analysis [47] was additionally conducted to determine not only the $K_b$ value of M4, but also whether M4 produces competitive or non-competitive antagonism at CB1Rs (FIG. 8B). Since JWH-073 and JWH-018 are often co-abused, as noted by their concurrent presence in K2 products, as well as accounts of users combining JWH-018 with JWH-073 in deliberate ratios [36], we examined the ability of M4 to antagonize the G-protein activation produced by JWH-018. The ability of three different M4 concentrations (1, 3, and 10 µM) to shift the [$^{35}$S]GTPγS binding curve produced by JWH-018 was investigated (FIG. 8B). M4 produced a concentration-dependent shift-to-the-right of the JWH-018 curve without affecting maximal efficacy. Specifically, JWH-018 alone activates G-proteins with an EC$_{50}$ of 8 nM, which is in close agreement with data previously published [39]. However, in the presence of increasing concentrations of M4, the EC$_{50}$ of JWH-018 increased to 178, 263, and 1562 nM. This yielded a Schild plot with a slope of 0.97 (FIG. 8B, inset) and a $K_b$ of 48.1 nM. This value is in close agreement with the $K_b$ determined in FIG. 8A (e.g., 40.3 nM) and, most importantly, clearly indicates that M4 is a potent, competitive antagonist at CB1Rs.

3.4. M1 Displays JWH-073-Like Activity In Vivo.

Figure 9:
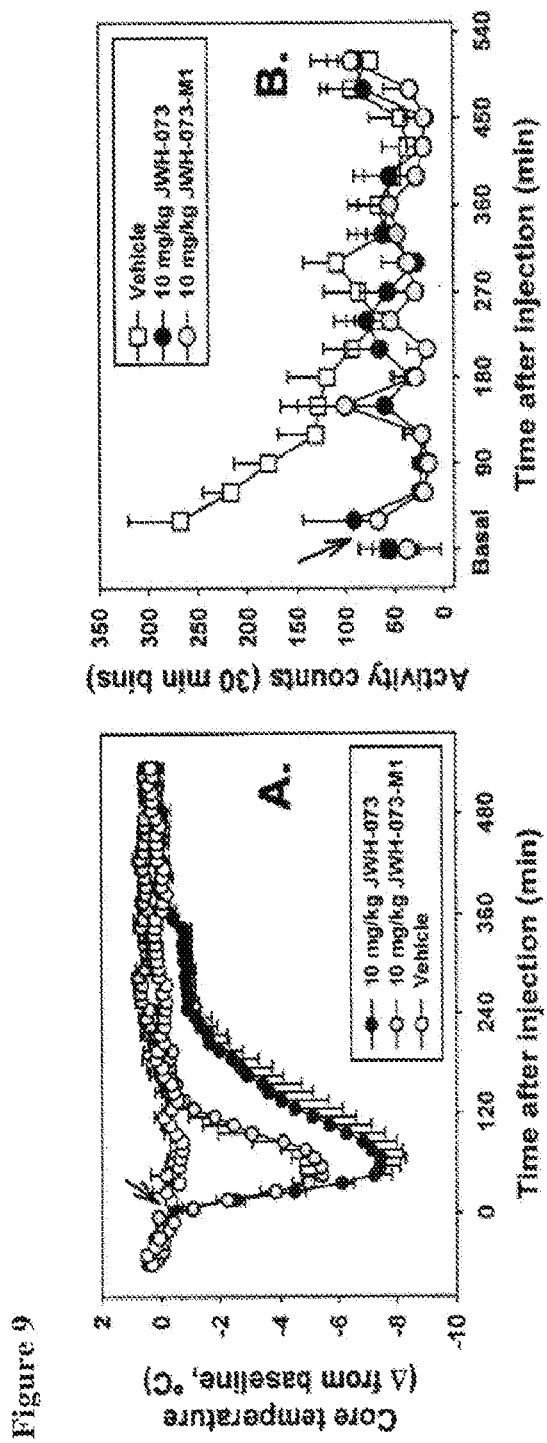
FIG. 9. M1 induces hypothermia and locomotor suppression similar to JWH-073. Time course telemetry data shows that both JWH-073 (10 mg/kg, i.p., black circles) and M1 (10 mg/kg, i.p. gray circles) produce A. robust hypothermia, and B. locomotor suppression, relative to vehicle control. This indicates that M1 retains the partial-to-full potency and efficacy of JWH-073 to produce hypothermia and locomotor suppression. Arrow indicates time of vehicle or cannabinoid administration.

M1 was tested in NIH Swiss Mice for effects on two well-established cannabinoid endpoints, core body temperature and locomotor activity, as was similarly performed in our previous study examining JWH-018 and its M1 derivative [39]. As reported in that study, cannabinoids induce hypothermia and suppress locomotor activity [49]. In the present study, mice were implanted with telemetry probes that simultaneously measure core body temperature and locomotor activity as described previously in the "Methods" section. Administration of JWH-073 or M1 (10 mg/kg, i.p.) resulted in sharp drops in core body temperature, with the minimum temperatures recorded being 29.74±1.44° C. for JWH-073 and 30.32±0.66° C. for M1 (FIG. 9A). Time to maximal core body temperature reduction (T.) did not differ for the two cannabinoids examined (54.17±5.23 minutes for the parent compound and 58.00±4.64 minutes for M1), suggesting a similar pharmacokinetic profile. Simultaneously, M1 resulted in a reduction of locomotor activity similar to that observed with administration of JWH-073 (FIG. 9B). Taken together, these data suggest that M1 retains a substantial portion of the in vivo activity exhibited by the parent compound.

3.5. M4 Antagonizes JWH-018-Induced Hypothermia In Vivo.

The observation that M4 behaves as a neutral, competitive CB1R antagonist in vitro prompted the investigation of its potential CB1R antagonist activity in vivo. In the following experiments, M4 (10 mg/kg, i.p.) was co-administered in NIH Swiss mice with JWH-018 (3 mg/kg, i.p.) to determine if M4 antagonizes four different measures of in vivo cannabinoid activity, commonly known as the cannabinoid tetrad: hypothermia, locomotor activity suppression (both described in the previous subsection), analgesia, and catalepsy. Previous work in this model showed that JWH-018 (3 mg/kg, i.p.) significantly decreases core body temperature and locomotor activity [39]. Initially, a dose of 10 mg/kg, i.p., of M4 was administered to test its antagonism of the hypothermic effects induced by JWH-018 (3 mg/kg, i.p.). This dose of M4 was chosen for initial in vivo experiments because of the striking cannabimimetic effects elicited by 10 mg/kg, i.p. of the structurally similar M1 derivatives of both JWH-018 [39] and JWH-073 (see previous subsection). In the present study, 3 mg/kg of JWH-018 administered i.p. produces hypothermia as indicated by a maximal decrease in core body temperature to 30.28+/−0.71° C. (FIG. 10A). In marked contrast, M4 resulted in no significant change in body temperature. Significantly, hypothermia induced by JWH-018 was blunted by co-administration with M4 (to 33.09+/−0.70° C.). Although co-administration with M4 did not completely prevent the reduction in body temperature produced by JWH-018, it did significantly blunt JWH-018-induced hypothermia (FIG. 10B). Quantification of this effect is indicated by summation of area under the curve (AUC) data generated 0-500 minutes after injection. Most importantly, these data demonstrate that M4 acts as a CB1R antagonist not only in vitro, but also in vivo.

Figure 11:
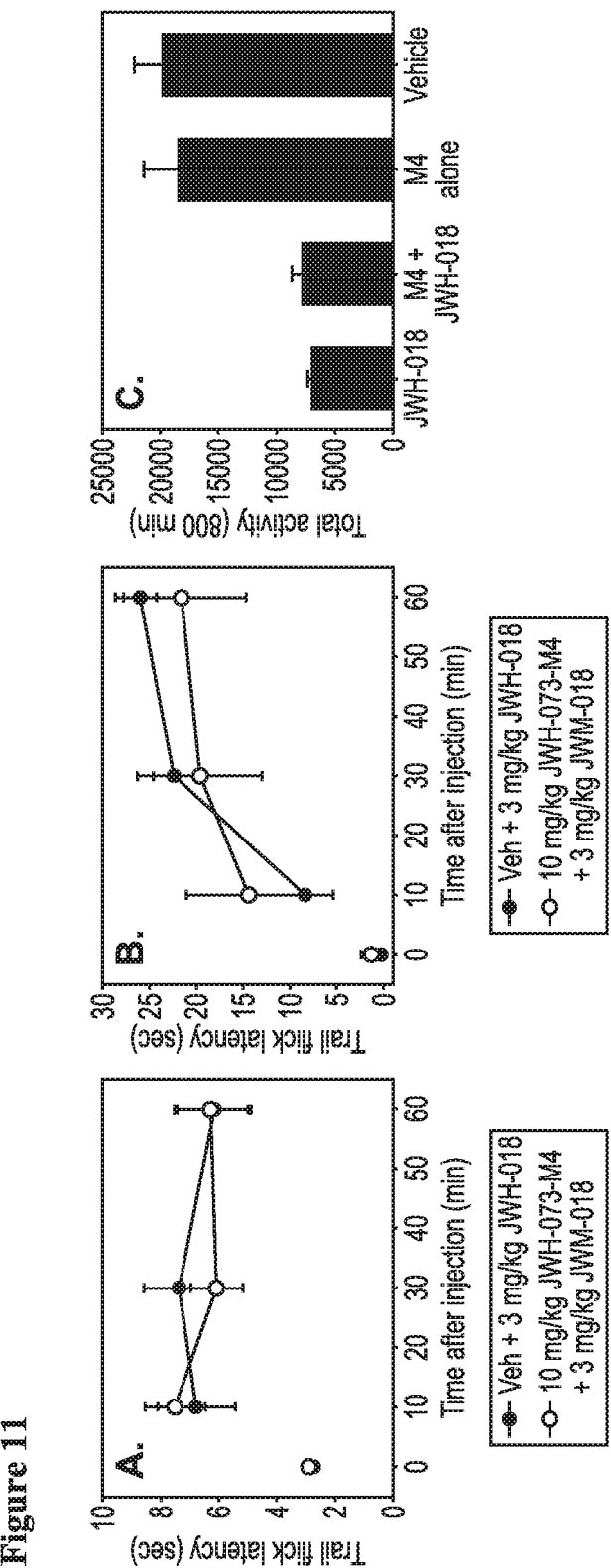
FIG. 11. M4 does not antagonize analgesia, catalepsy or locomotor suppression induced by JWH-018. Administration of JWH-018 (3 mg/kg, i.p., black circles) produces A. robust analgesia (tail flick assay), B. catalepsy, and C. locomotor suppression. Co-administration of M4 (10 mg/kg, i.p., white circles) does not significantly alter any of the JWH-018-induced effects (P<0.05, one-way ANOVA with Tukey HSD test, mean±SEM, n=5-6).

Potential antagonism of other JWH-018-induced effects (analgesia, catalepsy, and locomotor suppression) by this dose of M4 was also examined. Coadministration of M4 with JWH-018 (3 mg/kg, i.p.,) showed no difference in these assays from JWH-018 alone (FIG. 11). In all cases, the overall ANOVA was significant due to main effects of time (P=0.002 for locomotor activity. P=0.004 for analgesia, and P=0.003 for catalepsy), but there were no between-group comparisons at any time point that reached statistical significance.

Discussion

This study is the first to report that potential monohydroxylated metabolites of JWH-073 retain physiologically relevant, high (M1), intermediate (M4 and M5) and low (M3) affinity for CB1Rs. M1, M3, and M5 also activate G-proteins in a CB1R-dependent manner with partial agonist activity equivalent to that produced by the major psychoactive constituent in marijuana, $\Delta^9$-THC. M1 was further characterized for potential in vivo activity and, similar to JWH-073, induces hypothermia and suppresses locomotor activity in mice. M4 was also importantly shown to act as a novel competitive neutral CB1R antagonist. Specifically, [$^{35}$S]GTPγS binding experiments demonstrate that co-incubation with M4 blocks modulation of CB1R activity by both agonists and inverse agonists, with no effect on basal G-protein activity when tested alone. M4 antagonizes CB1R-mediated G-protein activation by JWH-018 in a competitive manner with a $K_b$ value of 48 nM. Finally, M4 attenuates JWH-018-induced hypothermia in mice, while an equivalent dose does not antagonize other CB1R-dependent effects that are entirely mediated by CNS-specific CB1Rs. Both in vitro and in vivo data presented collectively indicate that metabolism of JWH-073 may produce a complex mix of metabolites exhibiting a range of CB1R intrinsic activity that work "in concert" to contribute to the biological actions of JWH-073-containing products. Furthermore, the neutral CB1R antagonist properties of M4 suggest that this molecule might serve as a scaffold for development of a novel class of anti-obesity drugs (discussed below).

The first novel finding reported here is that M1 and M5 retain high and intermediate affinity for CB1Rs, respectively. Furthermore, both compounds act in vitro as agonists at CB1Rs, while M1 was also shown to demonstrate CB1R agonist activity in vivo. If future comprehensive pharmacokinetic studies confirm that metabolism of JWH-073 produces multiple active metabolites with significant CB1R affinity and activity (such as the ones examined in the present study), these acute actions could result in prolonged, excessive activation of CB1Rs. Furthermore, additive or synergistic actions exerted by multiple active metabolites, combined with the agonist activity of other synthetic cannabinoids present in K2 products, could potentially result in adverse effects rarely observed with marijuana, since $\Delta^9$-THC is metabolized to only one reported major active metabolite [50].

In addition to acute actions, sustained elevations of active cannabinoids following chronic K2 abuse would be expected to produce adaptive alterations in CB1R signaling [22, 51-53] that might interfere with normal endocannabinoid function. For example, prolonged endocannabinoid dysregulation could disrupt a wide variety of physiological functions including mood and cognition [54], appetite and energy homeostasis [55, 56], pain sensation [57], immune function [58], bone homeostasis [27] and reproduction [28]. In support of this suggestion, many similar adverse effects are observed following chronic *cannabis* use [59-61].

It is also possible that prolonged exposure to K2 synthetic cannabinoids and their active metabolites may promote K2 dependence, characterized by a withdrawal syndrome upon abrupt cessation of use. Although the subject of *cannabis* dependence and withdrawal remains controversial, reliable evidence has accumulated to define a specific marijuana withdrawal syndrome in human subjects [62], occurring with a prevalence of approximately 9% in regular marijuana users [63]. Selective reduction in the density of cortical CB1Rs has also been reported in chronic *cannabis* users [64]. Such CB1R downregulation would presumably result in reduced CB1R signaling, potentially contributing to the development of tolerance. It could therefore be predicted that chronic use of higher efficacy cannabinoids present in K2, coupled with the sustained action of associated active metabolites, might produce similar or even greater adaptations leading to enhanced levels of tolerance and/or dependence relative to chronic *cannabis* use.

If metabolism of JWH-073 results in accumulation of physiologically relevant concentrations of the CB1R antagonist M4 in the CNS, first-time exposure to JWH-073-containing products may acutely precipitate withdrawal in high-intake *cannabis* and K2 users. In support of this hypothesis, it is interesting that symptoms of *cannabis* withdrawal resemble several adverse effects associated with K2 use (e.g., anxiety, aggression, irritability, hypertension) [65, 66]. High concentrations of M4 accumulating in the CNS could also promote compensatory escalations in K2 use in order to maintain the subjective, reinforcing effects of K2 use, while production of low or moderate concentrations of this antagonist may explain the "mellowness" attributed to JWH-073 relative to other synthetic cannabinoids [67]. In any case, both acute and chronic cellular responses resulting from use of JWH-073-containing products are possibly influenced by actions produced by a combination of the parent compound and its active metabolites.

Overactivity of the endocannabinoid system appears to contribute to development of obesity and metabolic syndrome [68]. As such, CB1R antagonists/inverse agonists showed great promise as anti-obesity agents. However, the first-in-class drug rimonabant was denied approval by the United States Food and Drug Administration (USFDA) and was subsequently removed from the European drug market due to severe psychiatric side effects, including depression, anxiety, and increased risk of suicide [69].

Figure 10:
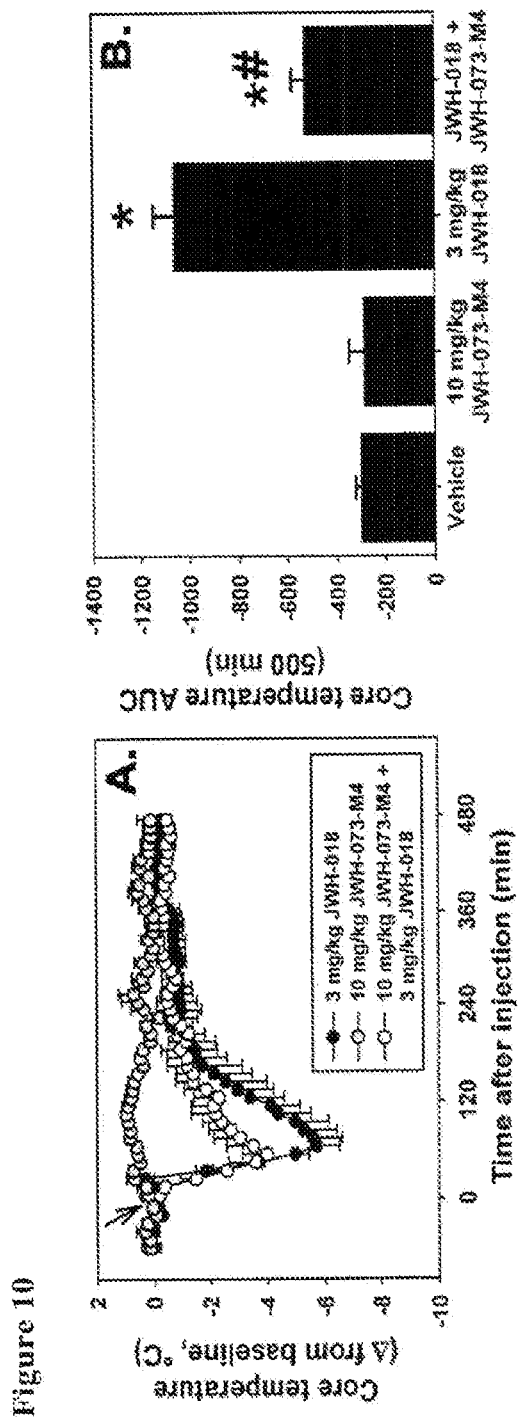
FIG. 10. M4 blunts JWH-018 induced hypothermia in mice. A. Time course telemetry data after administration of JWH-018 (3 mg/kg, i.p., black circles), M4 (10 mg/kg, i.p., gray circles), or co-administration of these doses (white circles). Arrow indicates time of vehicle or cannabinoid administration. B. Area under the curve summation of telemetry data collected 0-500 minutes after vehicle or cannabinoid administration shows that M4 significantly attenuated hypothermia induced by JWH-018, indicating that M4 displays CB1R antagonism in vivo. (*P<0.05 vs. vehicle, #P<0.05 vs. JWH-018 alone, one-way ANOVA with Tukey HSD test, mean±SEM, n=5).

Notably, M4 blunted, but did not completely block, CB1R-induced hypothermia (FIG. 10). Furthermore, M4 curiously failed to antagonize other CB1R-mediated effects in the cannabinoid tetrad (FIG. 11). These observations suggest that M4 does not readily enter the brain to antagonize centrally mediated effects of JWH-018 (e.g., analgesia, catalepsy, and locomotor suppression), but can partially antagonize the effect of CB1R-induced hypothermia, which has been shown to be mediated, in part, by peripheral CB1Rs [70]. Further pharmacokinetic experiments, particularly mass spectrometry of brain tissue samples following peripheral administration of M4 will conclusively determine the peripherally-restricted properties of M4.

Our group recently reported that several monohydroxylated metabolites of the synthetic cannabinoid JWH-018 retain high CB1R affinity and activity [39]. The current report similarly examined the affinity and activity of several potential JWH-073 metabolites at CB1Rs. Although the present study shows that potential monohydroxylated metabolites of JWH-073 also retain significant affinity and activity, a distinct difference between reports is discovery of M4: a neutral CB1R antagonist with nanomolar affinity and potential significance for development of anti-obesity therapeutics. Regardless of intrinsic activity, metabolites retaining high CB1R affinity have potential to exaggerate or disrupt cannabinoid signaling. The finding that multiple JWH-073 candidate metabolites retain high CB1R affinity and exhibit a range of intrinsic activity provides valuable mechanistic insight and suggests that biotransformation of K2 may contribute to the relatively high rate of severe adverse effects often reported with use of this rapidly emerging drug of abuse.

Example 2

Evidence that JWH-073-M4 is Peripherally Restricted and is a CB2R Agonist

Figure 12:
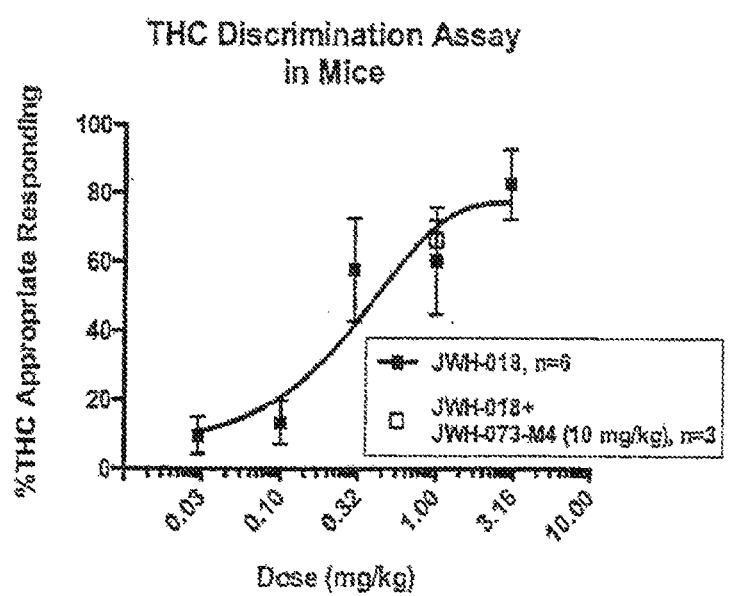
FIG. 12. M4 does not antagonize the generalization of JWH-018 to THC. Mice were trained in operant conditions to respond to one particular lever when dosed with THC (training dose=10 mg/kg, i.p.), and on a different lever when dosed with an equal volume of vehicle. Ten consecutive responses made on the appropriate lever resulted in reinforcement with 1 dipper of milk (fixed ratio schedule of reinforcement=10), up to 60 reinforcements per training session. When daily training sessions began producing ≥80% appropriate responding for the first reinforcement per session, test sessions to determine if mice could discriminate a test compound (in this case JWH-018) from the training dose of THC were performed. As shown here, doses of JWH-018 (filled squares) ranging from 0.32 to 3.16 mg/kg generalized well with THC. To determine if M4 could antagonize this effect, M4 (10 mg/kg i.p., open square) was co-administered with 1 mg/kg JWH-018. No change in THC-appropriate responding was observed with this co-administration of M4.

A. Evidence that JWH-073-M4 May Poorly Penetrate the Central Nervous System (CNS) and Thus be Restricted to Actions in the Periphery:

Previous experiments in our laboratory determined that M4 is a competitive neutral antagonist at CB1Rs in vitro (Example 1), a finding that has therapeutic implications for many indications including obesity and chronic liver disease. Subsequent experiments performed in mice sought to ascertain whether or not M4 antagonizes several CB1R-mediated effects of the synthetic cannabinoid JWH-018 (3 mg/kg, i.p.) in vivo. These effects include hypothermia, analgesia, catalepsy and suppressed locomotor activity. Indeed, M4 (10 mg/kg, i.p.) significantly blunted hypothermia induced by JWH-018, but M4 alone had no effect on core body temperature relative to vehicle controls (FIG. 10). Interestingly, this dose of M4 did not alter JWH-018-induced analgesia, catalepsy, and locomotor suppression (FIG. 11), nor did it antagonize the generalization of JWH-018 (1 mg/kg, i.p.) to THC in mice trained to discriminate 10 mg/kg, i.p. THC (FIG. 12). Importantly, cannabinoid-induced analgesia, catalepsy, locomotor suppression and THC discrimination are mediated entirely by CB1Rs located in the CNS, while cannabinoid-induced hypothermia appears to be mediated by both peripherally and centrally located CB1Rs [72]. While not conclusive, these results collectively indicate that M4 may be peripherally restricted. If so, M4 likely will possess a lower psychiatric adverse effect profile relative to previously reported CB1R antagonists, which failed development as anti-obesity drugs due to unacceptable high rates of depression and suicidal thoughts.

B. Evidence that JWH-073-M4 not Only Acts as a Neutral CB1R Antagonist, but Also Exhibits Agonist Activity at CB2 Receptors (CB2Rs):

While the psychoactive, cannabinoid 1 receptor (CB1R)-mediated effects of synthetic cannabinoids are apparent in animal studies, as well as in the human users of synthetic *cannabis*, very little is known of the actions of these molecules and their metabolites at immune-modulating cannabinoid 2 receptors (CB2Rs). Our recent work has revealed properties consistent with potential therapeutic usefulness of one particular metabolite of the synthetic cannabinoid JWH-073, designated M4, at CB1Rs. These observations prompted our initial proposal to pursue development of M4 as a therapeutic, which includes determining the affinity and intrinsic activity of this compound at CB2Rs.

Figure 13:
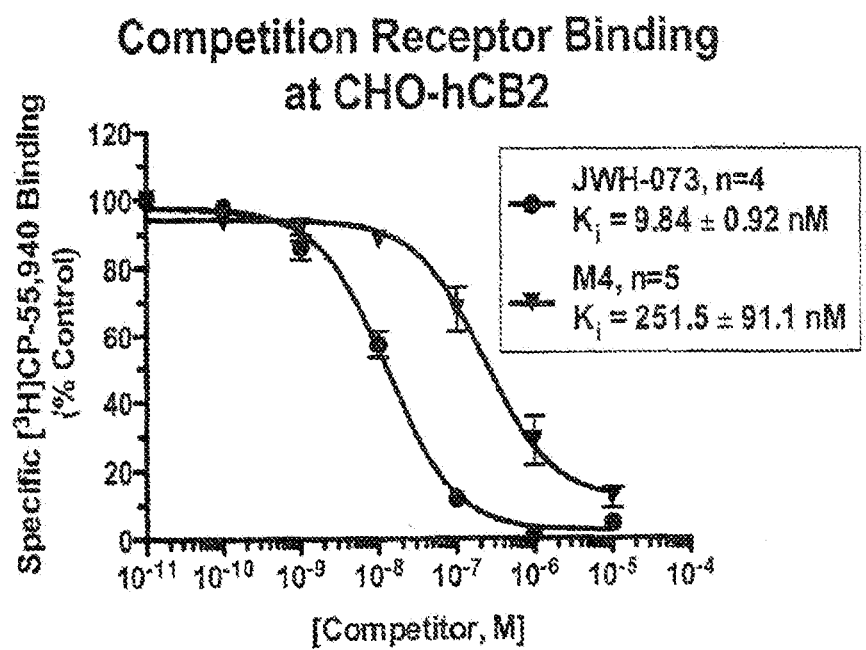
FIG. 13. M4 exhibits physiologically relevant affinity for hCB2Rs. Like it parent compound, JWH-073, M4 competes with and completely displaces [$^3$H]CP-55,940 from hCB2Rs.

The parent compound JWH-073 acts as a high affinity agonist at both CB1 and CB2Rs [44]. Potential affinity and intrinsic activity of M4 at CB2Rs, in addition to action at CB1Rs, is important to predicting the ultimate therapeutic potential of this compound (see discussion following). Therefore, we conducted experiments to initially characterize the actions of M4 at human CB2Rs (hCB2Rs). First, the affinity ($K_i$) of M4 at hCB2Rs was found to be 251±91.1 nM (mean±SEM, n=5; FIG. 13). This was determined by competition receptor binding assays employing homogenates prepared from CHO-hCB2 cells (100 μg) as described in Section 2.3 of Example 1.

Although exhibiting lower affinity for hCB2Rs relative to the parent compound JWH-073 (9.84±0.92 nM), M4 nevertheless also binds to hCB2Rs with an affinity in the intermediate nanomolar range. Nanomolar binding affinity is considered physiologically relevant, and warranted further experiments to determine the intrinsic activity of M4 at hCB2Rs. Therefore, preliminary functional studies examining the pharmacodynamic actions of M4 at hCB2Rs have been performed (see following), and further characterization is currently ongoing in our laboratory.

In order to determine intrinsic activity, the ability of M4 to act as a full agonist, partial agonist, neutral antagonist, or inverse agonist at hCB2Rs concerning regulation of the intracellular effector adenylyl cyclase in intact CHO-hCB2R cells was examined. Adenylyl cyclases are a family of membrane-bound enzymes that catalyze the intracellular production of the second messenger cAMP from ATP. Adenylyl cyclase activity is modulated by activated G-proteins: Gs-proteins stimulate activity, while Gi/o-proteins are inhibitory. Thus, agonists of G-protein coupled receptors (GPCRs) coupled to Gi/o-proteins, such as hCB2Rs, decrease cAMP production due to inhibition of adenylyl cyclase activity. In this assay, intact CHO-hCB2R cells are preincubated with [$^3$H]-adenine and treated with forskolin (10 or 30 μM) to stimulate adenylyl cyclase activity. This results in the production of intracellular [$^3$H]cAMP, which is then experimentally isolated by column chromatography with acidic alumina and quantified using a liquid scintillation counter. Treating cells concurrently with a hCB2R agonist in the presence of forskolin results in a decrease in the production of [$^3$H]cAMP relative to forskolin alone. Neutral antagonists have no effect on, and inverse agonists increase, [$^3$H]cAMP production relative to vehicle controls [40].

Figure 14:
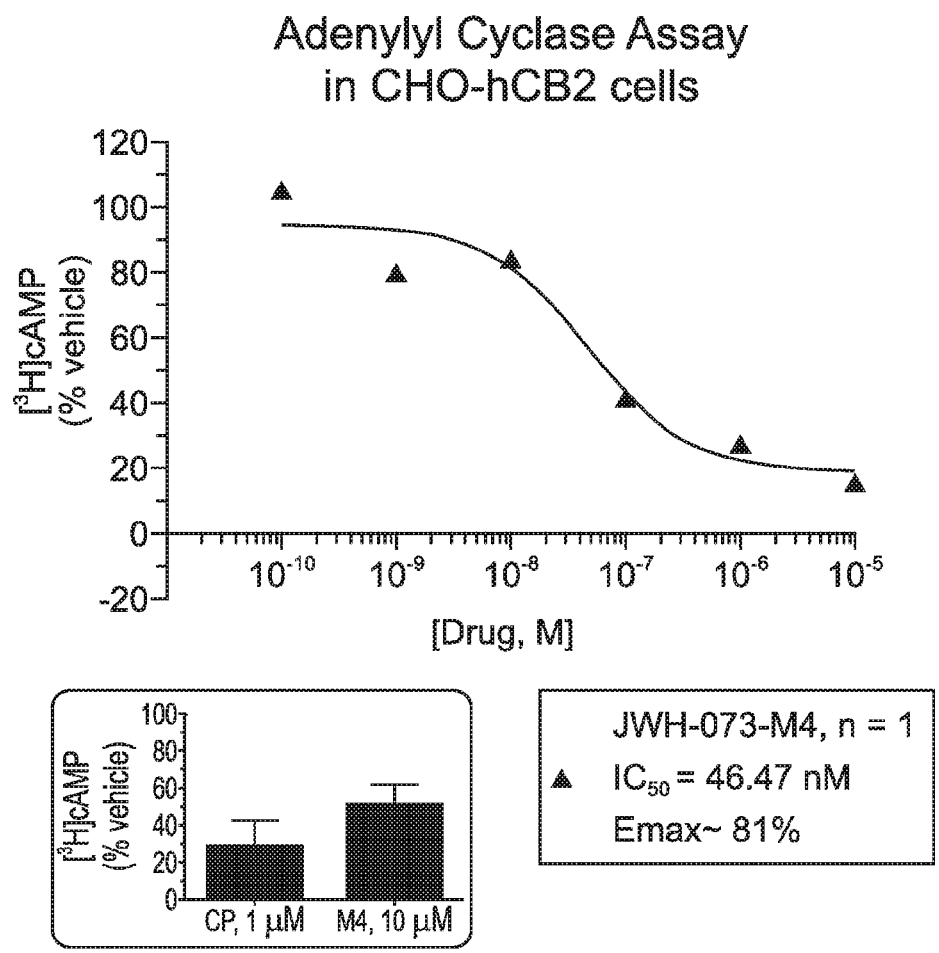
FIG. 14. M4 acts as a full agonist in CHO-hCB2 cells. Experiments show that a single concentration of M4 (10 μM) inhibits intracellular cAMP production by 48% (n=3), which is not significantly different from inhibition produced by the nonselective cannabinoid full agonist CP-55,940 (71%, n-2, by Student's t-test, significance designated P≤0.05; inset). A concentration effect curve shows that M4 inhibits cAMP production by 81% relative to vehicle controls with nanomolar potency (n=1). NOTE: Ten μM forskolin was used in the concentration effect experiment, while 30 μM was used in the single point experiments.

As shown in FIG. 14, M4 produces a concentration-dependent inhibition of intracellular cAMP production with nanomolar potency ($IC_{50}$) in CHO-hCB2R cells. Therefore, M4 likely acts as an agonist at hCB2Rs in this transfected cell line. Data in FIG. 14 also compares a measure of maximal efficacy (e.g., Emax) of M4 to that of a well-characterized full agonist CP-55,940 (inset). These results indicate that M4 acts as a full or near-full agonist.

C. Evidence that Combined CB1R Antagonist/CB2R Agonist Actions of JWH-073-M4 May Offer Unique Benefits for Treatment of Obesity and Chronic Liver Diseases:

CB2Rs are located primarily on, and modulate the activity of, immune cells. Upregulation of CB2Rs and endocannabinoids occurs in inflammatory conditions, and activation of CB2Rs decreases proliferation, migration, and overall activity of immune cells; thus, CB2R activation is often anti-inflammatory [73]. M4 may prove to be a potent and efficacious anti-inflammatory agent by signaling through CB2Rs. Both obesity and chronic liver disease are highly associated with chronic inflammation that, if left unchecked, eventually leads to tissue damage with possible fibrosis, resulting in the irreversible loss of native function of the involved tissues. While these conditions apparently cause inflammation, it is also quite likely that the inflammation itself contributes to the maintenance of these conditions [74]. Therefore, the simultaneous antagonism of CB1Rs and activation of CB2Rs by M4 would be predicted to improve blood lipid profile (by increasing HDL:LDL ratio and decreasing triglycerides and total cholesterol), increase insulin sensitivity, and decrease insulinemia, leptinemia, and body mass index, which are all proven consequences of peripheral-specific CB1R antagonism [75]. CB2R agonism would also be expected to combat systemic inflammation arising from obesity, which would likely improve patient health and well being to a greater degree than treatment with CB1R antagonists alone.

In chronic liver disease there is a progression from initial insult, leading to chronic inflammation and eventual fibrosis and liver failure. Other groups have demonstrated that CB1R and CB2R are both significantly upregulated in liver disease [76]. The combination of CB1R antagonism with CB2R agonism should produce anti-inflammatory actions and anti-fibrotic effects in chronic liver disease. Therefore, such dual activity of M4 at CB1 and CB2Rs could beneficially be useful for prevention of liver fibrosis (cirrhosis) and/or failure.

Example 3

Peripheral Restriction of M4

Further studies will be performed to more conclusively demonstrate whether M4 is peripherally restricted and the extent of its peripheral restriction, according to methods described in references [77] and [78]. Briefly, the compound is administered intravenously or intraperitoneally to rats or mice, and at time points from 1-24 hours later the animals are sacrificed and the concentration of the test compound in blood and brain tissue is determined by reverse phase HPLC or HPLC mass spectrometry.

Example 4

In Vivo Experiments to Show M4 Effect in a Mouse Model of Obesity

In vivo experiments in mice will be performed to demonstrate that M4 is an effective agent in reducing obesity in mice according to methods used in references [72], [77], and [79]. Briefly, the test substance may be injected intraperitoneally daily, or given orally, and food intake is measured and animal weight is monitored in animals fed ad libitum. Additionally, blood glucose and insulin levels may be measured to monitor effects on insulin resistance or metabolic syndrome.

Example 5

In Vivo Experiments to Show M4 Effect on a Mouse Model of Liver Fibrosis

In vivo experiments in mice will be performed to determine the effect of M4 in treating a mouse model of liver fibrosis according to methods used in reference [80]. Briefly, the compounds can be tested for their effect on concanavilin-A-induced cirrhosis by administration 30 minutes before or after concanavalin A and measuring the effects on alanine aminotransferase (ALT) in blood (Lavon, I. et al. 2003, *Mol. Pharmacol.* 64:1334-1341). They can also be tested for effects on hypotension in $CCl_4$-induced cirrhosis in rats.

Example 6

Figure 15:
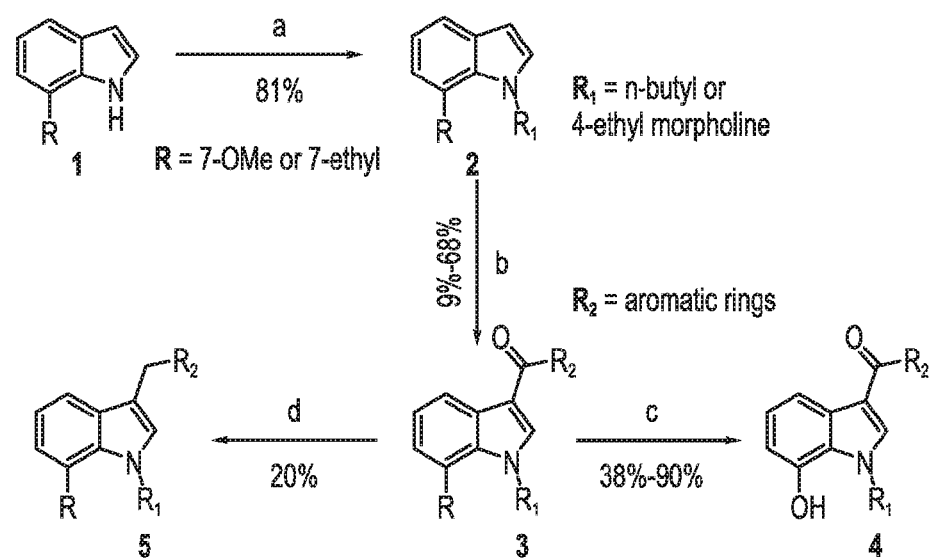
FIG. 15. Reaction Scheme 1. Reagents and conditions: (a) 1-bromobutane or 4-(2-bromoethyl) morpholine, KOH, DMF 50° C.; (b) Me$_2$AlCl, RCOCl, DCM, 0° C.; (c) BBr$_3$, DCM, NaHCO$_3$, MeOH, H$_2$O, −78° C.; (d) LiAlH$_4$, AlCl$_3$, THF, 0° C.
Figure 16:
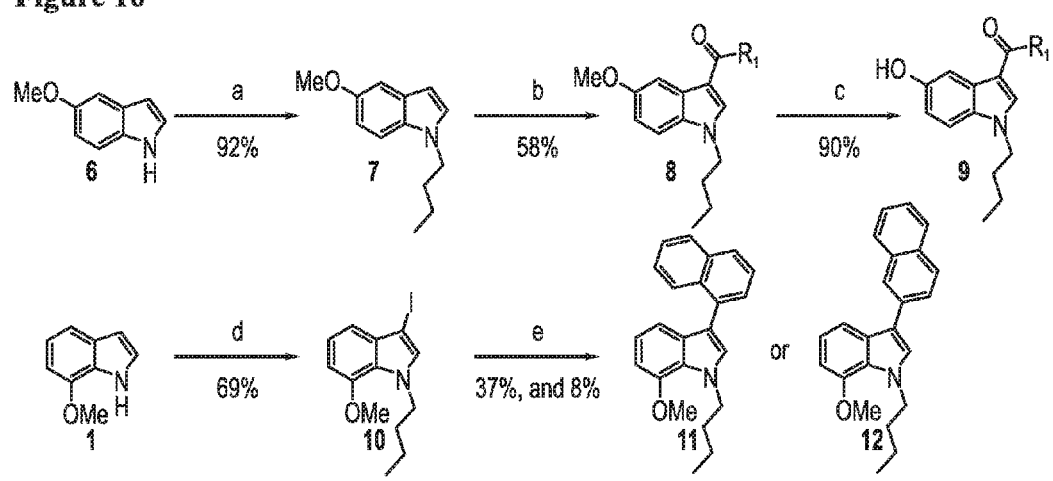
FIG. 16. Reaction scheme 2. Reagents and conditions: (a) 1-bromobutane or 4-(2-bromoethyl)morpholine, KOH, DMF, 50° C.; (b) Me$_2$AlCl, RCOCl, DCM, 0° C.; (c) BBr$_3$, DCM, NaHCO$_3$, MeOH, H$_2$O, −78° C.; (d) 1-bromobutane, I2, KOH, DMF, NaH, 50° C.; (e) Pd(PPh$_3$)$_4$, boronic acid, Na$_2$CO$_3$, DME, EtOH.

Design, Synthesis, and Biological Evaluation of Aminoalkylindole Derivatives and their Potential for Treatment of Alcohol Abuse Chemistry Synthesis of analogues based on the JWH-073-M4 scaffold began with the use of commercially available 7-methoxyindole 1, which was subjected to mild alkylating conditions to afford 1-butyl-7-methoxy-1H-indole (2), an important intermediate in 81% yield (FIG. 15). In addition, commercially available 7-ethylindole was also subjected to the aforementioned conditions to yield compound (2) with an ethyl substitution at the 7-position on the indole ring. Intermediate 2 was then subjected to Friedel-Crafts acylation conditions, using dimethylaluminum chloride and the appropriate acid chloride at 0° C. to afford many of the analogues prepared, structurally represented as intermediate (3), in yields ranging from 9%-68% (FIG. 15). Compound 3 was shown to be a versatile intermediate and can undergo several reactions to yield various scaffolds. Specifically, it undergoes 0-demetylation conditions with $BBr_3$ to afford compound (4) in yields ranging from 38%-90% as well as LAH reduction conditions to afford compound (5) in 20% yield. Similar conditions as the ones mentioned were utilized to afford compounds (8) and (9) in 58% and 90% yields, respectively, however starting from a different commercially available source, 5-methoxyindole 6 (FIG. 16). Compound 1 was additionally used in the synthesis of intermediate (10) utilizing a one-pot N-alkylation and 3-indole iodonation in 69% yield (FIG. 17). Intermediate 10 was then subjected to Suzuki coupling conditions utilizing different boronic acids to afford analogues (11) and (12) in 37% and 8% yields, respectively. Twenty-one analogues were synthesized to date and the structures of the analogues are schematically represented in FIG. 17.

Results and Discussion

Figure 18:
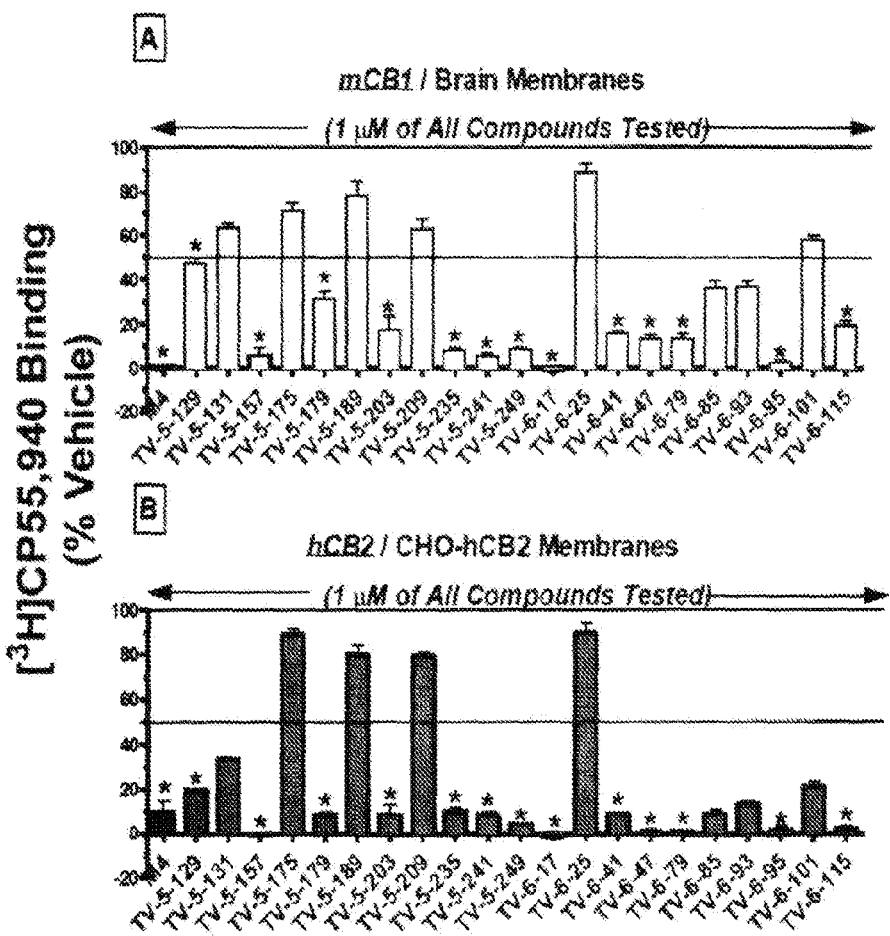
FIG. 18. Screen for M4-analog binding to CB1 and CB2 receptors.

The prepared analogues were subjected to in vitro pharmacological testing, which included receptor binding and functional assays at both cannabinoid receptors. Initial receptor binding screens at both CB1Rs and CB2Rs were conducted for the analogues prepared. These initial screens were done at a single analogue concentration of 1 µM, which would allow us to quickly attain the affinity of the compounds tested at the cannabinoid receptors. Compounds that would be considered for further functional binding studies were expected to displace 0.2 nM concentration of the high affinity CB1R/CB2R non-selective radioligand [$^3$H]CP-55,940 with high sub-micromolar affinity. Using the Cheng-Prusoff equation together with the conditions employed, one can predict that the concentration of a compound producing 50% displacement of [$^3$H]CP-55,940 from a receptor will estimate the compounds affinity for that receptor.[25] Data presented in FIG. 18 shows that a 1 µM concentration of most analogues tested produced greater than 50% displacement of [$^3$H]CP-55,940 from CB1R (FIG. 18A) and CB2R (FIG. 18B). As a result, out of the 21 analogues that were screened, 16 bind to CB1R and 18 bind to CB2R with sub-micromolar affinity. Several analogues exhibited very high affinity for either of the two receptors tested, which can be seen from their near 100% displacement of [$^3$H]CP-55,940 from both receptors. Based on the affinity observed for the CBRs, several compounds were chosen for further evaluation.

A functional assay screen for the inhibition of adenylate cyclase (AC) activity was chosen as the subsequent assay. This screen would allow us to gain a better understanding of the intrinsic activity of the analogues that displayed moderate to high sub-micromolar affinity for the CBRs. Reaching full-receptor occupancy, which is predicted to produce maximal efficacy, is desirable at 10 µM concentration of all the compounds was used. The non-selective CB1R/CB2R full agonist CP-55,940 was used as a positive control and it produced 45% AC-inhibition at CB1Rs endogenously expressed in Neuro2A cells (FIG. 19A) and 37% AC-inhibition in CHO cell transfected with hCB2 receptors (FIG. 19B). Most compounds tested exhibit AC-inhibition similar to that produced by the full agonist CP-55,940. TV-5-129, TV-6-249, and TV-6-41, however, produce lower AC-inhibition at CB1Rs than the full agonist CP-55,940 with −4, 18, and 16% inhibition, respectively (FIG. 19A). Despite little or no AC-inhibition observed at CB1Rs, these compounds behaved differently at CB2Rs. Specifically, the three compounds in question exhibited AC-inhibition that was in the range of the inhibition seen with CP-55,940 and were shown to inhibit adenylate cyclase with 22.1, 33.2, and 20.8%, respectively (FIG. 19B). These data indicate that three of the compounds examined display weak partial agonist activity at CB1Rs and partial to full agonist efficacy at CB2Rs.

Based on the efficacy data from the AC-inhibition screen together with the initial affinity screen, several compounds were selected for determination of full binding curves and ultimately their Ki at CBRs. Even though compound TV-5-129 produced minimal AC-inhibition, it was showed that this compound binds with high nanomolar affinity of 387 and 281 nM at CB1R and CB2R, respectively. Analogue TV-5-157 demonstrated superior affinity in the low nanomolar range of 1.7 nM for CB1 and 0.81 nM for CB2R. Compounds TV-5-249 and TV-6-41 displayed similar affinity at both receptors, however binding slightly tighter to the CB2R. The Ki for TV-5-249 at CB1 was observed to be 15.4 nM and 10.9 nM at CB2R. Compound TV-6-41 had affinity of 37.2 nM and 26.5 nM at CB1 and CB2R, respectively.

Figure 20:
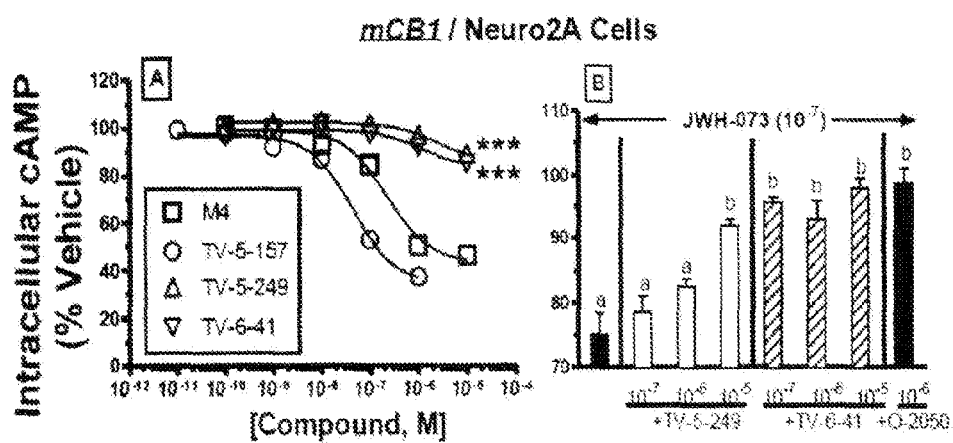
FIG. 20. M4 analogs TV-5-249 and TV-6-41 produce very little inhibition of AC activity when tested alone at high concentrations and antagonize AC inhibition produced by CB1 agonists. (*** Lead compounds selected for testing in animals.) ($^{a,b}$ Different letters signify statistical differences between groups.)
Figure 21:
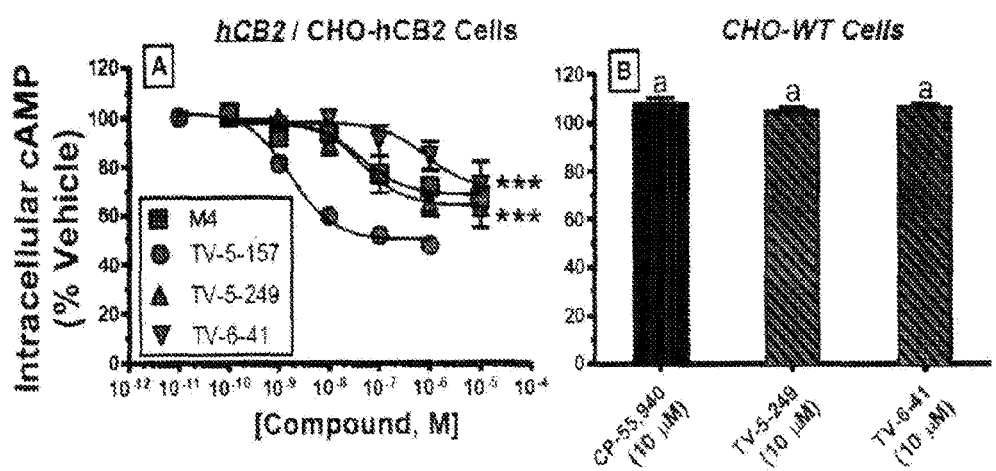
FIG. 21. M4 analogs produce concentration-dependent inhibition of adenylyl cyclase activity by activation of CB2 receptors. (*** Lead compounds selected for testing in animals.) ($^a$ Different letters signify statistical differences between groups.)

The four compounds whose Ki values were determined together with JWH-073-M4 were subjected to a functional assay for determination of their potency, which involves their ability to regulate AC-activity through CB1 and CB2Rs. Similar to what was observed in the initial AC-inhibition screen, JWH-073-M4 and TV-5-157 produced 50-60% inhibition of AC-activity via CB1Rs with $IC_{50}$ values of 225 and 45 nM, respectively. Conversely, TV-5-249 and TV-6-41 produced very little inhibition of AC-activity, which was observed at only very high concentrations of both analogues (FIG. 20A). In support of the observed activity, the two lead compounds and CB1R antagonist O-2050 significantly (1 µM concentration) antagonized AC-inhibition produced by the CB1R full agonist JWH-073 (FIG. 20B). In contrast, all of the compounds tested exhibit 40-50% inhibition of AC-activity at CB2Rs with potency similar to their rank order of Ki values seen in Table 3 (FIG. 21A). To examine if the observed agonist activity is due to activation of CB2Rs, an additional AC-inhibition assay was performed. As seen in FIG. 21B, neither TV-5-249 nor TV-6-41 significantly modify AC-activity in CHO-WT cells not transfected with CB2Rs, which signifies that the agonist activity observed for both compounds is indeed due to their activation of CB2Rs.

TABLE 3

Affinity (Ki) of M4 analogues for CB1R and CB2R.

| M4-Analogue | mCB1R Ki (nM) | hCB2R Ki (nM) |
| --- | --- | --- |
| JWH-073 | 12.9 ± 3.4 | 9.8 ± 0.9 |
| JWH-073-M4 | 24.2 ± 17.2 | 78.3 ± 36.2 |
| TV-5-129 | 387 ± 77.0 | 281 ± 51.0 |
| TV-5-157 | 1.7 ± 0.3 | 0.81 ± 0.4 |
| TV-5-249 | 15.4 ± 2.2 | 10.9 ± 3.1 |
| TV-6-41 | 37.3 ± 11.8 | 26.5 ± 1.5 |

Figure 22:
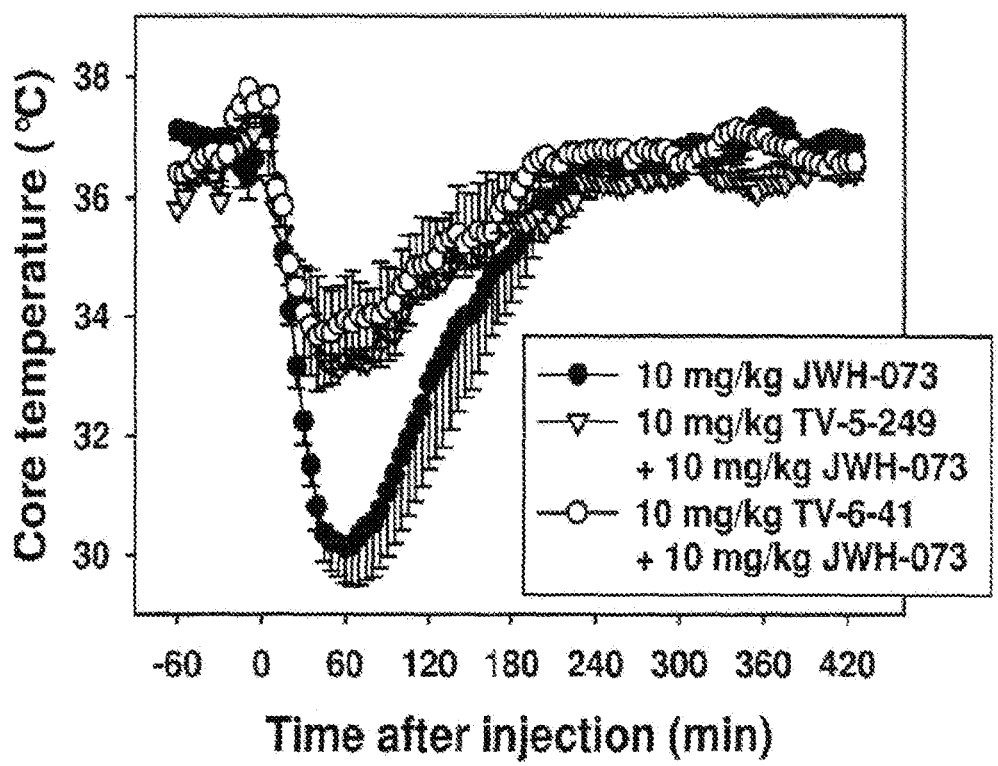
FIG. 22. Compounds TV-5-249 and TV-6-41 reduce JWH-073-induced hypothermic effects.

Compounds TV-5-249 and TV-6-41 displayed very intriguing in vitro data and were selected for further evaluation in in vivo mouse studies. Our hypothesis is that a dual activity CB1R antagonist/CB2R agonist will reduce the reinforcing effects of EtOH as well as reduce the conditioned rewarding effects of ethanol in mice. The compounds selected will firstly be put through a thermoregulation assay as a screen for potential cannabinoid receptor activity. Thermoregulation will be used as a screen because of the well-established hypothermic effects seen with the use of cannabinoid ligands [107,108]. This assay was done using glass radiotelemetry probes that were surgically implanted in each mouse, which monitor core temperature in response to drug administration [98]. 10 mg/kg administration of the full agonist JWH-073, highly abused in K2/Spice incense blend, elicited a profound hypothermic effect as seen in FIG. 22 (black circles). From FIG. 22 it can be seen that 30 minute pretreatment with compounds TV-5-249 (squares) and TV-6-41 (white circles), significantly decreased the hypothermic effects of JWH-073. This screen does indeed confirm the in vivo cannabinoid activity of TV-5-249 and TV-6-41 and it also illustrates the evident antagonist effects against agonist induced hypothermia.

Figure 23:
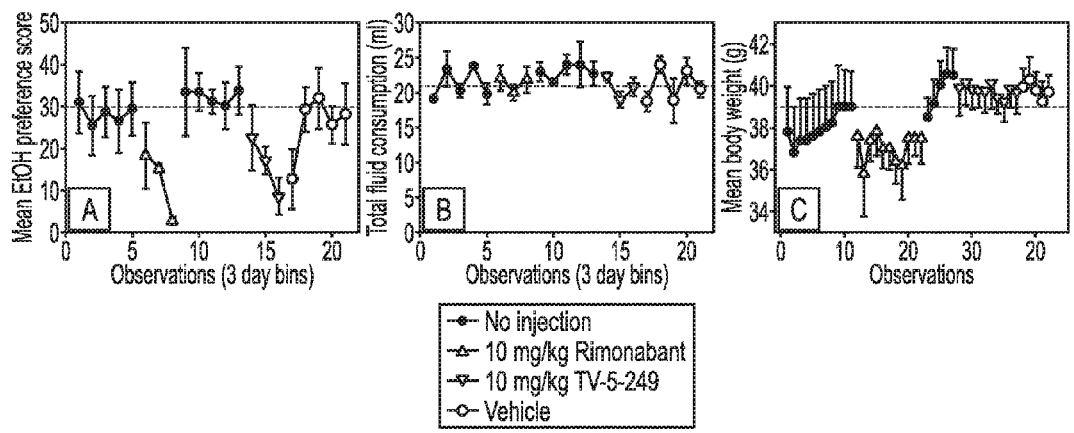
FIG. 23. Reduction of ethanol self-administration with daily administration of 10 mg/kg rimonabant or lead compound TV-5-249. Dotted lines represent group means from the 10 "no injection" control periods.

With the establishment of cannabinoid activity seen with the two lead compounds in the thermoregulation screen, TV-5-249 and TV-6-41 were further tested in two established in vivo models for alcohol abuse: oral self administration (SA) and alcohol conditioned place preference (CPP). These assays are important models for the study of alcoholism because they model several aspects of this condition including voluntary EtOH drinking (SA), conditioned EtOH reward (CPP), abstinence and relapse, which represent extinction and reinstatement of CPP, respectively. Effects of TV-5-249 on voluntary 10% EtOH drinking were studied using a 2-bottle choice procedure described by Keane and coworkers as wells as by Cunningham and coworkers [109,110]. Using rimonabant as a positive control, across 5 observations done under baseline "no injection" conditions it can be seen in FIG. 23A that EtOH preference and total fluid consumption (FIG. 23B) were steadily maintained. Daily treatment with 10 mg/kg rimonabant decreases EtOH preference (FIG. 23A) without having any effect on total fluid intake (FIG. 23B), which coordinates with previously published reports.[30] However, as previously published reports have stated, rimonabant does indeed have an effect on body weight (FIG. 23C) [112, 113]. Once treatment with rimonabant was concluded, mice were returned to baseline "no injection" condition where their weights increased and voluntary EtOH drinking continued. After 5 such observations, which represents a two week washout period, daily treatments with 10 mg/kg TV-5-249 were initiated. As seen with rimonabant, TV-5-249 treatment also reduced EtOH preference (FIG. 23A) without affecting total fluid consumption (FIG. 23B). However, unlike rimonabant, TV-5-249 did not decrease body weight of mice tested (FIG. 23C). The last treatment was an everyday injection of vehicle, which is 8% Tween/92% sterile water solution and it represents the solution in which both drugs were dissolved in prior to injections. EtOH preference with the exception of the first observation period, total fluid consumption, and mean body weigh were not affected by vehicle injections. This study helped us demonstrate that a JWH-073 derived compound exhibiting cannabinoid activity that is devoid of inverse agonist activity can replicate the effects on alcohol self-administration seen by rimonabant.

Figure 24:
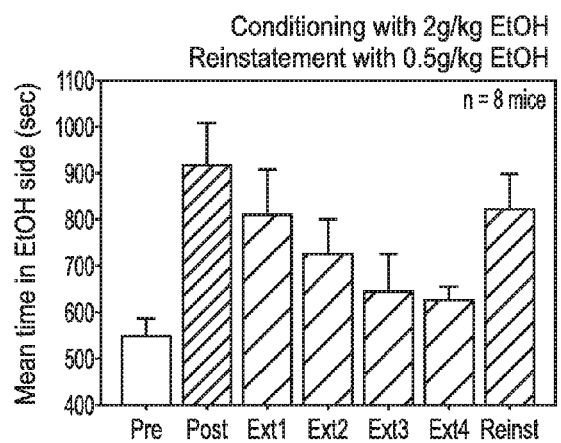
FIG. 24. Establishment of conditioned place preference (CPP) following four pairings of 2 g/kg EtOH, extinction across four sessions, and reinstatement with 0.5 g/kg EtOH.
Figure 25:
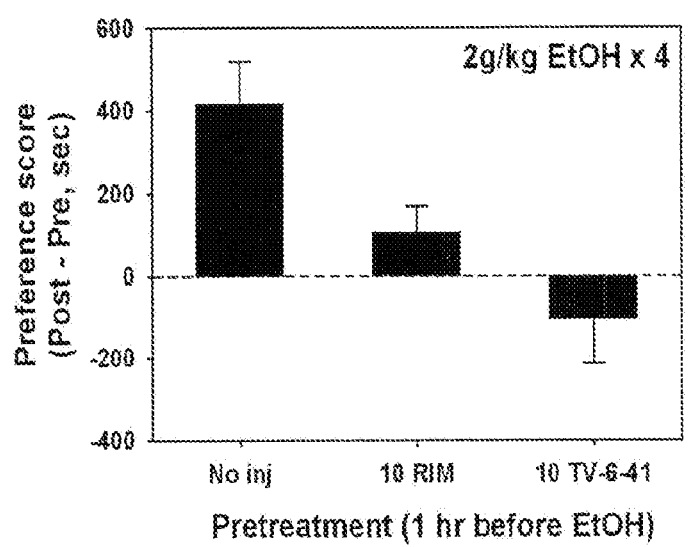
FIG. 25. Blockage of EtOH CPP with rimonabant and TV-6-41.

Alcohol conditioned place preference assay was done with compounds TV-6-41 and rimonabant. This assay tests the effects of these compounds on conditioned rewarding effects of EtOH. Training of mice involved 4 daily injections of 2 mg/kg EtOH paired with location to one of two chambers (four pairings) after which an increase in time spent in the EtOH-paired chamber was observed, and this points to the development of conditioned place preference (FIG. 24, 'Pre" bar vs. "Post" bar). Once conditioned place preference was established, 4 successive extinction trials were initiated, which gradually decreased time spent in the EtOH-paired chamber (FIG. 24, grey bars). Upon the final extinction trial a reinstatement period was initiated using a single priming injection of 0.5 mg/kg EtOH, thus increasing time spent in the EtOH-paired chambers compared to the last extinction trial, demonstrating reinstatement of the place preference conditioned by previous EtOH pairings (FIG. 24, fourth gray bar vs. red "Reinst" bar). With these data we were able to demonstrate our ability to condition place preference with EtOH, to extinguish that behavior, and to reinstate the behavior with a single priming injection of EtOH. With the CPP training underway, mice were exposed to succeeding conditioning trials either with 10 mg/kg TV-6-41 or 10 mg/kg, given 1 hour before EtOH pairings. It was observed that different groups of mice displayed variability in the time spent in each chamber during their respective conditioning trials, which led to normalizing the data observed to a "preference score" which can be calculated as the time spent in the EtOH compartment on the post-conditioning trial minus time spent in what would become the EtOH compartment in the pre-conditioning trial. During these studies it was observed that 4 pairings of 2 mg/kg EtOH elicited a CPP of about 400 sec (FIG. 25, "No inj" bar). It was observed that mice treated with 10 mg/kg rimonabant did not elicit a significant preference for the EtOH-paired chamber, which is in agreement with previously reported data (FIG. 25, "10 RIM" bar) [114,115]. Similarly to the observations seen with rimonabant, the conditioned rewarding effects of EtOH were blocked with the administration of 10 mg/kg TV-6-41. Collectively these studies helped us demonstrate that a novel indole-derived compound with cannabinoid activity lacking inverse agonist activity can replicate the effects of CPP elicited by alcohol seen by rimonabant.

Conclusions

The World Health Organization estimates that approximately 2.5 million people die from alcohol use every year.

Treatments for alcohol related disorders are available but many come with moderate to severe side effects, demonstrating a need for novel alcohol treatments. CBR ligands that attenuate the endocannabinoid signaling can have an effect on several disorders, among which are alcohol dependence and related disorders. In order to achieve that goal we set to synthesize a dual activity CB1R antagonist/CB2R agonist based on the JWH-073-M4 scaffold with improved drug like properties. We set to explore the JWH-073-M4 scaffold utilizing a molecular dissection approach in order to better understand the elements involved in the production of cannabinoid activity. We investigated the necessity of the naphthalene ring and the electronic potential at this position, the necessity of the carbonyl moiety, the length of the linker between the indole core and the naphthalene substituent, as well as the necessity of the hydroxyl moiety on the 7-position of the indole ring. Throughout our investigation twenty-one analogues were synthesized and evaluated. The majority of the analogues tested exhibited affinity for both CB1R and CB2R. Out of all of the compounds tested, two analogues, TV-5-249 and TV-6-41, showed the most promise. Compounds TV-5-249 and TV-6-41 displayed similar affinity at both receptors, with Ki for TV-5-249 of 15.4 nM at CB1R and 10.9 nM at CB2R and Ki for TV-6-41 of 37.2 and 26.5 nM at CB1R and CB2R, respectively. In the AC-inhibition assay, both compound showed very little inhibition of AC-activity at CB1Rs. However, TV-5-249 and TV-6-41 both exhibited similar inhibition of AC-activity of 40-50% at CB2Rs. With these promising results, the two lead compounds were subjected to two in vivo models for alcohol abuse: oral self-administration and alcohol conditioned place preference. TV-5-249 was showed to decrease alcohol self administration, without affecting total fluid intake or mean body weight, which was seen with rimonabant. TV-6-41 however, was observed to decrease alcohol conditioned place preference in the same way as rimonabant, without the accompanied inverse agonist activity.

Collectively these results demonstrate that JWH-073-derived compounds exhibiting cannabinoid activity that are devoid of inverse agonist activity can replicate the effects of rimonabant on alcohol self administration and conditioned place preference. A compound with a dual activity CB1R antagonist/CB2R agonist can indeed be a potential lead in the ongoing search for new alcohol abuse therapies.

Experimental Section

Unless otherwise indicated, all reagents were purchased from commercial sources and were used without further purification. Melting points were determined on a Thomas-Hoover capillary melting apparatus. NMR spectra were recorded on a Bruker DRX-400 with qnp probe or a Bruker AV-500 with cryoprobe using δ values in ppm (TMS as internal standard) and J (Hz) assignments of $^1$H resonance coupling. High resolution mass spectrometry data were collected on either a LCT Premier (Waters Corp., Milford, Mass.) time of flight mass spectrometer or an Agilent 6890 N gas chromatograph in conjunction with a quarto Micro GC mass spectrometer (Micromass Ltd, Manchester UK). Thin-layer chromatography (TLC) was performed on 0.25 mm plates Analtech GHLF silica gel plates using ethyl acetate/n-hexanes, in 20%:80% ratio as the solvent unless otherwise noted. Spots on TLC were visualized by UV (254 or 365 nm), if applicable, and phosphomolybdic acid in ethanol. Column chromatography was performed with Silica Gel (40-63μ particle size) from Sorbent Technologies (Atlanta, Ga.). Analytical HPLC was carried out on an Agilent 1100 Series Capillary HPLC system with diode array detection at 254 nm on an Agilent Eclipse XDB-C18 column (250×10 mm, 5 μm) with isocratic elution in 80% $CH_3CN$/20% $H_2O$ (0.1% Formic acid) unless otherwise specified.

1. General Procedure A: indole N-alkylation

To a suspension of KOH (5 equiv) in DMF (13 mL) was added 5- or 7-Methoxyindole (1 equiv). After stirring at R.T. for an hour, 1-bromobutane was added and the reaction mixture was heated to 50° C. and stirred overnight. Upon completion, the resulting mixture was poured into $H_2O$ and extracted with DCM. Combined organic extracts were washed with $H_2O$, dried over anhydrous $Na_2SO_4$ and concentrated in vacuo and the resulting residue was purified by flash column chromatography on silica gel using EtOAc/n-hexanes 1.1. 1-butyl-7-methoxy-1H-indole Compound 2 was synthesized from commercially available 7-Methoxyindole using the general procedure and 1-bromobutane to afford 0.51 g (74% yield) as a clear oil. TLC system: 10% EtOAc/90% n-hexanes. Spectral data matched previously reported data.[35]

1.2. 1-butyl-5-methoxy-1H-indole

Compound 7 was synthesized from commercially available 5-Methoxyindole using the general procedure and 1-bromobutane to afford 1.28 g (92% yield) as a clear oil. TLC system: 10% EtOAc/90% n-hexanes. $^1$H NMR (500 MHz, $CDCl_3$) δ 7.18 (d, J=8.9, 1H), 7.02 (dd, J=2.7, 13.3, 2H), 6.81 (dd, J=2.4, 8.9, 1H), 6.34 (dd, J=0.7, 3.0, 1H), 4.02 (t, J=7.1, 2H), 3.79 (s, 3H), 1.75 (ddd, J=7.3, 11.2, 14.8, 2H), 1.32-1.23 (m, 2H), 0.87 (t, J=7.4, 3H). $^{13}$C NMR (126 MHz, $CDCl_3$) δ 154.09, 131.56, 129.06, 128.55, 111.93, 110.35, 102.71, 100.53, 56.12, 46.54, 32.63, 20.43, 13.95. [M+H] calcd for $C_{13}H_{18}NO$, 204.1383. found 204.1386.

Preparation of 1-butyl-3-iodo-7-methoxy-1H-indole (Compound 10)

A round bottom flask containing indole (0.22 mL, 1.70 mmol, 1 equiv) in DMF at R.T. was stirred with KOH (0.10 g, 1.78 mmol, 1.05 equiv) for about 15 min and then treated with $I_2$ (0.44 g, 1.73 mmol, 1.02 equiv). After 30 min, NaH (0.082 g, 2.04 mmol, 1.2 equiv) was added portion-wise. After additional 15 min had passes 1-bromobutane (0.2 mL, 1.87 mmol, 1.1 equiv) was added and the reaction mixture was stirred until completion. Upon completion (TLC monitoring), $H_2O$ was added and allowed to stir for 15 min, upon which the mixture was extracted with DCM and the layers were separated. Aqueous layer was washed with DCM (3×) and the combined organic layers were washed with $H_2O$ (2×), dried over anhydrous $Na_2SO_4$ and concentrated in vacuo. The resulting residue was purified by silica gel column chromatography using EtOAc/n-hexanes to afford 0.449 g (80% yield) as an clear oil with a yellow tint. TLC system: 10% EtOAc/90% n-hexanes. $^1$H NMR (400 MHz, $CDCl_3$) δ 7.18 (d, J=8.8, 1H), 7.11 (s, 1H), 6.88 (dd, J=2.5, 8.8, 1H), 6.84 (d, J=2.4, 1H), 4.05 (t, J=7.1, 2H), 3.87 (d, J=3.7, 3H), 1.81-1.71 (m, 2H), 1.29 (tt, J=5.2, 10.1, 3H), 0.91 (t, J=7.4, 3H).

2. General Procedure B: O-Demethylation procedure

A solution of $BBr_3$ (1 M, 6 equiv) in DCM was added dropwise to a solution of methyl ether (1 equiv) also in DCM at −78° C. The mixture was then allowed to warm up to R.T. overnight, and upon completion NaCO₃ (6 equiv) was added. The resulting mixture was then cooled to 0° C. and MeOH (20 mL) was added dropwise and then stirred at 0° C. for 30 min. The reaction mixture was then warmed up to R. T. and stirred for an additional hour. Upon that, the reaction was then quenched with H₂O and the separated aqueous phase was washed with DCM (3×). Combined organic extracts were dried over anhydrous Na₂SO₄, concentrated in vacuo. The resulting residue was purified by flash chromatography on silica gel using mixtures of EtOAc/n-hexanes.

3. General Procedure C: 3'-Indole Acylation Procedure

To a solution of indole (1 equiv) in DCM at 0° C. under an Ar atmosphere was added Me₂AlCl (1.5 equiv) dropwise and the solution was allowed to stir at that temperature for 30 min, after which a solution of the acid chloride (1.2 equiv) in DCM was added dropwise. Reaction was monitored by TLC and upon completion, was carefully poured into an ice-cold 1N HCl solution and then extracted with DCM (3×). Combined organic layers were then washed with NaCO₃ (3×), brine, dried over anhydrous Na₂SO₄. The solvent was evaporated in vacuo and the resulting residue was purified by flash column chromatography on silica gel using mixtures of EtOAc/n-hexanes to afford desired product.

General Procedure D: Suzuki Coupling

Indole (1 equiv) and Pd(PPh₃)₄ (0.03 equiv) were placed into a round bottom flask and flushed with Ar (2×). Solvent (DME, 6 mL) was then added and allowed to stir for 10 min upon which the solution was degassed with Ar for 15 min Sodium carbonate (2 equiv) and boronic acid (1.5 equiv) in EtOH (1 mL) were added and the reaction mixture was refluxed. Reaction was monitored via TLC and upon completion, it was allowed to cool to R.T. and EtOAc was added. Mixture was then filtered through a pad of Celite and concentrated. The resulting residue was purified by flash column chromatography on silica gel using mixtures of EtOAc/n-hexanes.

General Procedure E: Acid Chloride Formation

Acid (1 equiv) was placed in a round bottom flask and flushed with Ar (2×). Anhydrous DCM (7 mL) was then added followed by the dropwise addition of oxalyl chloride (2 M in DCM, 3.1 equiv). After a few minutes, a few drops of anhydrous DMF were added to the reaction mixture and once the fizzing stopped, the reaction was allowed to stir overnight at R.T. Solvent was then evaporated using reduced pressure and the crude residue was used right away without any further purification.

3.1. 1-(1-butyl-7-methoxy-1H-indol-3-yl)-2-(4-fluorophenyl)ethanone (Compound 13/TV-6-129)

Compound 13 was synthesized from compound 2 using general procedure E and 4-fluorophenylacetyl chloride to afford 0.078 g (9% yield) isolated as a brown oil. ¹H NMR (500 MHz, CDCl₃) δ 7.98 (dd, J=0.8, 8.1, 1H), 7.64 (s, 1H), 7.29-7.25 (m, 2H), 7.16 (t, J=8.0, 1H), 7.02-6.96 (m, 2H), 6.71 (d, J=7.5, 1H), 4.39 (t, J=7.2, 2H), 4.09 (s, 2H), 3.93 (s, 3H), 1.85-1.77 (m, 2H), 1.36-1.27 (m, 2H), 0.94 (t, J=7.4, 3H). ¹³C NMR (126 MHz, CDCl₃) δ 192.32, 162.72, 160.77, 147.31, 135.78, 131.58, 131.55, 130.88, 130.82, 129.07, 126.33, 123.30, 115.76, 115.38, 115.21, 115.12, 104.31, 55.36, 50.28, 45.87, 33.81, 19.78, 13.68. HRMS (m/z): [M-K] calcd for C₂₁H₂₂FKNO₂, 378.1272. found 378.1315. HPLC t_R=15.031 min; purity=95.35% using 70% CH₃CN/30% H₂O (0.1% Formic acid).

3.2. 1-(1-butyl-7-methoxy-1H-indol-3-yl)-2-(4-methoxyphenyl)ethanone (Compound 15/TV-5-131)

Compound 15 was synthesized from compound 2 using general procedure E and 4-methoxyphenylacetyl chloride to afford 0.63 g (59.2% yield) isolated as a reddish solid, mp=72-74° C. ¹H NMR (500 MHz, CDCl₃) δ 8.00 (dd, J=0.8, 8.1, 1H), 7.63 (s, 1H), 7.25-7.21 (m, 2H), 7.15 (t, J=8.0, 1H), 6.87-6.81 (m, 2H), 6.70 (d, J=7.8, 1H), 4.37 (t, J=7.2, 2H), 4.06 (s, 2H), 3.92 (s, 3H), 3.77 (s, 3H), 1.84-1.76 (m, 2H), 1.35-1.26 (m, 2H), 0.93 (t, J=7.4, 3H). ¹³C NMR (126 MHz, CDCl₃) δ 193.44, 158.73, 147.69, 136.29, 130.73, 129.59, 128.50, 126.69, 123.58, 116.22, 115.62, 114.40, 104.62, 55.76, 55.69, 50.63, 46.48, 34.22, 20.19, 14.11. HRMS (m/z): [M+Na] calc for C₂₂H₂₅NNaO₃, 374.1732. found 374.1783. HPLC t_R=7.490 min; purity=99.92%.

3.3. 1-(1-butyl-7-hydroxy-1H-indol-3-yl)-2-(4-fluorophenyl)ethanone (Compound 14/TV-5-175)

Compound 14 was synthesized from compound 3 using general procedure B to afford 0.1 g (38% yield) isolated as an off-brown solid, mp=decomposition at 204-206° C. ¹H NMR (500 MHz, DMSO) δ 9.91 (s, 1H), 8.44 (s, 1H), 7.62 (dd, J=0.9, 8.0, 1H), 7.39-7.33 (m, 2H), 7.12 (ddd, J=2.6, 5.9, 8.9, 2H), 6.94 (t, J=7.8, 1H), 6.61 (dd, J=0.9, 7.7, 1H), 4.44 (t, J=7.0, 2H), 4.09 (s, 2H), 1.85-1.75 (m, 2H), 1.31-1.21 (m, 2H), 0.90 (t, J=7.4, 3H). ¹³C NMR (126 MHz, DMSO) δ 191.61, 161.72, 159.80, 144.49, 137.94, 132.50, 132.48, 131.05, 130.99, 128.73, 125.46, 122.80, 114.76, 114.59, 114.50, 112.34, 108.26, 48.70, 44.52, 33.29, 18.97, 13.39. HRMS (m/z): [M+Na+CH₃CN] calc for C₂₂H₂₃FN²NaO₂, 389.1641. found 389.1711. HPLC t_R=6.491 min; purity=99.91% using 70% CH₃CN/30% H₂O (0.1% Formic acid).

3.4. 1-(1-butyl-7-methoxy-1H-indol-3-yl)-2-phenylethanone (Compound 17/TV-5-179)

Compound 17 was synthesized from compound 2 using general procedure C and phenylacetyl chloride to afford 0.133 g (17% yield) isolated as an off-white solid with a pinkish tint, mp=65-68° C. ¹H NMR (500 MHz, CDCl₃) δ 8.03 (dd, J=0.8, 8.1, 1H), 7.66 (s, 1H), 7.36-7.30 (m, 4H), 7.26-7.22 (m, 1H), 7.18 (t, J=8.0, 1H), 6.72 (d, J=7.8, 1H), 4.39 (t, J=7.2, 2H), 4.14 (s, 2H), 3.94 (s, 3H), 1.87-1.77 (m, 2H), 1.32 (dq, J=7.4, 14.8, 2H), 0.95 (t, J=7.4, 3H). ¹³C NMR (126 MHz, CDCl₃) δ 192.72, 147.37, 136.13, 136.06, 129.43, 129.25, 128.62, 126.64, 126.38, 123.30, 115.96, 115.30, 104.34, 55.44, 50.32, 47.09, 33.88, 19.86, 13.78. HRMS (m/z): [M+Na] calc for C₂₁H₂₃NNaO₂, 344.1626. found 344.1656. HPLC t_R=8.114 min; purity=99.85%.

3.5. 1-(1-butyl-7-hydroxy-1H-indol-3-yl)-2-phenylethanone (Compound 18/TV-5-189)

Compound 18 was synthesized from compound 3 using general procedure B to afford 0.168 g (68% yield) isolated as a fluffy brown solid, mp=decomposition at 197-200° C. ¹H NMR (500 MHz, DMSO) δ 9.91 (s, 1H), 8.44 (s, 1H), 7.62 (dd, J=0.9, 8.0, 1H), 7.36-7.31 (m, 2H), 7.28 (dd, J=4.9, 10.3, 2H), 7.20 (dd, J=4.3, 11.6, 1H), 6.93 (t, J=7.8, 1H), 6.61 (dd, J=0.9, 7.7, 1H), 4.44 (t, J=7.0, 2H), 4.08 (s, 2H), 1.84-1.75 (m, 2H), 1.30-1.20 (m, 2H), 0.90 (t, J=7.4, 3H). $^{13}$C NMR (126 MHz, DMSO) δ 191.75, 144.49, 137.99, 136.39, 129.20, 128.76, 128.00, 126.01, 125.46, 122.77, 114.60, 112.35, 108.24, 48.67, 45.62, 33.28, 18.95, 13.38. HRMS (m/z): [M+Na] calc for $C_{20}H_{21}NNaO_2$, 330.1470. found 330.1514. HPLC $t_R$=6.458 min; purity=99.84% using 70% $CH_3CN$/30% $H_2O$ (0.1% Formic acid).

3.6. 1-(1-butyl-7-methoxy-1H-indol-3-yl)-2-(naphthalen-1-yl)ethanone (Compound 19/TV-5-203)

Compound 19 was synthesized from compound 2 using general procedure C and 1-naphthoylacetyl chloride to afford 0.095 g (12% yield) isolated as an amorphous yellow solid, mp=110-113° C. $^1$H NMR (500 MHz, CDCl$_3$) δ 8.07-8.00 (m, 2H), 7.89-7.85 (m, 1H), 7.79 (dd, J=2.4, 7.0, 1H), 7.72 (s, 1H), 7.51-7.46 (m, 2H), 7.46-7.43 (m, 2H), 7.18 (t, J=8.0, 1H), 6.73 (d, J=7.6, 1H), 4.61 (s, 2H), 4.38 (t, J=7.1, 2H), 3.95 (s, 3H), 1.85-1.77 (m, 2H), 1.34-1.24 (m, 2H), 0.94 (t, J=7.4, 3H). $^{13}$C NMR (126 MHz, CDCl$_3$) δ 192.76, 147.41, 135.82, 133.97, 132.76, 132.55, 129.27, 128.76, 127.93, 127.63, 126.32, 126.30, 125.73, 125.57, 124.28, 123.31, 115.99, 115.33, 104.33, 55.45, 50.32, 44.80, 33.84, 19.84, 13.77. HRMS (m/z): [1\4+K] calc for $C_{25}H_{25}KNO_2$, 410.1522. found 410.1527. HPLC $t_R$=11.439 min; purity=99.82%.

3.7. 1-(1-butyl-7-hydroxy-1H-indol-3-yl)-2-(naphthalen-1-yl)ethanone (Compound 20/TV-5-209)

Compound 20 was synthesized from compound 3 using general procedure B to afford 0.070 g (55% yield) isolated as an off brown solid, mp=decomposition at 213-216° C. TLC system: 30% EtOAc/70% n-hexanes. $^1$H NMR (500 MHz, DMSO) δ 9.32 (s, 1H), 8.85 (s, 1H), 8.65-8.58 (m, 1H), 8.39-8.33 (m, 1H), 8.28 (dt, J=4.3, 8.6, 2H), 8.00-7.88 (m, 4H), 7.42 (t, J=7.8, 1H), 7.15 (d, J=7.6, 1H), 5.13 (s, 2H), 5.02 (t, J=7.1, 2H), 2.41-2.33 (m, 2H), 1.81 (dq, J=7.4, 14.9, 2H), 1.40 (t, J=7.4, 3H). $^{13}$C NMR (126 MHz, DMSO) δ 191.47, 144.32, 136.79, 133.93, 133.52, 132.76, 129.74, 128.34, 128.04, 127.00, 125.69, 125.40, 125.36, 124.74, 122.71, 115.59, 113.81, 108.35, 49.30, 43.73, 33.85, 19.44, 13.07. HRMS (m/z): [M+Na+CH$_3$CN] calc for $C_{26}H_{26}N_2NaO_2$, 421.1892. found 421.1924. HPLC $t_R$=6.458 min; purity=99.84% using 70% $CH_3CN$/30% $H_2O$ (0.1% Formic acid).

3.8. (1-butyl-5-methoxy-1H-indol-3-yl)(naphthalen-1-yl)methanone (Compound 21/TV-5-235)

Compound 21 was synthesized from compound 7 using general procedure C and 1-naphthoylacetyl chloride to afford 0.357 g (16% yield) isolated as an amorphous yellow oil. $^1$H NMR (500 MHz, CDCl$_3$) δ 8.18 (d, J=8.5, 1H), 8.01 (d, J=2.5, 1H), 7.96 (d, J=8.2, 1H), 7.90 (d, J=7.6, 1H), 7.64 (dd, J=1.2, 7.0, 1H), 7.54-7.44 (m, 3H), 7.28 (d, J=2.2, 1H), 7.25 (s, 1H), 6.98 (dd, J=2.6, 8.9, 1H), 4.02 (t, J=7.2, 2H), 3.92 (s, 3H), 1.81-1.71 (m, 2H), 1.32-1.22 (m, 2H), 0.88 (t, J=7.4, 3H). $^{13}$C NMR (126 MHz, CDCl$_3$) δ 192.12, 156.75, 139.25, 138.00, 133.81, 131.99, 130.88, 129.96, 128.24, 127.90, 126.80, 126.37, 126.11, 125.83, 124.65, 117.25, 114.28, 110.95, 103.99, 55.93, 47.23, 31.95, 20.11, 13.65. HRMS (m/z): [M+Na] calc for $C_{26}H_{26}N_2NaO_2$, 421.1892. found 421.1930. HPLC $t_R$=16.771 min; purity=99.94% using 70% $CH_3CN$/30% $H_2O$ (0.1% Formic acid).

3.9. (1-butyl-5-hydroxy-1H-indol-3-yl)(naphthalen-1-yl)methanone (Compound 22/TV-5-241)

Compound 22 was synthesized from compound 8 using general procedure B to afford 0.595 g (90% yield) isolated as an lightly yellow solid, mp=209-212° C. TLC system: 30% EtOAc/70% n-hexanes. $^1$H NMR (500 MHz, DMSO) δ 9.20 (s, 1H), 8.07 (d, J=7.8, 1H), 8.02 (d, J=7.9, 1H), 7.98 (d, J=8.5, 1H), 7.74 (d, J=2.4, 1H), 7.65-7.59 (m, 3H), 7.58-7.54 (m, 1H), 7.50 (ddd, J=1.4, 6.8, 8.2, 1H), 7.41 (d, J=8.8, 1H), 6.80 (dd, J=2.4, 8.8, 1H), 4.11 (t, J=7.2, 2H), 1.69-1.61 (m, 2H), 1.23-1.14 (m, 2H), 0.81 (t, J=7.4, 3H). $^{13}$C NMR (126 MHz, DMSO) δ 190.38, 153.63, 138.93, 138.61, 133.14, 130.83, 129.92, 129.30, 128.09, 127.39, 126.46, 126.06, 125.31, 125.20, 124.82, 115.24, 112.81, 111.40, 106.01, 45.86, 31.33, 19.16, 13.27. HRMS (m/z): [M+Na+CH$_3$CN] calc for $C_{25}H_{24}N_2NaO_2$, 407.1735. found 407.1777. HPLC $t_R$=13.460 min; purity=100.00% using 60% $CH_3CN$/40% $H_2O$ (0.1% Formic acid).

3.10. 1-butyl-7-methoxy-3-(naphthalen-1-ylmethyl)-1H-indole (TV-5-249) (Compound 25/TV-5-249)

LiAlH$_4$ (4.9 mL, 4.85 mmol, 4 equiv) was dissolved in THF (1M) and a solution of AlCl$_3$ (1.94 g, 14.54 mmol, 12 equiv) in THF (8 mL) was added dropwise at 0° C. After 30 min, indole (0.433 g, 1.21 mmol, 1 equiv) in THF (9 mL) was added to the reaction mixture and allowed to stir at R.T. for 48 hrs. Upon completion, reaction mixture was cooled to 0° C. and carefully quenched with H$_2$O and acidified with 1 N HCl to pH=3. The organic phase was then separated and washed with NaCO$_3$ and brine, dried over anhydrous NaSO$_4$. The solvent was evaporated in vacuo and the resulting residue was purified by flash column chromatography on silica gel using mixtures of EtOAc/n-hexanes to afford 0.073 g (18% yield) isolated as an pinkish oil. TLC system: 10% EtOAc/90% n-hexanes. $^1$H NMR (500 MHz, CDCl$_3$) δ 8.11 (d, J=8.0, 1H), 7.91-7.85 (m, 1H), 7.76 (d, J=8.0, 1H), 7.46 (tt, J=3.5, 8.3, 2H), 7.42-7.34 (m, 2H), 7.21 (dd, J=0.8, 8.0, 1H), 7.00 (t, J=7.8, 1H), 6.65 (d, J=7.5, 1H), 6.50 (s, 1H), 4.51 (s, 2H), 4.24 (t, J=7.2, 2H), 3.94 (s, 3H), 1.70 (dt, J=7.4, 14.8, 2H), 1.24 (dq, J=7.4, 14.7, 2H), 0.87 (t, J=7.4, 3H). $^{13}$C NMR (126 MHz, CDCl$_3$) δ 147.93, 137.47, 134.22, 132.61, 130.65, 128.93, 128.32, 127.11, 126.92, 126.31, 126.09, 126.05, 125.83, 124.87, 119.55, 113.82, 112.31, 102.72, 55.68, 49.26, 34.70, 29.37, 20.24, 14.16. HRMS (m/z): [M$^+$] calc for $C_{24}H_{25}NO$, 343.1936. found 343.1887. HPLC $t_R$=12.038 min; purity=99.92% using 90% $CH_3CN$/10% $H_2O$ (0.1% Formic acid).

3.11. (7-methoxy-1-(2-morpholinoethyl)-1H-indol-3-yl)(naphthalen-1-yl)methanone (Compound 26/TV-6-17)

Compound 26 was synthesized from compound 2 using general procedure C and 1-naphthoylacetyl chloride to afford 0.161 g (16% yield) isolated as an yellow solid, mp=149-152° C. TLC system: 50% EtOAc/50% n-hexanes. $^1$H NMR (500 MHz, CDCl$_3$) δ 8.18-8.10 (m, 2H), 7.95 (d, J=8.2, 1H), 7.89 (d, J=7.5, 1H), 7.63 (dd, J=1.2, 7.0, 1H), 7.54-7.41 (m, 3H), 7.27-7.23 (m, 3H), 6.77 (d, J=7.4, 1H), 4.40 (t, J=6.5, 2H), 3.94 (s, 3H), 3.60-3.49 (m, 4H), 2.67 (t, J=6.6, 2H), 2.42-2.33 (m, 4H). $^{13}$C NMR (126 MHz, CDCl$_3$) δ 192.18, 147.29, 140.00, 139.28, 133.80, 130.86, 130.00, 129.34, 128.26, 126.86, 126.45, 126.38, 126.06, 125.82, 124.55, 123.67, 117.60, 115.47, 104.70, 66.99, 59.29, 55.48, 53.77, 47.37. HRMS (m/z): [M+H] calc for $C_{26}H_{27}N_2O_3^+$, 415.2016. found 415.1985. HPLC $t_R$=7.049 min; purity=95.02% using 30% $CH_3CN$/70% $H_2O$ (0.1% Formic acid).

3.12. 1-(1-butyl-7-hydroxy-1H-indol-3-yl)-2-(4-hydroxyphenyl)ethanone (Compound 16/TV-6-25)

Compound 16 was synthesized from compound 3 using general procedure B to afford 0.047 g (17% yield) isolated as an off-white solid, mp=decomposition at 197-200° C. TLC system: 30% EtOAc/70% n-hexanes. $^1$H NMR (500 MHz, Acetone) δ 8.86 (s, 1H), 8.23 (s, 1H), 8.16 (s, 1H), 7.86 (dd, J=0.9, 8.0, 1H), 7.21 (d, J=8.6, 2H), 6.98 (t, J=7.8, 1H), 6.80-6.73 (m, 2H), 6.68 (dd, J=0.9, 7.6, 1H), 4.54 (t, J=7.1, 2H), 4.01 (s, 2H), 1.94-1.85 (m, 2H), 1.39-1.29 (m, 2H), 0.94 (t, J=7.4, 3H). $^{13}$C NMR (126 MHz, Acetone) δ 193.14, 156.81, 145.21, 137.93, 131.20, 130.75, 128.46, 126.87, 123.57, 116.43, 115.91, 115.82, 114.76, 109.25, 50.17, 46.31, 34.79, 20.37, 13.99. HRMS (m/z): [M+Na] calc for $C_{22}H_{24}N_2NaO_3$, 387.1685. found 387.1658. HPLC $t_R$=4.998 min; purity=99.41% using 60% $CH_3CN$/40% $H_2O$ (0.1% Formic acid).

3.13. 1-butyl-7-methoxy-3-(naphthalen-2-yl)-1H-indole (Compound 12/24/TV-6-41)

Compound 12/24 was synthesized from compound 10 using general method D to afford 0.036 g (8% yield) isolated as an clear oil. TLC system: 10% DCM/90% n-hexanes. $^1$H NMR (500 MHz, CDCl$_3$) δ 8.10 (s, 1H), 7.93-7.84 (m, 4H), 7.80 (dd, J=1.8, 8.4, 1H), 7.65 (dt, J=3.2, 6.3, 1H), 7.47 (dddd, J=1.3, 6.9, 8.0, 16.2, 2H), 7.29 (s, 1H), 7.12 (t, J=7.9, 1H), 6.72 (d, J=7.7, 1H), 4.46 (t, J=7.2, 2H), 3.99 (s, 3H), 1.92-1.83 (m, 2H), 1.45-1.36 (m, 2H), 0.98 (t, J=7.4, 3H). $^{13}$C NMR (126 MHz, CDCl$_3$) δ 147.84, 134.10, 133.46, 131.93, 128.72, 128.20, 127.80, 127.75, 127.51, 126.71, 126.56, 126.12, 125.11, 125.07, 120.43, 116.57, 112.74, 102.83, 55.45, 49.49, 34.43, 20.06, 13.91. HRMS (m/z): [M$^+$] calc for $C_{23}H_{23}NO$, 329.1780. found 329.1747. HPLC $t_R$=12.570 min; purity=96.65% using 90% $CH_3CN$/10% $H_2O$ (0.1% Formic acid).

3.14. (1-butyl-7-methoxy-1H-indol-3-yl)(4-fluorophenyl)methanone (Compound 27/TV-6-47)

Compound 27 was synthesized from compound 2 using general procedure C and 4-fluorobenzoyl chloride to afford 0.278 g (49% yield) isolated as an pinkish solid, mp=91-94° C. $^1$H NMR (500 MHz, CDCl$_3$) δ 8.02 (dd, J=0.8, 8.0, 1H), 7.89-7.84 (m, 2H), 7.45 (s, 1H), 7.26 (t, J=8.0, 1H), 7.22-7.17 (m, 2H), 6.80 (d, J=7.4, 1H), 4.44 (t, J=7.2, 2H), 4.00 (s, 3H), 1.91-1.81 (m, 2H), 1.43-1.32 (m, 2H), 0.98 (t, J=7.4, 3H). $^{13}$C NMR (126 MHz, CDCl$_3$) δ 189.45, 165.64, 163.64, 147.43, 137.73, 137.34, 137.32, 131.17, 131.10, 129.80, 126.50, 123.39, 115.45, 115.31, 115.28, 115.13, 104.57, 55.49, 50.37, 33.97, 19.90, 13.79. HRMS (m/z): [M+Na+CH$_3$CN] calc for $C_{22}H_{23}FN_2NaO_2$, 389.1641. found 389.1608. HPLC $t_R$=8.765 min; purity=99.81%.

3.15. 1-(1-butyl-7-methoxy-1H-indol-3-yl)-2-(2-fluorophenyl)ethanone (Compound 30/TV-6-79)

Compound 30 was synthesized from compound 2 using general method C and an acid chloride made in situ from 2-(2-fluorophenyl)acetic acid to afford 0.301 g (35% yield) isolated as a darker yellow solid, mp=86-88° C. $^1$H NMR (500 MHz, CDCl$_3$) δ 8.04 (dd, J=0.8, 8.1, 1H), 7.78 (s, 1H), 7.41 (td, J=1.7, 7.6, 1H), 7.29-7.23 (m, 1H), 7.21 (t, J=8.0, 1H), 7.16-7.07 (m, 2H), 6.75 (d, J=7.4, 1H), 4.44 (t, J=7.2, 2H), 4.20 (s, 2H), 3.97 (s, 3H), 1.91-1.82 (m, 2H), 1.42-1.32 (m, 2H), 0.99 (t, J=7.4, 3H). $^{13}$C NMR (126 MHz, CDCl$_3$) δ 190.37, 160.78, 158.83, 146.34, 135.04, 135.03, 130.71, 130.67, 128.14, 127.54, 127.48, 125.39, 123.22, 123.19, 122.30, 122.13, 122.01, 114.61, 114.37, 114.19, 114.17, 103.31, 54.40, 49.30, 38.49, 38.48, 32.82, 18.80, 12.73. [M+Na] calc for $C_{21}H_{22}FNNaO_2$, 362.1532. found 362.1513. HPLC $t_R$=8.732 min; purity=99.57%.

3.16. 1-(1-butyl-7-methoxy-1H-indol-3-yl)-2-(3-fluorophenyl)ethanone (Compound 28/TV-6-85)

Compound 28 was synthesized from compound 2 using general method C and an acid chloride made in situ from 2-(3-fluorophenyl)acetic acid to afford 0.208 g (27% yield) isolated as an yellow oil. $^1$H NMR (500 MHz, CDCl$_3$) δ 7.98 (dd, J=0.8, 8.1, 1H), 7.63 (s, 1H), 7.28-7.21 (m, 2H), 7.16 (t, J=8.0, 1H), 7.08 (d, J=8.1, 1H), 7.03 (d, J=9.8, 1H), 6.91 (td, J=1.8, 8.3, 1H), 6.71 (d, J=7.5, 1H), 4.38 (t, J=7.2, 2H), 4.10 (s, 2H), 3.92 (s, 3H), 1.85-1.75 (m, 2H), 1.36-1.25 (m, 2H), 0.93 (t, J=7.4, 3H). $^{13}$C NMR (126 MHz, CDCl$_3$) δ 191.85, 163.92, 161.97, 147.41, 138.42, 138.36, 135.97, 130.00, 129.94, 129.16, 126.44, 125.18, 125.16, 123.45, 116.54, 116.37, 115.86, 115.21, 113.69, 113.52, 104.46, 55.46, 50.40, 46.55, 46.54, 33.88, 19.87, 13.77. HRMS (m/z): [M+Na] calc for $C_{21}H_{22}FNNaO_2$, 362.1532. found 362.1503. HPLC $t_R$=13.931 min; purity=99.93% using 50% $CH_3CN$/50% $H_2O$ (0.1% Formic acid).

3.17. 1-(1-butyl-7-ethyl-1H-indol-3-yl)-2-(4-fluorophenyl)ethanone (Compound 29/TV-6-93)

Compound 29 was synthesized from compound 2 using general method C and 4-fluorophenylacetyl chloride to afford 0.335 g (39% yield) isolated as a white powder, mp=67-70° C. $^1$H NMR (500 MHz, CDCl$_3$) δ 8.34 (dd, J=1.2, 8.0, 1H), 7.72 (s, 1H), 7.32-7.27 (m, 2H), 7.25-7.20 (m, 1H), 7.10 (d, J=6.5, 1H), 7.04-6.98 (m, 2H), 4.35-4.28 (m, 2H), 4.12 (s, 2H), 3.02 (q, J=7.5, 2H), 1.87-1.78 (m, 2H), 1.42-1.32 (m, 5H), 0.98 (t, J=7.4, 3H). $^{13}$C NMR (126 MHz, CDCl$_3$) δ 192.35, 162.81, 160.87, 136.80, 134.58, 131.73, 131.70, 130.95, 130.88, 128.22, 127.79, 124.78, 123.06, 120.82, 115.82, 115.50, 115.33, 49.80, 46.00, 34.07, 25.52, 20.01, 16.28, 13.75. HRMS (m/z): [M+Na+CH$_3$CN] calc for $C_{24}H_{27}FN_2NaO$, 401.2005. found 401.1976. HPLC $t_R$=9.645 min; purity=99.89%.

3.18. 1-butyl-7-methoxy-3-(naphthalen-1-yl)-1H-indole (Compound 11/23/TV-6-95)

Compound 11/23 was synthesized from compound 10 using general method D to afford 0.173 g (37% yield) isolated as a yellow solid, mp=74-76° C. TLC system: 10% DCM/90% n-hexanes. $^1$H NMR (500 MHz, CDCl$_3$) δ 8.10 (d, J=8.2, 1H), 7.92 (d, J=8.2, 1H), 7.85 (d, J=8.0, 1H), 7.53 (dddd, J=1.3, 6.9, 8.1, 23.6, 3H), 7.41 (ddd, J=1.3, 6.8, 8.2, 1H), 7.19 (s, 1H), 7.09 (dd, J=0.9, 8.0, 1H), 7.00 (t, J=7.8, 1H), 6.70 (d, J=7.3, 1H), 4.50 (t, J=7.1, 2H), 4.01 (s, 3H), 1.95-1.86 (m, 2H), 1.47-1.37 (m, 2H), 0.99 (t, J=7.4, 3H). $^{13}$C NMR (126 MHz, CDCl$_3$) δ 147.75, 134.08, 133.36, 132.64, 130.54, 128.76, 128.28, 127.75, 126.92, 126.80, 125.90, 125.70, 125.67, 125.65, 119.90, 114.86, 113.25, 102.56, 55.47, 49.36, 34.47, 20.08, 13.93. HRMS (m/z): [M$^+$] calc for $C_{23}H_{23}NO$, 329.1780. found 329.1747. HPLC $t_R$=11.727 min; purity=95.35% using 90% $CH_3CN$/10% $H_2O$ (0.1% Formic acid).

3.19. 1-(1-butyl-7-methoxy-1H-indol-3-yl)-2-(3,4-difluorophenyl)ethanone (Compound 31/TV-6-101)

Compound 31 was synthesized from compound 2 using general method C and an acid chloride made in situ from 2-(3,4-difluorophenyl)acetic acid to afford 0.067 g (8% yield) isolated as an off-white solid, mp=88-90° C. $^1$H NMR (500 MHz, CDCl3) δ 8.01 (dd, J=0.8, 8.1, 1H), 7.68 (s, 1H), 7.21 (t, J=8.0, 1H), 7.19-7.14 (m, 1H), 7.14-7.09 (m, 1H), 7.06 (d, J=2.2, 1H), 6.76 (d, J=7.8, 1H), 4.44 (t, J=7.2, 2H), 4.11 (s, 2H), 3.97 (s, 3H), 1.92-1.79 (m, 2H), 1.37 (dq, J=7.4, 14.8, 2H), 0.99 (t, J=7.4, 3H). $^{13}$C NMR (126 MHz, CDCl$_3$) δ 191.44, 150.14 (dd, J=247.8, 12.8 Hz), 149.30 (dd, J=246.7, 12.6 Hz), 147.32, 135.70, 132.64 (dd, J=6.0, 4.0 Hz), 128.98, 126.38, 125.38 (dd, J=6.1, 3.6 Hz), 123.43, 118.36 (d, J=17.3 Hz), 117.08 (d, J=17.1 Hz), 115.66, 115.02, 104.41, 55.37, 50.34, 46.07-44.76 (m), 33.81, 19.80, 13.68. HRMS (m/z): [M+Na+$CH_3CN$] calc for $C_{23}H_{24}F_2N_2NaO_2$, 421.1704. found 421.1678. HPLC $t_R$=8.678 min; purity=100.00%.

3.20. 1-(1-butyl-7-methoxy-1H-indol-3-yl)-2-(2,3-difluorophenyl)ethanone (Compound 32/TV-6-115)

Compound 32 was synthesized from compound 2 using general method C and an acid chloride made in situ from 2-(2,3-difluorophenyl)acetic acid to afford 0.230 g (24% yield) isolated as an off-brown solid. $^1$H NMR (500 MHz, CDCl3) δ 8.02 (dd, J=0.8, 8.1, 1H), 7.78 (s, 1H), 7.21 (t, J=8.0, 1H), 7.16 (t, J=6.7, 1H), 7.13-7.03 (m, 2H), 6.76 (d, J=7.4, 1H), 4.45 (t, J=7.2, 2H), 4.23 (d, J=1.3, 2H), 3.98 (s, 3H), 1.92-1.83 (m, 2H), 1.43-1.33 (m, 2H), 0.99 (t, J=7.4, 3H). $^{13}$C NMR (126 MHz, CDCl$_3$) δ 190.40, 150.68 (dd, J=222.0, 13.0 Hz), 148.72 (dd, J=220.5, 13.1 Hz), 147.32, 135.89 (d, J=1.6 Hz), 129.00, 126.37, 126.29 (t, J=3.2 Hz), 125.38 (d, J=12.6 Hz), 123.91 (dd, J=6.9, 4.6 Hz), 123.37, 115.65 (d, J=17.1 Hz), 115.44, 115.03, 104.36, 55.36, 50.32, 39.10 (t, J=1.8 Hz), 33.78, 19.76, 13.67. HRMS (m/z): [M+Na+$CH_3CN$] calc for $C_{23}H_{24}F_2N_2NaO_2$, 421.1704. found 421.1687. HPLC $t_R$=8.827 min; purity=100.00%.

3.21. 1-(1-butyl-7-methoxy-1H-indol-3-yl)-2-(2,3-difluorophenyl)ethanone (Compound 33/TV-5-157)

Compound 33 was synthesized from compound 2 using general method C and 1-naphthoyl chloride to afford 2.0 g (53% yield) isolated as pale brown solid, mp=108-110° C. $^1$H NMR (500 MHz, CDCl$_3$) δ 8.19 (d, J=8.4, 1H), 8.11 (d, J=7.4, 1H), 7.96 (d, J=8.2, 1H), 7.91 (d, J=7.8, 1H), 7.65 (dd, J=1.1, 7.0, 1H), 7.56-7.45 (m, 3H), 7.28-7.24 (m, 2H), 7.22 (s, 1H), 6.79 (d, J=7.7, 1H), 4.30 (t, J=7.3, 2H), 3.96 (s, 3H), 1.80-1.71 (m, 2H), 1.32-1.23 (m, 2H), 0.89 (t, J=7.4, 3H). $^{13}$C NMR (126 MHz, CDCl$_3$) δ 192.08, 147.45, 139.32, 139.07, 133.81, 130.89, 129.96, 129.46, 128.22, 126.79, 126.61, 126.34, 126.14, 125.89, 124.65, 123.60, 117.42, 115.35, 104.66, 55.50, 50.34, 33.86, 19.83, 13.73. HRMS (m/z): [M+Na+$CH_3CN$] calc for $C_{26}H_{26}N_2NaO_2$ 421.1892. found 421.1843. HPLC $t_R$=14.576; purity=95.821%.

REFERENCES

[1] Jarbe T U, DiPatrizio N V. Delta9-THC induced hyperphagia and tolerance assessment: interactions between the CB1 receptor agonist delta9-THC and the CB1 receptor antagonist SR-141716 (rimonabant) in rats. Behavioural pharmacology 2005; 16:373-80.

[2] Colombo G, Agabio R, Diaz G, Lobina C, Reali R, Gessa G L. Appetite suppression and weight loss after the cannabinoid antagonist SR 141716. Life sciences 1998; 63:PL113-7.

[3] Despres J P, Ross R, Boka G, Almeras N, Lemieux I. Effect of rimonabant on the high-triglyceride/low-HDL-cholesterol dyslipidemia, intraabdominal adiposity, and liver fat: the ADAGIO-Lipids trial. Arteriosclerosis, thrombosis, and vascular biology 2009; 29:416-23.

[4] Pi-Sunyer F X, Aronne U, Heshmati H M, Devin J, Rosenstock J. Effect of rimonabant, a cannabinoid-1 receptor blocker, on weight and cardiometabolic risk factors in overweight or obese patients: RIO-North America: a randomized controlled trial. Jama 2006; 295:761-75.

[5] Vardakou I, Pistos C, Spiliopoulou C. Spice drugs as a new trend: mode of action, identification and legislation. Toxicol Lett 2010; 197:157-62.

[6] Auwarter V, Dresen S, Weinmann W, Muller M, Putz M, Ferreiros N. 'Spice' and other herbal blends: harmless incense or cannabinoid designer drugs? J Mass Spectrom 2009; 44:832-7.

[7] Seely K A, Prather P L, James L P, Moran J H. Marijuana-based drugs: innovative therapeutics or designer drugs of abuse? Mol Interv 2011; 11:36-51.

[8] Hudson S, Ramsey J, King L, Timbers S, Maynard S, Dargan P I, et al. Use of high-resolution accurate mass spectrometry to detect reported and previously unreported cannabinomimetics in "herbal high" products. J Anal Toxicol 2010; 34:252-60.

[9] Vandrey R, Dunn K E, Fry J A, Girling E R. A survey study to characterize use of Spice products (synthetic cannabinoids). Drug Alcohol Depend 2011.

[10] Vearrier D, Osterhoudt K C. A teenager with agitation: higher than she should have climbed. Pediatr Emerg Care 2010; 26:462-5.

[11] Muller H, Sperling W, Kohrmann M, Huttner H B, Kornhuber J, Maler J M. The synthetic cannabinoid Spice as a trigger for an acute exacerbation of cannabis induced recurrent psychotic episodes. Schizophr Res 2010; 118:309-10.

[12] Muller H, Huttner H B, Kohrmann M, Wielopolski J E, Kornhuber J, Sperling W. Panic attack after spice abuse in a patient with ADHD. Pharmacopsychiatry 2010; 43:152-3.

[13] Every-Palmer S. Synthetic cannabinoid JWH-018 and psychosis: An explorative study. Drug Alcohol Depend 2011; 117:152-7.

[14] Young A C, Schwarz E, Medina G, Obafemi A, Feng S Y, Kane C, et al. Cardiotoxicity associated with the synthetic cannabinoid, K9, with laboratory confirmation. Am J Emerg Med 2011.

[15] Simmons J, Cookman L, Kang C, Skinner C. Three cases of "spice" exposure. Clin Toxicol (Phila) 2011; 49:431-3.

[16] Schneir A B, Cullen J, Ly B T. "Spice" girls: synthetic cannabinoid intoxication. J Emerg Med 2011; 40:296-9.

[17] Wehrman J. Fake Marijuana Spurs More than 4,500 Calls to U.S. Poison Centers. Alexandria, Va.: American Association of Poison Control Centers, 2011.

[18] Leonhart M M. Schedules of Controlled Substances: Temporary Placement of Five Synthetic Cannabinoids Into Schedule I. In: Justice UDo, editor: Federal Register, 2010. p. 71635-8.

[19] AAPCC. Synthetic Marijuana Data. 2011.

[20] Hu X, Primack B A, Barnett T E, Cook R L. College students and use of K2: an emerging drug of abuse in young persons. Subst Abuse Treat Prev Policy 2011; 6:16.

[21] Johnston L D O, Malley P M, Bachman J G, Schulenberg J E. Marijuana use continues to rise among U.S. teens, while alcohol use hits historic lows. In: Service UoMN, editor. Ann Arbor, Mich.: University of Michigan, 2011.

[22] Atwood B K, Huffman J, Straiker A, Mackie K. JWH018, a common constituent of 'Spice' herbal blends, is a potent and efficacious cannabinoid CB receptor agonist. Br J Pharmacol 2010; 160:585-93.

[23] Jarbe T U, Deng H, Vadivel S K, Makriyannis A. Cannabinergic aminoalkylindoles, including AM678=JWH018 found in 'Spice', examined using drug (Delta9-tetrahydrocannabinol) discrimination for rats. Behav Pharmacol 2011; 22:498-507.

[24] Wu H M, Yang Y M, Kim S G. Rimonabant, a CB1 Inverse Agonist, Inhibits Hepatocyte Lipogenesis by Activating LKB1 and AMPK Axis Downstream of G{alpha}i/o Inhibition. Mol Pharmacol 2011.

[25] Lindborg K A, Teachey M K, Jacob S, Henriksen E J. Effects of in vitro antagonism of endocannabinoid-1 receptors on the glucose transport system in normal and insulin-resistant rat skeletal muscle. Diabetes Obes Metab 2010; 12:722-30.

[26] Di Marzo V, Piscitelli F. Gut feelings about the endocannabinoid system. Neurogastroenterol Motil 2011; 23:391-8.

[27] Rossi F, Bellini G, Luongo L, Torella M, Mancusi S, De Petrocellis L, et al. The endovanilloid/endocannabinoid system: a new potential target for osteoporosis therapy. Bone 2011; 48:997-1007.

[28] Bari M, Battista N, Pirazzi V, Maccarrone M. The manifold actions of endocannabinoids on female and male reproductive events. Front Biosci 2011; 16:498-516.

[29] Dresen S, Ferreiros N, Putz M, Westphal F, Zimmermann R, Auwarter V. Monitoring of herbal mixtures potentially containing synthetic cannabinoids as psychoactive compounds. J Mass Spectrom 2010; 45:1186-94.

[30] Sobolevsky T, Prasolov I, Rodchenkov G. Detection of JWH-018 metabolites in smoking mixture post-administration urine. Forensic Sci Int 2010; 200:141-7.

[31] Chimalakonda K C, Moran C L, Kennedy P D, Endres G W, Uzieblo A, Dobrowolski P J, et al. Solid-Phase Extraction and Quantitative Measurement of Omega and Omega-1 Metabolites of JWH-018 and JWH-073 in Human Urine. Anal Chem 2011.

[32] Moran C L, Le V H, Chimalakonda K C, Smedley A L, Lackey F D, Owen S N, et al. Quantitative measurement of JWH-018 and JWH-073 metabolites excreted in human urine. Anal Chem 2011; 83:4228-36.

[33] Uchiyama N, Kikura-Hanajiri R, Ogata J, Goda Y. Chemical analysis of synthetic cannabinoids as designer drugs in herbal products. Forensic Sci Int 2010; 198:31-8.

[34] Penn H J, Langman U, Unold D, Shields J, Nichols J H. Detection of synthetic cannabinoids in herbal incense products. Clin Biochem 2011; 44:1163-5.

[35] Huffman J W, Dai D., Martin, B. R., Compton, D. R. Design, Synthesis, and Pharmacology of Cannabimimetic Indoles. Bioorg Med Chem Lett 1994; 4:563-66.

[36] Drugs-Forum. JWH-018 or JWH-073, which do you prefer? In: http://www.drugs-forum.com/forum/showthread.php?t=103276, editor: Substance Information Network (S.I.N.) Foundation, 2009.

[37] Moller I, Wintermeyer A, Bender K, Jubner M, Thomas A, Krug O, et al. Screening for the synthetic cannabinoid JWH-018 and its major metabolites in human doping controls. Drug Test Anal 2010.

[38] Grigoryev A, Savchuk S, Melnik A, Moskaleva N, Dzhurko J, Ershov M, et al. Chromatography-mass spectrometry studies on the metabolism of synthetic cannabinoids JWH-018 and JWH-073, psychoactive components of smoking mixtures. J Chromatogr B Analyt Technol Biomed Life Sci 2011; 879:1126-36.

[39] Brents L K, Reichard E E, Zimmerman S M, Moran J H, Fantegrossi W E, Prather P L. Phase I Hydroxylated Metabolites of the K2 Synthetic Cannabinoid JWH-018 Retain In Vitro and In Vivo Cannabinoid 1 Receptor Affinity and Activity. PLoS One 2011; 6:e21917.

[40] Huffman J W, Zengin G, Wu M J, Lu J, Hynd G, Bushell K, et al. Structure-activity relationships for 1-alkyl-3-(1-naphthoyl)indoles at the cannabinoid CB(1) and CB(2) receptors: steric and electronic effects of naphthoyl substituents. New highly selective CB(2) receptor agonists. Bioorg Med Chem 2005; 13:89-112.

[41] Qi T, Qiu W, Liu Y, Zhang H, Gao X, Liu Y, et al. Synthesis, structures, and properties of disubstituted heteroacenes on one side containing both pyrrole and thiophene rings. J Org Chem 2008; 73:4638-43.

[42] Denton J R. One-Pot Desultonylative Alkylation of N-Sulfonyl Azacycles Using Alkoxides Generated by Phase-Transfer Catalysis. Synthesis 2010; 5:775-82.

[43] Prather P L, Martin N A, Breivogel C S, Childers S R. Activation of cannabinoid receptors in rat brain by WIN 55212-2 produces coupling to multiple G protein alpha-subunits with different potencies. Mol Pharmacol 2000; 57:1000-10.

[44] Shoemaker J L, Joseph B K, Ruckle M B, Mayeux P R, Prather P L. The endocannabinoid noladin ether acts as a full agonist at human CB2 cannabinoid receptors. J Pharmacol Exp Ther 2005; 314:868-75.

[45] Cheng Y, Prusoff W H. Relationship between the inhibition constant (K1) and the concentration of inhibitor which causes 50 percent inhibition (150) of an enzymatic reaction. Biochem Pharmacol 1973; 22:3099-108.

[46] Cheng H C. The power issue: determination of KB or Ki from IC50. A closer look at the Cheng-Prusoff equation, the Schild plot and related power equations. J Pharmacol Toxicol Methods 2001; 46:61-71.

[47] Thomas A, Stevenson L A, Wease K N, Price M R, Baillie G, Ross R A, et al. Evidence that the plant cannabinoid Delta9-tetrahydrocannabivarin is a cannabinoid CB1 and CB2 receptor antagonist. Br J Pharmacol 2005; 146:917-26.

[48] Aung M M, Griffin G, Huffman J W, Wu M, Keel C, Yang B, et al. Influence of the N-1 alkyl chain length of cannabimimetic indoles upon CB(1) and CB(2) receptor binding. Drug Alcohol Depend 2000; 60:133-40.

[49] Smith P B, Compton D R, Welch S P, Razdan R K, Mechoulam R, Martin B R. The pharmacological activity of anandamide, a putative endogenous cannabinoid, in mice. J Pharmacol Exp Ther 1994; 270:219-27.

[50] Huestis M A. Human cannabinoid pharmacokinetics. Chem Biodivers 2007; 4:1770-804.

[51] Atwood B K, Lee D, Straiker A, Widlanski T S, Mackie K. CP47,497-C8 and JWH073, commonly found in 'Spice' herbal blends, are potent and efficacious CB(1) cannabinoid receptor agonists. Eur J Pharmacol 2011; 659: 139-45.

[52] Mikasova L, Groc L, Choquet D, Manzoni O J. Altered surface trafficking of presynaptic cannabinoid type 1

[53] Burston J J, Wiley J L, Craig A A, Selley D E, Sim-Selley U. Regional enhancement of cannabinoid CB₁ receptor desensitization in female adolescent rats following repeated Delta-tetrahydrocannabinol exposure. Br J Pharmacol 2010; 161:103-12.

[54] Gorzalka B B, Hill M N. Putative role of endocannabinoid signaling in the etiology of depression and actions of antidepressants. Prog Neuropsychopharmacol Biol Psychiatry 2010.

[55] Li C, Jones P M, Persaud S J. Role of the endocannabinoid system in food intake, energy homeostasis and regulation of the endocrine pancreas. Pharmacol Ther 2011; 129:307-20.

[56] Watkins B A, Hutchins H, Li Y, Seifert M F. The endocannabinoid signaling system: a marriage of PUFA and musculoskeletal health. J Nutr Biochem 2010; 21:1141-52.

[57] Karst M, Wippermann S, Ahrens J. Role of cannabinoids in the treatment of pain and (painful) spasticity. Drugs 2010; 70:2409-38.

[58] Bisogno T, Di Marzo V. Cannabinoid receptors and endocannabinoids: role in neuroinflammatory and neurodegenerative disorders. CNS Neurol Disord Drug Targets 2010; 9:564-73.

[59] Gorzalka B B, Hill M N, Chang S C. Male-female differences in the effects of cannabinoids on sexual behavior and gonadal hormone function. Horm Behav 2010; 58:91-9.

[60] Jutras-Aswad D, DiNieri J A, Harkany T, Hurd Y L. Neurobiological consequences of maternal *cannabis* on human fetal development and its neuropsychiatric outcome. Eur Arch Psychiatry Clin Neurosci 2009; 259:395-412.

[61] McKallip R J, Nagarkatti M, Nagarkatti P S. Delta-9-tetrahydrocannabinol enhances breast cancer growth and metastasis by suppression of the antitumor immune response. J Immunol 2005; 174:3281-9.

[62] Haney M. The marijuana withdrawal syndrome: diagnosis and treatment. Curr Psychiatry Rep 2005; 7:360-6.

[63] Allsop D J, Norberg M M, Copeland J, Fu S, Budney A J. The *Cannabis* Withdrawal Scale development: Patterns and predictors of *cannabis* withdrawal and distress. Drug Alcohol Depend 2011.

[64] Hirvonen J, Goodwin R S, Li C T, Terry G E, Zoghbi S S, Morse C, et al. Reversible and regionally selective down-regulation of brain cannabinoid CB(1) receptors in chronic daily *cannabis* smokers. Mol Psychiatry 2011.

[65] Budney A J, Hughes J R. The *cannabis* withdrawal syndrome. Curr Opin Psychiatry 2006; 19:233-8.

[66] Vandrey R, Umbricht A, Strain E C. Increased blood pressure after abrupt cessation of daily *cannabis* use. J Addict Med 2011; 5:16-20.

[67] Drugs-Forum. JWH-073 experiences. In: http://www.drugs-forum.com/forum/showthread.php?t=82829, editor: Substance Information Network (S.I.N.) Foundation, 2009.

[68] Di Marzo V, Matias I. Endocannabinoid control of food intake and energy balance. Nat Neurosci 2005; 8:585-9.

[69] Beyer C E, Dwyer J M, Piesla M J, Platt B J, Shen R, Rahman Z, et al. Depression-like phenotype following chronic CB1 receptor antagonism. Neurobiol Dis 2010; 39:148-55.

[70] Tam J, Vemuri V K, Liu J, Batkai S, Mukhopadhyay B, Godlewski G, et al. Peripheral CB1 cannabinoid receptor blockade improves cardiometabolic risk in mouse models of obesity. J Clin Invest 2010; 120:2953-66.

[71] Nogueiras R, Veyrat-Durebex C, Suchanek P M, Klein M, Tschöp J, Caldwell C, Woods S C, Wittmann G, Watanabe M, Liposits Z, Fekete C, Reizes O, Rohner-Jeanrenaud F, Tschöp M H. Peripheral, but not central, CB1 antagonism provides food intake-independent metabolic benefits in diet-induced obese rats. Diabetes 2008; 57(11):2977-91.

[72] Tam J, Vemuri V K, Liu J, Batkai S, Mukhopadhyay B, Godlewski G, et al. Peripheral CB1 cannabinoid receptor blockade improves cardiometabolic risk in mouse models of obesity. J Clin Invest 2010; 120:2953-66.

[73] Cabral G A, Griffin-Thomas L. Emerging role of the cannabinoid receptor CB2 in immune regulation: therapeutic prospects for neuroinflammation. Expert reviews in molecular medicine 2009; 11:e3.

[74] Cheung K P, Taylor K R, Jameson J M. immunomodulation at epithelial sites by obesity and metabolic disease. Immunologic research 2011.

[75] Kunos G, Tam J. The case for peripheral CB receptor blockade in the treatment of visceral obesity and its cardiometabolic complications. British journal of pharmacology 2011; 163:1423-31.

[76] Parfieniuk A, Flisiak R. Role of cannabinoids in chronic liver diseases. World J Gastroenterol 2008; 14:6109-14.

[77] Cluny N L, Vemuri V K, Chambers A P, Limebeer C L, Bedard H, Wood J T, et al. A novel peripherally restricted cannabinoid receptor antagonist, AM6545, reduces food intake and body weight, but does not cause malaise, in rodents. British journal of pharmacology 2010; 161:629-42.

[78] Tamvakopoulos C S, Colwell L F, Barakat K, Fenyk-Melody J, Griffin P R, Nargund R, et al. Determination of brain and plasma drug concentrations by liquid chromatography/tandem mass spectrometry. Rapid Commun Mass Spectrom 2000; 14:1729-35.

[79] Randall P A, Vemuri V K, Segovia K N, Torres E F, Hosmer S, Nunes E J, et al. The novel cannabinoid CB1 antagonist AM6545 suppresses food intake and food-reinforced behavior. Pharmacology, biochemistry, and behavior 2010; 97:179-84.

[80] Bisht S, Khan M A, Bekhit M, Bai H, Cornish T, Mizuma M, et al. A polymeric nanoparticle formulation of curcumin (NanoCurc) ameliorates CCl4-induced hepatic injury and fibrosis through reduction of pro-inflammatory cytokines and stellate cell activation. Laboratory investigation; a journal of technical methods and pathology 2011; 91:1383-95.

[81] Gabbay E, Avraham Y, Ilan Y, Israeli E, Berry E M. Endocannabinoids and liver disease-review. Liver Int. 2005; 25(5):921-6.

[82] Huffman, J. W.; Lainton, J. A. H. *Current Medicinal Chemistry* 1996, 3, 101.

[83] Seely, K. A.; Prather, P. L.; James, L. P.; Moran, J. H. *Mol Interv* 2011, 11, 36.

[84] Gaoni, Y.; Mechoulam, R. *Journal of the American Chemical Society* 1964, 86, 1646.

[85] Lambert, D. M.; Fowler, C. J. *J Med Chem* 2005, 48, 5059.

[86] Matsuda, L. A.; Lolait, S. J.; Brownstein, M. J.; Young, A. C.; Bonner, T. I. *Nature* 1990, 346, 561.

[87] Munro, S.; Thomas, K. L.; Abu-Shaar, M. *Nature* 1993, 365, 61.

[88] Janero, D. R.; Makriyannis, A. *Expert Opinion on Emerging Drugs* 2009, 14, 43.

[89] Padgett, L. W. *Life Sci* 2005, 77, 1767.

[90] Mouslech, Z.; Valla, V. *Neuro Endocrinol Lett* 2009, 30, 153.

[91] D'Ambra, T. E.; Estep, K. G.; Bell, M. R.; Eissenstat, M. A.; Josef, K. A.; Ward, S. J.; Haycock, D. A.; Baizman, E. R.; Casiano, F. M.; Beglin, N. C.; et al. *J Med Chem* 1992, 35, 124.

[92] Bell, M. R.; D'Ambra, T. E.; Kumar, V.; Eissenstat, M. A.; Herrmann, J. L., Jr.; Wetzel, J. R.; Rosi, D.; Philion, R. E.; Daum, S. J.; Hlasta, D. J.; et al. *J Med Chem* 1991, 34, 1099.

[93] Huffman, J. W.; Zengin, G.; Wu, M. J.; Lu, J.; Hynd, G.; Bushell, K.; Thompson, A. L.; Bushell, S.; Tartal, C.; Hurst, D. P.; Reggio, P. H.; Selley, D. E.; Cassidy, M. P.; Wiley, J. L.; Martin, B. R. *Bioorganic & Medicinal Chemistry* 2005, 13, 89.

[94] Compton, D. R.; Gold, L. H.; Ward, S. J.; Balster, R. L.; Martin, B. R. *J Pharmacol Exp Ther* 1992, 263, 1118.

[95] Lainton, J. A. H.; Huffman, J. W.; Martin, B. R.; Compton, D. R. *Tetrahedron Letters* 1995, 36, 1401.

[96] Wiley, J. L.; Compton, D. R.; Dai, D.; Lainton, J. A.; Phillips, M.; Huffman, J. W.; Martin, B. R. *J Pharmacol Exp Ther* 1998, 285, 995.

[97] Aung, M. M.; Griffin, G.; Huffman, J. W.; Wu, M.; Keel, C.; Yang, B.; Showalter, V. M.; Abood, M. E.; Martin, B. R. *Drug Alcohol Depend* 2000, 60, 133.

[98] Brents, L. K.; Gallus-Zawada, A.; Radominska-Pandya, A.; Vasiljevik, T.; Prisinzano, T. E.; Fantegrossi, W. E.; Moran, J. H.; Prather, P. L. *Biochemical Pharmacology* 2012, 83, 952.

[99] Basavarajappa, B. S.; Cooper, T. B.; Hungund, B. L. *Brain Res* 1998, 793, 212.

[100] Basavarajappa, B. S.; Hungund, B. L. *J Neurochem* 1999, 72, 522.

[101] Wang, L.; Liu, J.; Harvey-White, J.; Zimmer, A.; Kunos, G. *Proceedings of the National Academy of Sciences of the United States of America* 2003, 100, 1393.

[102] Hungund, B. L.; Szakall, I.; Adam, A.; Basavarajappa, B. S.; Vadasz, C. *J Neurochem* 2003, 84, 698.

[103] Christensen, R.; Kristensen, P. K.; Bartels, E. M.; Bliddal, H.; Astrup, A. *Lancet* 2007, 370, 1706.

[104] Xi, Z. X.; Peng, X. Q.; Li, X.; Song, R.; Zhang, H. Y.; Liu, Q. R.; Yang, H. J.; Bi, G. H.; Li, J.; Gardner, E. L. *Nat Neurosci* 2011, 14, 1160.

[105] Morales, M.; Bonci, A. *Nat Med* 2012, 18, 504.

[106] Cheng, Y.; Prusoff, W. H. *Biochemical Pharmacology* 1973, 22, 3099.

[107] Martin, B. R.; Compton, D. R.; Thomas, B. F.; Prescott, W. R.; Little, P. J.; Razdan, R. K.; Johnson, M. R.; Melvin, L. S.; Mechoulam, R.; Ward, S. *J. Pharmacol Biochem Behav* 1991, 40, 471.

[108] Compton, D. R.; Johnson, M. R.; Melvin, L. S.; Martin, B. R. *J Pharmacol Exp Ther* 1992, 260, 201.

[109] Keane, B.; Leonard, B. E. *Alcohol Alcohol* 1989, 24, 299.

[110] Cunningham, C. L.; Fidler, T. L.; Hill, K. G. *Alcohol Res Health* 2000, 24, 85.

[111] Vinod, K. Y.; Yalamanchili, R.; Thanos, P. K.; Vadasz, C.; Cooper, T. B.; Volkow, N. D.; Hungund, B. L. *Synapse* 2008, 62, 574.

[112] Ravinet Trillou, C.; Arnone, M.; Delgorge, C.; Gonalons, N.; Keane, P.; Maffrand, J. P.; Sou brie, P. *Am J Physiol Regul Integr Comp Physiol* 2003, 284, R345.

[113] Kirkham, T. C. *Am J Physiol Regul Integr Comp Physiol* 2003, 284, R343.

[114] Biala, G.; Budzynska, B. *Pharmacol Rep* 2010, 62, 797.

[115] Basavarajappa, B. S. *Mini Rev Med Chem* 2007, 7, 769.

[116] Qi, T.; Qiu, W.; Liu, Y.; Zhang, H.; Gao, X.; Liu, Y.; Lu, K.; Du, C.; Yu, G.; Zhu, D. *Journal of Organic Chemistry* 2008, 73, 4638.

[117]. Willemen, M. J. C., Mantel-Teeuwisse, A. K., Buggy, Y., Layton, D., Straus, S. M. J. M., Leufkens, H. G. M., and Egberts, T. C. G. (2012) Reasons for and Time to Discontinuation of Rimonabant Therapy: A Modified Prescription-Event Monitoring Study, *Drug Safety* 35, 1147-1158.

All patents, patent documents, and other references cited are hereby incorporated by reference.

What is claimed is:

1. A composition comprising a compound of formula III:

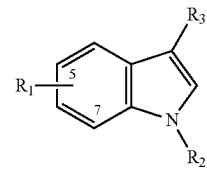

wherein $R_1$ is 5-O-methyl, 7-O-methyl, or 7-OH;
$R_2$ is $C_1$-$C_6$ linear alkyl;
and $R_3$ is

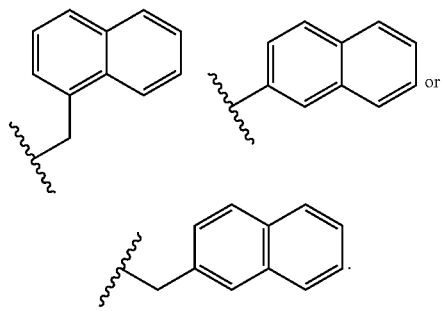

2. The composition of claim 1 wherein the $R_2$ is n-butyl.
3. The composition of claim 1 wherein $R_1$ is 7-O-methyl.
4. The composition of claim 1 wherein $R_3$ is

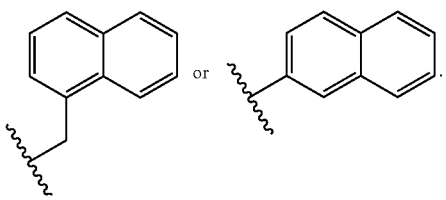 [SMILES: *Cc1cccc2ccccc12 ; *c1ccc2ccccc2c1]

5. The composition of claim 1 wherein the compound has a $K_D$ for CB1R and CB2R of less than 1 micromolar.

6. The composition of claim 5 wherein the compound has a $K_D$ for CB1R and CB2R of less than 100 nM.

7. The composition of claim 1 wherein the compound is a neutral CB1R antagonist.

8. The composition of claim 1 wherein the compound is a CB2R agonist.

9. The composition of claim 1 wherein the compound is TV-5-249 or TV-6-41.

10. The composition of claim 1 wherein the composition is a pharmaceutical composition.

11. The composition of claim 10 wherein the pharmaceutical composition is a sterile solution for injection.

12. The composition of claim 10 wherein the pharmaceutical composition is tablet, capsule, gel cap, or pill for oral administration.

13. The composition of claim 10 wherein the pharmaceutical composition is a unit dosage composition for treating alcoholism or drug abuse in a human.

14. A method of treating alcohol or drug abuse in a human comprising:
   administering a compound of formula III in an amount and for a time effective to treat alcohol or drug abuse in a human in need thereof:

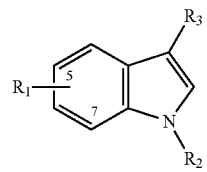

wherein $R_1$ is 5-O-methyl, 7-O-methyl, or 7-OH; $R_2$ is $C_1$-$C_6$ linear alkyl; and $R_3$ is

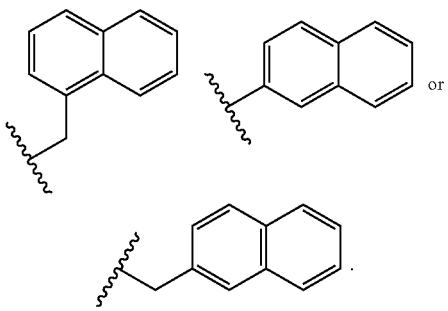

15. The method of claim 14 wherein the compound is TV-5-249 or TV-6-41.

* * * * *